US006890726B1

(12) United States Patent
Sauer et al.

(10) Patent No.: US 6,890,726 B1
(45) Date of Patent: May 10, 2005

(54) METHOD FOR SELECTING RECOMBINASE VARIANTS WITH ALTERED SPECIFICITY

(75) Inventors: Brian Lee Sauer, Oklahoma City, OK (US); Andreas Walter Rufer, Oklahoma City, OK (US)

(73) Assignee: Oklahoma Medical Research Foundation, Oklahoma, OK (US)

( * ) Notice: Subject to any disclaimer, the term of this patent is extended or adjusted under 35 U.S.C. 154(b) by 0 days.

(21) Appl. No.: 09/544,045

(22) Filed: Apr. 6, 2000

Related U.S. Application Data

(60) Provisional application No. 60/127,977, filed on Apr. 6, 1999.

(51) Int. Cl.⁷ .............................................. G01N 33/573
(52) U.S. Cl. ........................... 435/7.4; 435/6; 435/455; 536/23.1
(58) Field of Search ............................ 435/7.4, 6, 455; 536/23.1

(56) References Cited

U.S. PATENT DOCUMENTS

| | | |
|---|---|---|
| 4,959,317 A | 9/1990 | Sauer |
| 5,300,431 A | 4/1994 | Pierce et al. |
| 5,334,515 A | 8/1994 | Rashtchian et al. |
| 5,354,668 A | 10/1994 | Auerbach |
| 5,378,618 A | 1/1995 | Sternberg et al. |
| 5,434,066 A | 7/1995 | Bebee et al. |
| 5,441,884 A | 8/1995 | Baum |
| 5,478,731 A | 12/1995 | Short |
| 5,510,099 A | 4/1996 | Short et al. |
| 5,527,695 A | 6/1996 | Hodges et al. |
| 5,530,191 A | 6/1996 | Maliga |
| 5,539,094 A | 7/1996 | Reed et al. |
| 5,589,362 A | 12/1996 | Bujard et al. |
| 5,591,609 A | 1/1997 | Auerbach |
| 5,596,089 A | 1/1997 | Silversides et al. |
| 5,612,205 A | 3/1997 | Kay et al. |
| 5,614,389 A | 3/1997 | Auerbach |
| 5,629,159 A | 5/1997 | Anderson |
| 5,629,179 A | 5/1997 | Mierendorf et al. |
| 5,635,381 A | 6/1997 | Hooykaas et al. |
| 5,639,726 A | 6/1997 | Lawrence et al. |
| 5,641,748 A | 6/1997 | Hsu |
| 5,641,866 A | 6/1997 | Reed et al. |
| 5,643,727 A | 7/1997 | Reed et al. |
| 5,650,298 A | 7/1997 | Bujard et al. |
| 5,650,308 A | 7/1997 | Baum |
| 5,650,491 A | 7/1997 | Reed et al. |
| 5,654,168 A | 8/1997 | Bujard et al. |
| 5,654,182 A | 8/1997 | Wahl et al. |
| 5,656,438 A | 8/1997 | Hsu |
| 5,658,772 A | 8/1997 | Odell et al. |
| 5,677,177 A * | 10/1997 | Wahl et al. ............... 435/325 |
| 5,679,523 A | 10/1997 | Li et al. |
| 5,686,595 A | 11/1997 | Reed et al. |
| 5,721,118 A | 2/1998 | Scheffler |
| 5,721,367 A | 2/1998 | Kay et al. |
| 5,723,287 A | 3/1998 | Russell et al. |
| 5,723,333 A | 3/1998 | Levine et al. |
| 5,723,765 A | 3/1998 | Oliver et al. |
| 5,731,182 A | 3/1998 | Boyce |
| 5,733,733 A | 3/1998 | Auerbach |
| 5,733,743 A | 3/1998 | Johnson et al. |
| 5,733,744 A | 3/1998 | Hamilton |
| 5,736,377 A | 4/1998 | Band |
| 5,744,336 A | 4/1998 | Hodges et al. |
| 5,744,343 A | 4/1998 | Draetta et al. |
| 5,756,671 A | 5/1998 | Gyuris et al. |
| 5,763,240 A | 6/1998 | Zarling et al. |
| 5,767,376 A | 6/1998 | Stiles et al. |
| 5,770,384 A | 6/1998 | Androphy et al. |
| 5,773,697 A | 6/1998 | Tomes et al. |
| 5,776,449 A | 7/1998 | Baum |
| 5,777,194 A | 7/1998 | Scott et al. |
| 5,789,156 A | 8/1998 | Bujard et al. |
| 5,792,632 A | 8/1998 | Dujon et al. |
| 5,792,833 A | 8/1998 | Androphy et al. |

(Continued)

FOREIGN PATENT DOCUMENTS

| | | |
|---|---|---|
| EP | 0 332 104 A2 | 9/1989 |
| EP | 0 337 532 A1 | 10/1989 |
| EP | 0 344 029 A1 | 11/1989 |
| WO | WO 90/11361 A1 | 10/1990 |

OTHER PUBLICATIONS

Wall Transgenic livestock: Progress and prospects for the future. Theriogeniology vol. 45:57–68, 1966.*

Jaroff Fixing the genes. Time vol. 153(1):68–91, 1999.*

(Continued)

Primary Examiner—James Ketter
Assistant Examiner—David A. Lambertson
(74) Attorney, Agent, or Firm—Fulbright & Jaworski

(57) ABSTRACT

Disclosed are variants of Cre recombinase that have broadened specificity for the site of recombination. Specifically, the disclosed variants mediate recombination between sequences other than the loxP sequence and other lox site sequences on which wild type Cre recombinase is active. In general, the disclosed Cre variants mediate efficient recombination between lox sites that wild type Cre can act on (referred to as wild type lox sites), between variant lox sites not efficiently utilized by wild type Cre (referred to as variant lox sites), and between a wild type lox site and a variant lox site. Also disclosed are methods or recombining nucleic acids using the disclosed Cre variants. For example, the disclosed Cre variants can be used in any method or technique where Cre recombinase (or other, similar recombinases such as FLP) can be used. In addition, the disclosed Cre variants allow different alternative recombinations to be performed since the Cre variants allow much more efficient recombination between wild type lox sites and variant lox sites. Control of such alternative recombination can be used to accomplish more sophisticated sequential recombinations to achieve results not possible with wild type Cre recombinase.

23 Claims, 25 Drawing Sheets

| | | |
|---|---|---|
| 5,795,726 A | 8/1998 | Glucksmann |
| 5,795,734 A | 8/1998 | Flanagan et al. |
| 5,800,998 A | 9/1998 | Glucksmann |
| 5,801,030 A | 9/1998 | McVey et al. |
| 5,807,708 A | 9/1998 | Falb et al. |
| 5,807,995 A | 9/1998 | Cohen et al. |
| 5,814,300 A | 9/1998 | Scott et al. |
| 5,814,500 A | 9/1998 | Dietz |
| 5,814,618 A | 9/1998 | Bujard et al. |
| 5,817,492 A | 10/1998 | Saito et al. |
| 5,830,461 A | 11/1998 | Billiar et al. |
| 5,830,698 A | 11/1998 | Reff et al. |
| 5,830,729 A | 11/1998 | Jaisser et al. |
| 5,834,202 A | 11/1998 | Auerbach |
| 5,837,242 A | 11/1998 | Holliger et al. |
| 5,837,844 A | 11/1998 | Hsu |
| 5,840,540 A | 11/1998 | St. George-Hyslop et al. |
| 5,843,694 A | 12/1998 | Band |
| 5,843,742 A | 12/1998 | Natsoulis et al. |
| 5,843,744 A | 12/1998 | Baum |
| 5,844,079 A | 12/1998 | Ingham et al. |
| 5,849,553 A | 12/1998 | Anderson et al. |
| 5,849,571 A | 12/1998 | Glorioso et al. |
| 5,849,572 A | 12/1998 | Glorioso et al. |
| 5,849,708 A | 12/1998 | Maratos-Flier |
| 5,849,989 A | 12/1998 | Edlund |
| 5,849,995 A | 12/1998 | Hayden et al. |
| 5,851,808 A | 12/1998 | Elledge et al. |
| 5,854,067 A | 12/1998 | Newgard et al. |
| 5,858,657 A | 1/1999 | Winter et al. |
| 5,859,310 A | 1/1999 | Bujard et al. |
| 5,866,361 A | 2/1999 | Dujon et al. |
| 5,866,755 A | 2/1999 | Bujard et al. |
| 5,871,907 A | 2/1999 | Winter et al. |
| 5,877,400 A | 3/1999 | Tomes et al. |
| 5,882,888 A | 3/1999 | Jørgensen |
| 5,882,893 A | 3/1999 | Goodearl |
| 5,885,776 A | 3/1999 | Stone et al. |
| 5,885,779 A | 3/1999 | Sadowski et al. |
| 5,885,793 A | 3/1999 | Griffiths et al. |
| 5,885,836 A | 3/1999 | Wahl et al. |
| 5,888,732 A | 3/1999 | Hartley et al. |
| 5,888,981 A | 3/1999 | Bujard et al. |

OTHER PUBLICATIONS

Sigmund Viewpoint: Are studies in genetically altered mice out of control? Arterioscler. Thromb. Vasc. Biol. Vo. 20:1425–1429, 2000.*

Miller et al. Int–h: an int mutation of phage Lambda that enhances site–specific recombination. Cell. vol. 20:721–729, 1980.*

Serre et al. DNA splicing by an active site mutant of Flp recombinase. J. Biol. Chem. vol. 268(1):455–463, 1993.*

Ackroyd et al. Site–specific recombination by mutants of Tn21 resolvase with DNA recognition functions from Tn3 resolvase. J. Mol. Biol. vol. 216:633–643, 1990.*

McCormick et al. Cointegrates carrying two copies of a Tn3 derivative in an inverted orientation. Gene vol. 34:197–206, 1984.*

Lee et al. A novel mutant of LoxP containing part of long terminal repeat of HIV–1 in spacer region: Presentation of possible target site for antiviral strategy using site–specific recombinase. Biochem Biophys Res. Commun. vol. 253:588–593, Mar. 1998.*

Abremski, et al., "Studies on the properties of P1 site–specific recombination: evidence for topologically unlinked products following recombination," *Cell* 32(4):1301–11 (1983).

Alvarado–Urbina, et al., "Automated synthesis of gene fragments," *Science* 214(4518):270–4 (1981).

Ammerer, "Expression of genes in yeast using the ADCI promoter," *Methods Enzymol.* 101:192–201 (1983).

Andrus, Production of Seedless Watermelons, USDA Tech. Bull. No. 1425 (1971).

Antonucci, et al., "Eukaryotic promoters drive gene expression in *Escherichia coli*," *J. Biol. Chem.* 264(30):17656–9 (1989).

Aoki, et al., "Efficient generation of recombinant adenoviral vectors by Cre–lox recombination in vitro," *Mol. Med.* 5(4):224–31 (1999).

Barker, et al., "Cellular localization of soybean storage protein mRNA in transformed toacco seeds," *Proc. Natl. Acad. Sci.* 85:458–462 (1988).

Barnes & Rine, "Regulated expression of endonuclease EcoRI in *Saccharomyces cerevisiae*: nuclear entry and biological consequences," *Proc. Natl. Acad. Sci. U. S. A.* 82(5):1354–8 (1985).

Beachy, et al., "Accumulation and assembly of soybean – conglycinin in seeds of transformed petunia plants," *EMBO J* 4:3047–3053 (1985).

Berlin & Sauer, "In situ color detection of alpha–L–arabinofuranosidase, a "no–background" reporter gene, with 5–bromo–3–indolyl– –L–arabinofuranoside," *Anal. Biochem.* 243(1):171–5 (1996).

Blochlinger & Diggelmann, "Hygromycin B phosphotransferase as a selectable marker for DNA transfer experiments with higher eucaryotic cells," *Mol. Cell. Biol.* 4(12):2929–31 (1984).

Brink & Cooper, "The endosperm in seed development," *Bot. Rev.* 8:423–541 (1947).

Broglie, et al., "Functional analysis of DNA sequences responsible for ethylene regulation of a bean chitinase gene in transgenic tobacco," *Plant Cell.* 1(6):599–607 (1989).

Chalfie, et al., "Green fluorescent protein as a marker for gene expression," *Science* 263(5148):802–5 (1994).

Chen, et al., "A DNA sequence that confers seed–specific enhancement to a constitutive promoter," *EMBO J* 7(2):297–302 (1988).

Chen, et al., "Functional analysis of box 1 mutations in yeast site–specific recombinases Flp and R: pairwise complementation with recombinase variants lacking the active–site tyrosine," *Molecular and Cellular Biology* 12(9):3757–3765 (1992).

Chen, et al., "Functional analysis of regulatory elements in a plant embryo–specific gene," *Proc. Natl. Acad. Sci. U. S. A.* 83(22):8560–4 (1986).

Chen, et al., "Regulated expression of genes encoding soybean beta–conglycinins in transgenic plants," *Dev. Genet.* 10(2):112–22 (1989).

Colot, et al., "Localization of sequences in wheat endosperm protein genes which confer tissue–specific expression in tobacco," *EMBO J* 6: 3559–3564 (1987).

Cormack, et al., "FACS–optimized mutants of the green fluorescent protein (GFP)," *Gene* 173(1 Spec No):33–8 (1996).

Craig, "The mechanism of conservative site–specific recombination," *Annu. Rev. Genet.* 22:77–105 (1988).

Depicker, et al., "Nopaline synthase: transcript mapping and DNA sequence," *J. Mol. Appl. Genet.* 1(6):561–73 (1982).

Diaz, et al., "The prokaryotic beta–recombinase catalyzes site–specific recombination in mammalian cells," *J. Biol. Chem.* 274(10):6634–40 (1999).

Dunsmuir et al., "The major chlorophyll a/b binding protein of petunia is composed of several polypeptides encoded by a number of distinct nuclear genes," *J. Mol. Appl. Genet.* 2(3):285–300 (1983).

Fisch, et al., "A strategy of exon shuffling for making large peptide repertoires displayed on filamentous bacteriophage," *Proc. Natl. Acad. Sci. U. S. A.* 93(15):7761–66 (1996).

Gagneten, et al., "Brief expression of a GFPcre fusion gene in embyonic stem cells allows rapid retrieval of sire–specific genomic deletions," *Nucleic Acids Research* 25(16):3326–3331 (1997).

Goldberg, et al., "Regulation of gene expression during plant embryogenesis," *Cell* 56(2):149–60 (1989).

Gorman, et al., "High efficiency DNA–mediated transformation of primate cells," *Science* 221(4610):551–3 (1983).

Gorman, et al., "The Rous sarcoma virus long terminal repeat is a strong promoter when introduced into a variety of eukaryotic cells by DNA–mediated transfection," *Proc. Natl. Acad. Sci. U. S. A.* 79(22):6777–81 (1982).

Guo, et al., "Structure of Cre recombinase complexed with DNA in a site–specific recombination synapse," *Nature* 389(6646):40–6 (1997).

Gurley, et al., "Upstream sequences required for efficient expression of a soybean heat shock gene," *Mol. Cell. Biol.* 6(2):559–65 (1986).

Guzman, et al., "Tight regulation, modulation, and high–level expression by vectors containing the arabinose PBAD promoter," *J. Bacteriol.* 177(14):4121–30 (1995).

Hagan & Guilfoyle, "Rapid induction of selective transcription by auxins," *Mol. Cell. Biol.* 5(6):1197–203 (1985).

Hallet, et al., "Transposition and site–specific recombination: adapting DNA cut–and–paste mechanisms to a variety of genetic rearrangements," *FEMS Microbiol. Rev.* 21(2):157–78 (1997).

Hartung & Kisters–Woike, "Cre mutants with altered DNA binding properties," *J Biol Chem* 273(36):22884–22891 (1998).

Henderson, "Effect of cultivar, polyploidy and 'reciprical' hybrodization on charcters important in breeding triploid seedless watermelon hybrids," *J. Amer. Soc. Sci.* 102:293–297 (1977).

Higgins, et al., "Synthesis and regulation of major proteins in seeds," *Ann. Rev. Plant Physiol.* 35:191–221 (1984).

Higgins, et al., "The sequence of a pea vicilin gene and its expression in transgenic tobacco plants," *Plant Mol. Biol.* 11:109–123 (1988).

Hoess, et al., "Isolation and characterization of intermediates in site–specific recombination," *Proc. Natl. Acad. Sci. U. S. A.* 84(19):6840–4 (1987).

Hoess, et al., "P1 site–specific recombination: nucleotide sequence of the recombining sites," *Proc. Natl. Acad. Sci. U. S. A.* 79(11):3398–402 (1982).

Hoess, et al., "The role of the loxP spacer region in P1 site–specific recombination," *Nucleic Acids Res.* 14(5):2287–300 (1986).

Hoffman, et al., "A modified storage protein is synthesized, processed, and degraded in the seeds of transgenic plants," *Plant Mol. Biol.* 11:717–729 (1988).

Hoffman, et al., "Synthesis and protein body deposition of maize 15–kd zein in transgenic tobacco seeds," *EMBO J* 6:3213–3221 (1987).

Hsu, et al., "Concentrations of sucrose and nitrogenous compounds in the apoplast of developing soybean seed coats and embryos," *Plant Physiol.* 75:181 (1984).

Jayaram, "Two–micrometer circle site–specific recombination: the minimal substrate and the possible role of flanking sequences," *Proc. Natl. Acad. Sci. U. S. A.* 82(17):5875–9 (1985).

Johnston & Davis, "Sequences that regulate the divergent *GAL1–GAL10* promoter in *Saccharomyces cerevisiae*," *Mol. Cell. Biol.* 4(8):1440–48 (1984).

Kihara, "Triploid Watermelons," *Proc. Soc. Hort. Sci.* 58:217–230 (1951).

Kühn et al., "Inducible gene targeting in mice," *Science* 269(5229):1427–9 (1995).

Lakso, et al., "Targeted oncogene activation by site–specific recombination in transgenic mice," *Proc. Natl. Acad. Sci. U. S. A.* 89(14):6232–6 (1992).

Lee & Saito, "Role of nucleotide sequences of loxP spacer region in Cre–mediated recombination," *Gene* 216(1):55–65 (1998).

Liebke, et al., "The sequence of the distal end of the *E. coli* ribosomal RNA rrnE operon indicates conserved features are shared by rrn operons," *Nucleic Acids Res.* 13(15):5515–25 (1985).

Marcotte, et al., "Regulation of a wheat promoter by abscisic acid in rice protoplasts," *Nature* 335:454–457 (1988).

Marris, et al., "The 5' flnaking region of a barley B hordein gene controls tissue and developmental specific CAT expression in tobacco plants," *Plant Mol. Biol.* 10:359–366 (1988).

Mazur & Chui, "Sequence of a genomic DNA clone for the small subunit of ribulose bis–phosphate carboxylase–oxygenase from tobacco," *Nucleic Acids Res.* 13(7):2373–86 (1985).

Metzger, et al., "Conditional site–specific recombination in mammalian cells using a ligand–dependent chimeric Cre recombinase," *Proc. Natl. Acad. Sci. U. S. A.* 92(15):6991–5 (1995).

Miyada, et al., "Regulation of the araC gene of *Escherichia coli*: catabolite repression, autoregulation, and effect on araBAD expression," *Proc. Natl. Acad. Sci. U. S. A.* 81(13):4120–4 (1984).

Mondragon, "Unraveling transposition: gamma delta resolvase in complex with DNA," *Structure* 3(8):755–8 (1995).

Mullins, et al., "Efficient Cre–lox linearisation of BACs: applications to physical mapping and generation of transgenic animals," *Nucleic Acids Res.* 25(12):2539–40 (1997).

Naito, et al., "Differential expression of conglycinin ' and ' subunit genes in trasngenic plants," *Plant Mol. Biol.* 11:683–695 (1988).

Newbigin, et al., "Pea convicilin: structure and primary sequence of the protein and expression of a gene in the seeds of trasgenic tobacco," *Planta* 180:461 (1990).

Nunes–Döby et al., "Similarities and differences among 105 members of the Int family of site–specific recombinases," *Nucleic Acids Res.* 26(2):391–406 (1998).

Odell, et al., "Identification of DNA sequences required for activity of the cauliflower mosaic virus 35S promoter," *Nature* 313(6005):810–2 (1985).

Offler & Patrick, "Cellular structures, plasma membrane surface areas and plasmodesmatal frequencies of seed coats of *Phaseolus vulgaris* L. in relation to photosynthate transfer," *Aust. J. Plant Physiol.* 11:79 (1984).

Okamuro, et al., Soybean seed lectin gene and flanking nonseed protein genes are developmentally regulated in transformed tobacco plants, *Proc. Natl. Acad. Sci. U. S. A.* 83(21):8240–4 (1986).

Oram, et al., "Recombination. Pieces of the site–specific recombination puzzle," Curr. Biol. 5(10):1106–9 (1995).

Paddon & Hartley, "Expression of Bacillus amyloliquefaciens extracellular ribonuclease (barnase) in Escherichia coli following in inactivating mutation," Gene 53(1):11–9 (1987).

Pan, et al., "Mechanism of cleavage and ligation by FLP recombinase: classification of mutations in FLP protein by in vitro complementation analysis," Molecular and Cellular Biology 13(6):3167–3175 (1993).

Parsons, et al., "Functional analysis of Arg–308 mutants of Flp recombinase," J Biol Chem 265:4527–4533 (1990).

Patrick, "Photosynthate unloading from seed coats of Phaseolus vulgaris L. control by tisue water relations," J. Plant Physiol. 115: 297 (1984).

Patrick, "Sieve element unloading: cellular pathway, mechanism and control," Physiol. Plant 78: 298 (1990).

Pavlakis & Hamer, "Regulation of a metallothionein–growth hormone hybrid gene in bovine papilloma virus," Proc. Natl. Acad. Sci. U. S. A. 80(2):397–401 (1983).

Perez–Grau & Goldberg, "Soybean seed protein genes are regulated spatially during embryogenesis," Plant Cell 1:1095–1109 (1989).

Radke, et al., "Transformation of Brassica napus L. using Agrobacterium tumefaciens: developmentally regulated expression of a reintroduced napin gene," Theor. Appl. Genet. 75:685–694 (1988).

Riggs, et al., "Utilization of luciferase fusion genes to monitor differential regulation of phytohemagglutinin and phaseolin promotes in transgenic tobacco," Plant Sci. 63:47–57 (1989).

Sambrook et al., Cold Spring Harbor, New York: Cold Spring Harbor Laboratory Press (Second Edition) (1989). (Table of Contents).

Sanford, The biolistic process, Tibtech 6:299–302 (1988).

Sano & Cantor, "Expression of a cloned streptavidin gene in Escherichia coli," Proc. Natl. Acad. Sci. U. S. A. 87(1):142–6 (1990).

Sauer & Henderson, "Cre–stimulated recombination at loxP–containing DNA sequences placed into the mammalian genome," Nucleic Acids Res. 17(1):147–61 (1989).

Sauer & Henderson, "Site–specific DNA recombination in mammalian cells by the Cre recombinase of bacteriophage P1," Proc. Natl. Acad. Sci. U. S. A. 85(14):5166–70 (1988).

Sauer & Henderson, "Targeted insertion of exogenous DNA into the eukaryotic genome by the Cre recombinase," New Biol. 2(5):441–9 (1990).

Sauer, "Identification of cryptic lox sites in the yeast genome by selection of Cre–mediated chromosome translocations that confer multiple drug resistance," J. Mol. Biol., 223:911–928 (1992).

Sauer, "Functional expression of the cre–lox site–specific recombination system in the yeast Saccharomyces cerevisiae," Mol. Cell. Biol. 7(6):2087–96 (1987).

Sauer, "Inducible gene targeting in mice using the Cre/lox system," Methods 14(4):381–92 (1998).

Sauer, "Manipulation of transgenes by site–specific recombination: use of Cre recombinase," Methods Enzymol. 225:890–900 (1993).

Sauer, "Multiplex Cre/lox recombination permits selective site–specific DNA targeting to both a natural and an engineered site in the yeast genome," Nucleic Acids Res. 24(23):4608–13 (1996).

Sauer, et al., "Construction of isogenic cell lines expressing human and rat angiotensin II AT1 receptors by Cre–mediated site–specific recombination," Methods 4:143–149 (1992).

Sauer, et al., "Site–specific insertion of DNA into a pseudorabies virus vector," Proc. Natl. Acad. Sci. U. S. A. 84(24):9108–12 (1987).

Senecoff & Cox, "Directionality in FLP protein–promoted site–specific recombination is mediated by DNA–DNA pairing," J. Biol. Chem. 261(16):7380–6 (1986).

Senecoff, et al., "DNA recognition by the FLP recombinase of the yeast 2 mu plasmid. A mutational analysis of the FLP binding site," J. Mol. Biol. 201(2):405–21 (1988).

Sengupta–Goplalan, et al., "Developmentally regulated expression of the bean –phaseolin gene in tobacco seed," Proc. Natl. Acad. Sci. USA 82:3320–3324 (1985).

Shirsat, et al., "Sequence responsible for the tissue specific promoter activity of a pea legumin gene in tobacco," Mol. Gen. Genet. 215(2):326–31 (1989).

Sigal & Alberts, "Genetic recombination: the nature of a crossed strand–exchange between two homologous DNA molecules," J. Mol. Biol. 71(3):789–93 (1972).

Southern & Berg, "Transformation of mammalian cells to antibiotic resistance with a bacterial gene under control of the SV40 early region promoter," J. Mol. Appl. Genet. 1(4):327–41 (1982).

Stemmer, "DNA shuffling by random fragmentation and reassembly: in vitro recombination for molecular evolution," Proc. Natl. Acad. Sci. U. S. A. 91(22):10747–51 (1994).

Stemmer, "Rapid evolution of a protein in vitro by DNA shuffling," Nature 370(6488):389–91 (1994).

Sternberg & Hamilton, "Bacteriophage P1 site–specific recombination. I. Recombination between loxP sites," J. Mol. Biol. 150(4):467–86 (1981).

Sternberg, et al., "Bacteriophage P1 cre gene and its regulatory region. Evidence for multiple promoters and for regulation by DNA methylation," J. Mol. Biol. 187(2):197–212 (1986).

Stiles, et al., "DNA sequence of a mutation in the leader region of the yeast iso–1–cytochrome c mRNA," Cell 25(1):277–84 (1981).

Stinchcomb, et al., "Isolation and characterisation of a yeast chromosomal replicator," Nature 282(5734):39–43 (1979).

Tessman & Peterson, "Isolation of protease–proficient, recombinase–deficient recA mutants of Escherichia coli K–12," Journal of Bacteriology 163(2):688–695 (1985).

Tessman & Peterson, "Plaque color method for rapid isolation of novel recA mutants of Escherichia coli K–12: new classes of protease–constitutive recA mutants," Journal of Bacterioogy 163(2):677–687 (1985).

Thorne & Rainbird, "An in vivo technique for the study of phloem unloading in seed coats of developing soybean seeds," Plant Physiol. 72:268 (1983).

Umlauf & Cox, "The functional significance of DNA sequence structure in a site–specific genetic recombination reaction," EMBO J. 7(6):1845–52 (1988).

Vandekerckhove, et al., "Enkephalins produced in transgenic plants using modified 2S seed storage proteins," Bio/Technology 7: 929–932 (1989).

Velten, et al., "Isolation of a dual plant promoter fragment from the Ti plasmid of Agrobacterium tumefaciens," EMBO J. 12: 2723–2370 (1984).

Voelker, et al., "Differences in expression between two seed lectin alleles obtained from normal and lectin–deficient beans are maintained in transgenic tobacco," *EMBO J* 6:3571–3577 (1987).

Walling, et al., "Transcriptional and post–transcriptional regulation of soybean seed protein mRNA levels," *Proc. Natl. Acad, Sci. USA* 83: 2123–2127 (1986).

Waterhouse, et al., "Combinatorial infection and in vivo recombination: a strategy for making large phage antibody repertoires," *Nucleic Acids Res.* 21(9):2265–6 (1993).

Wierzbicki, et al., "A mutational analysis of the bacteriophage P1 recombinase Cre," *J. Mol. Biol.* 195(4):785–94 (1987).

Wolswinkel & Ammerlaan, "Characteristics of sugar, amino acid and phophate release from the seed coat of developing seeds of *Vicia faba* and *Pisum sativum*," J. *Exp. Bot*. 36: 359 (1985).

Woodcock, et al., "Quantitative evaluation of *Escherichia coli* host strains for tolerance to cytosine methylation in plasmid and phage recombinants," *Nucleic Acids Res.* 17(9):3469–78 (1989).

Yamaizumi, et al., "One molecule of diphtheria toxin fragment A introduced into a cell can kill the cell," *Cell* 15(1):245–50 (1978).

Zalkin & Yanofsky, "Yeast gene TRP5: structure, function, regulation," *J. Biol. Chem..* 257(3):1491–500 (1982).

Zhang, et al., "Inducible site–directed recombination in mouse embryonic stem cells," *Nucleic Acids Research* 24(4):543–548 (1996).

Zolotukhin, et al., "A "humanized" green fluorescent protein cDNA adapted for high–level expression in mammalian cells," *J. Virol.* 70(7):4646–54 (1996).

* cited by examiner loxP vs. loxK1 vs. loxK2 loxP  5'ATA ACT TCG TAT AAT GTA TGC TAT ACG AAG TTA T 3'
      3'TAT TGA AGC ATA TTA CAT ACG ATA TGC TTC AAT A 5' loxK1 5'GAG CCT TTG TAT ATA CCT TTC TAT ACA AAG GCT T 3'
      3'CTC GGA AAC ATA TAT GGA AAG ATA TGT TTC CGA A 5' loxK2 5'GAT ACA ACG TAT ATA CCT TTC TAT ACG TTG TAT T 3'
      3'CTA TGT TGC ATA TAT GGA AAG ATA TGC AAC ATA A 5'

FIG. 1

100 bp 300 bp ca. 2 kb 1.1 kb cre 300 bp

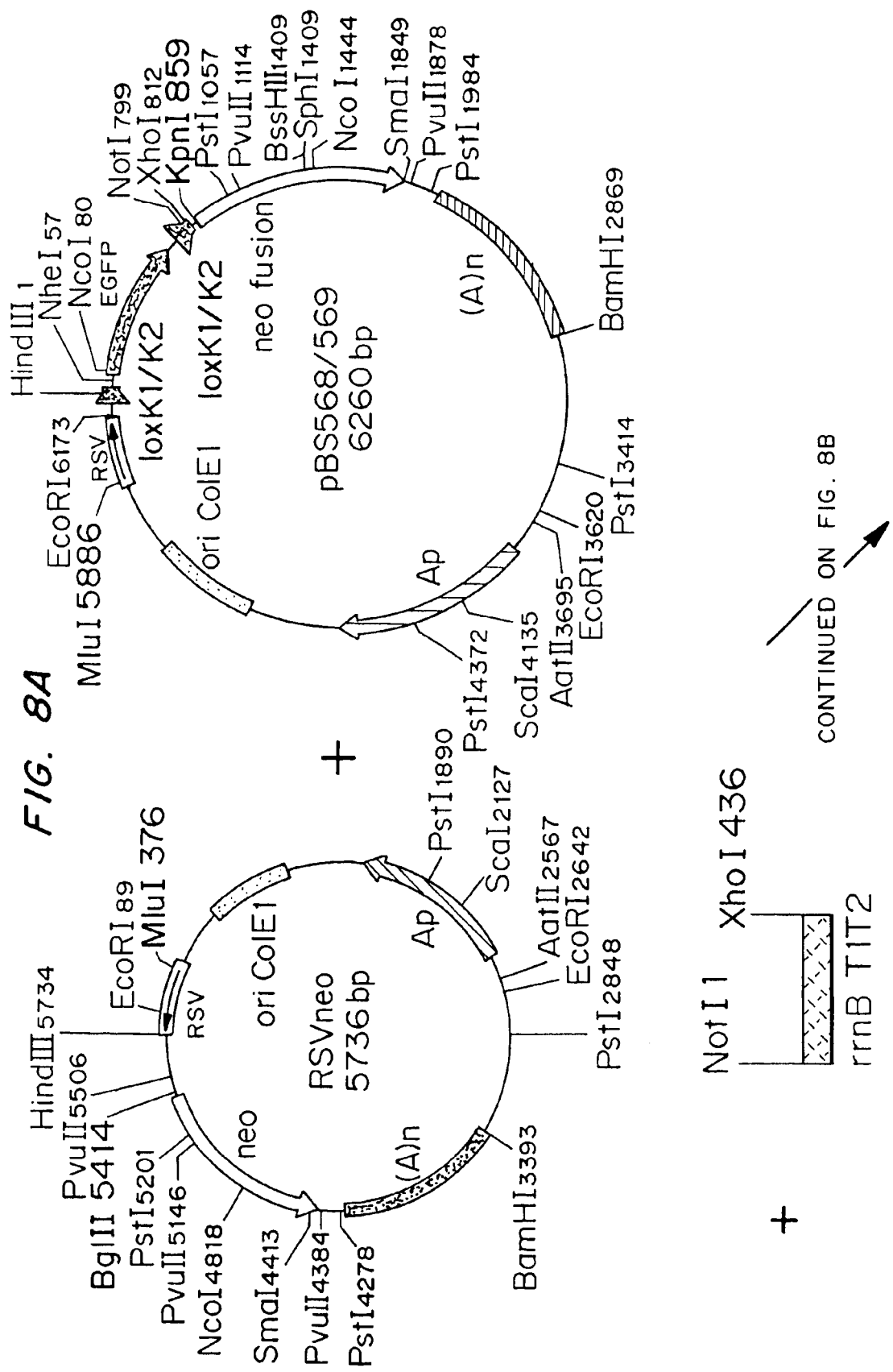

INTERRUPTED
(DELETION)

FLANKED
(DELETION)

INVERTED
(INVERSION)

DELETION

INVERSION

COMBINATION

FIG. 15

| | TT | TG | GT | GG | TC | CC | AA |
|---|---|---|---|---|---|---|---|
| R3M3 Cre | 97 | 99 | 92 | 82 | 56 | 67 | 90 |
| E262G/D29A Cre | 95 | 95 | 82 | 37 | 35 | 34 | 47 |
| E262G/T316S Cre | 98 | 97 | 89 | 21 | 31 | 14 | 32 |
| E262G/D189N Cre | 93 | 98 | 68 | 6 | 9 | 5 | 22 |
| E262G Cre | 90 | 97 | 65 | 20 | 32 | 10 | 28 |
| wt Cre | 95 | 92 | 25 | 0 | 0 | 0 | 0 |

% Cre-mediated $lox^2$ recombination loxP Halfsite: ATAACTTCGTATA

SEQUENCE LISTING

<160> NUMBER OF SEQ ID NOS: 68

<210> SEQ ID NO 1
<211> LENGTH: 343
<212> TYPE: PRT
<213> ORGANISM: Artificial Sequence
<220> FEATURE:
<223> OTHER INFORMATION: Cre

<400> SEQUENCE: 1

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30
```

-continued

```
Asp Arg Gln Ala Phe Ser Glu His Thr Trp Lys Met Leu Leu Ser Val
        35                  40                  45
Cys Arg Ser Trp Ala Ala Trp Cys Lys Leu Asn Asn Arg Lys Trp Phe
 50                  55                  60
Pro Ala Glu Pro Glu Asp Val Arg Asp Tyr Leu Leu Tyr Leu Gln Ala
 65                  70                  75                  80
Arg Gly Leu Ala Val Lys Thr Ile Gln Gln His Leu Gly Gln Leu Asn
                 85                  90                  95
Met Leu His Arg Arg Ser Gly Leu Pro Arg Pro Ser Asp Ser Asn Ala
                100                 105                 110
Val Ser Leu Val Met Arg Arg Ile Arg Lys Glu Asn Val Asp Ala Gly
                115                 120                 125
Glu Arg Ala Lys Gln Ala Leu Ala Phe Glu Arg Thr Asp Phe Asp Gln
                130                 135                 140
Val Arg Ser Leu Met Glu Asn Ser Asp Arg Cys Gln Asp Ile Arg Asn
145                 150                 155                 160
Leu Ala Phe Leu Gly Ile Ala Tyr Asn Thr Leu Leu Arg Ile Ala Glu
                165                 170                 175
Ile Ala Arg Ile Arg Val Lys Asp Ile Ser Arg Thr Asp Gly Gly Arg
                180                 185                 190
Met Leu Ile His Ile Gly Arg Thr Lys Thr Leu Val Ser Thr Ala Gly
                195                 200                 205
Val Glu Lys Ala Leu Ser Leu Gly Val Thr Lys Leu Val Glu Arg Trp
                210                 215                 220
Ile Ser Val Ser Gly Val Ala Asp Asp Pro Asn Asn Tyr Leu Phe Cys
225                 230                 235                 240
Arg Val Arg Lys Asn Gly Val Ala Ala Pro Ser Ala Thr Ser Gln Leu
                245                 250                 255
Ser Thr Arg Ala Leu Glu Gly Ile Phe Glu Ala Thr His Arg Leu Ile
                260                 265                 270
Tyr Gly Ala Lys Asp Asp Ser Gly Gln Arg Tyr Leu Ala Trp Ser Gly
                275                 280                 285
His Ser Ala Arg Val Gly Ala Ala Arg Asp Met Ala Arg Ala Gly Val
                290                 295                 300
Ser Ile Pro Glu Ile Met Gln Ala Gly Gly Trp Thr Asn Val Asn Ile
305                 310                 315                 320
Val Met Asn Tyr Ile Arg Asn Leu Asp Ser Glu Thr Gly Ala Met Val
                325                 330                 335
Arg Leu Leu Glu Asp Gly Asp
                340
```

<210> SEQ ID NO 2
<211> LENGTH: 13
<212> TYPE: DNA
<213> ORGANISM: artificial sequence
<220> FEATURE:
<223> OTHER INFORMATION: Inverted repeat sequence
<220> FEATURE:
<221> NAME/KEY: misc_feature
<222> LOCATION: (1)..(3)
<223> OTHER INFORMATION: N at positions 1-3 can be A, T, G, or C.
<220> FEATURE:
<221> NAME/KEY: misc_feature
<222> LOCATION: (6)..(7)
<223> OTHER INFORMATION: N at positions 6 and 7 can be A, T, G, or C.

<400> SEQUENCE: 2

```
nnnacnncgt ata                                                  13
```

<210> SEQ ID NO 3
<211> LENGTH: 34
<212> TYPE: DNA
<213> ORGANISM: artificial sequence
<220> FEATURE:
<223> OTHER INFORMATION: variant lox sites
<220> FEATURE:
<221> NAME/KEY: misc_feature
<222> LOCATION: (1)..(3)
<223> OTHER INFORMATION: N at postitions 1-3 can be A, G, C, or T
<220> FEATURE:
<221> NAME/KEY: misc_feature
<222> LOCATION: (6)..(7)
<223> OTHER INFORMATION: N at positions 6 and 7 can be A, T, G, C,
<220> FEATURE:
<221> NAME/KEY: misc_feature
<222> LOCATION: (14)..(21)
<223> OTHER INFORMATION: N at positions 14-21 can A, G, T, or C
<220> FEATURE:
<221> NAME/KEY: misc_feature
<222> LOCATION: (28)..(29)
<223> OTHER INFORMATION: N at postions 28 and 29 can be A, T, G, or C
<220> FEATURE:
<221> NAME/KEY: misc_feature
<222> LOCATION: (32)..(34)
<223> OTHER INFORMATION: N at postiions 32-34 can be A, T, G, or C

<400> SEQUENCE: 3

```
nnnacnncgt atannnnnnn ntatacgnng tnnn                           34
```

<210> SEQ ID NO 4
<211> LENGTH: 33
<212> TYPE: DNA
<213> ORGANISM: artificial sequence
<220> FEATURE:
<223> OTHER INFORMATION: variant lox sites

<400> SEQUENCE: 4

```
gatacaacgt ataccctttc ctatacgttg tat                            33
```

<210> SEQ ID NO 5
<211> LENGTH: 34
<212> TYPE: DNA
<213> ORGANISM: artificial sequence
<220> FEATURE:
<223> OTHER INFORMATION: Specific and non-specific sequences for Cre
      recombinase
<220> FEATURE:
<221> NAME/KEY: misc_feature
<222> LOCATION: (1)..(3)
<223> OTHER INFORMATION: N at postions 1-3 can be A, T, G, or C
<220> FEATURE:
<221> NAME/KEY: misc_feature
<222> LOCATION: (14)..(21)
<223> OTHER INFORMATION: N at positions 14-21 can be A, T, C, or G
<220> FEATURE:
<221> NAME/KEY: misc_feature
<222> LOCATION: (32)..(34)
<223> OTHER INFORMATION: N at positions 32-34 can be A, T, G, or C

<400> SEQUENCE: 5

```
nnnacttcgt atannnnnnn ntatacgaag tnnn                           34
```

<210> SEQ ID NO 6
<211> LENGTH: 8
<212> TYPE: PRT
<213> ORGANISM: artificial sequence
<220> FEATURE:
<223> OTHER INFORMATION: oligonucleotide -continued

```
<400> SEQUENCE: 6

Ala Thr Arg Val Asx Tyr Gly Cys
1               5

<210> SEQ ID NO 7
<211> LENGTH: 34
<212> TYPE: DNA
<213> ORGANISM: artificial sequence
<220> FEATURE:
<223> OTHER INFORMATION: primer

<400> SEQUENCE: 7
ataacttcgt ataatgtatg ctatacgaag ttat                              34

<210> SEQ ID NO 8
<211> LENGTH: 29
<212> TYPE: DNA
<213> ORGANISM: artificial sequence
<220> FEATURE:
<223> OTHER INFORMATION: primer

<400> SEQUENCE: 8
aaataatcta gactgagtgt gaaatgtcc                                    29

<210> SEQ ID NO 9
<211> LENGTH: 31
<212> TYPE: DNA
<213> ORGANISM: artificial sequence
<220> FEATURE:
<223> OTHER INFORMATION: primer

<400> SEQUENCE: 9
atatataagc ttatcattta cgcgttaatg g                                 31

<210> SEQ ID NO 10
<211> LENGTH: 33
<212> TYPE: DNA
<213> ORGANISM: artificial sequence
<220> FEATURE:
<223> OTHER INFORMATION: primer

<400> SEQUENCE: 10
ataagcggcc gctgagcttg gctgttttgg cgg                               33

<210> SEQ ID NO 11
<211> LENGTH: 36
<212> TYPE: DNA
<213> ORGANISM: artificial sequence
<220> FEATURE:
<223> OTHER INFORMATION: primer

<400> SEQUENCE: 11
gccgtctcga gagagtttgt agaaacgcaa aaaggc                            36

<210> SEQ ID NO 12
<211> LENGTH: 30
<212> TYPE: DNA
<213> ORGANISM: artificial sequence
<220> FEATURE:
<223> OTHER INFORMATION: primer

<400> SEQUENCE: 12
gtcaagctag ctagcaggtt tcccgactgg                                   30

<210> SEQ ID NO 13
```

<211> LENGTH: 36
<212> TYPE: DNA
<213> ORGANISM: artificial sequence
<220> FEATURE:
<223> OTHER INFORMATION: primer

<400> SEQUENCE: 13
acattgcggc cgcagatctc tctagagtc gacctg        36

<210> SEQ ID NO 14
<211> LENGTH: 20
<212> TYPE: DNA
<213> ORGANISM: artificial sequence
<220> FEATURE:
<223> OTHER INFORMATION: primer

<400> SEQUENCE: 14
tttgggctag cgaattcgag        20

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
tttgggccag ctaaacatgc        20

<210> SEQ ID NO 16
<211> LENGTH: 20
<212> TYPE: DNA
<213> ORGANISM: artificial sequence
<220> FEATURE:
<223> OTHER INFORMATION: primer

<400> SEQUENCE: 16
cggtgggaga atgttaatcc        20

<210> SEQ ID NO 17
<211> LENGTH: 18
<212> TYPE: DNA
<213> ORGANISM: artificial sequence
<220> FEATURE:
<223> OTHER INFORMATION: primer

<400> SEQUENCE: 17
ggacacagtg cccgtgtc        18

<210> SEQ ID NO 18
<211> LENGTH: 21
<212> TYPE: DNA
<213> ORGANISM: artificial sequence
<220> FEATURE:
<223> OTHER INFORMATION: primer

<400> SEQUENCE: 18
tctgcgttct gatttaatct g        21

<210> SEQ ID NO 19
<211> LENGTH: 18
<212> TYPE: DNA
<213> ORGANISM: artificial sequence
<220> FEATURE:
<223> OTHER INFORMATION: primer

<400> SEQUENCE: 19

-continued ccaggccagg tatctctg                                                          18

<210> SEQ ID NO 20
<211> LENGTH: 22
<212> TYPE: DNA
<213> ORGANISM: artificial sequence
<220> FEATURE:
<223> OTHER INFORMATION: primer

<400> SEQUENCE: 20
gtacgtgaga tatctttaac cc                                                     22

<210> SEQ ID NO 21
<211> LENGTH: 22
<212> TYPE: DNA
<213> ORGANISM: artificial sequence
<220> FEATURE:
<223> OTHER INFORMATION: primer

<400> SEQUENCE: 21
ttgctggata gttttactg cc                                                      22

<210> SEQ ID NO 22
<211> LENGTH: 45
<212> TYPE: DNA
<213> ORGANISM: artificial sequence
<220> FEATURE:
<223> OTHER INFORMATION: primer

<400> SEQUENCE: 22
gctatcaact cgcgccctgg gagggatttt tgaagcaact catcg                            45

<210> SEQ ID NO 23
<211> LENGTH: 45
<212> TYPE: DNA
<213> ORGANISM: artificial sequence
<220> FEATURE:
<223> OTHER INFORMATION: primer

<400> SEQUENCE: 23
gagttgcttc aaaaatccct cccagggcgc gagttgatag ctggc                            45

<210> SEQ ID NO 24
<211> LENGTH: 45
<212> TYPE: DNA
<213> ORGANISM: artificial sequence
<220> FEATURE:
<223> OTHER INFORMATION: primer

<400> SEQUENCE: 24
gctatcaact cgcgccctgg cagggatttt tgaagcaact catcg                            45

<210> SEQ ID NO 25
<211> LENGTH: 45
<212> TYPE: DNA
<213> ORGANISM: artificial sequence
<220> FEATURE:
<223> OTHER INFORMATION: primer

<400> SEQUENCE: 25
gagttgcttc aaaaatccct gccagggcgc gagttgatag ctggc                            45

<210> SEQ ID NO 26
<211> LENGTH: 45
<212> TYPE: DNA

```
<213> ORGANISM: artificial sequence
<220> FEATURE:
<223> OTHER INFORMATION: primer
<220> FEATURE:
<221> NAME/KEY: misc_feature
<222> LOCATION: (17)..(25)
<223> OTHER INFORMATION: N at positions 17-25 can be A, T, G, or C

<400> SEQUENCE: 26
gctatcaact cgcgccnnnn nnnnnatttt tgaagcaact catcg            45

<210> SEQ ID NO 27
<211> LENGTH: 45
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (17)..(25)
<223> OTHER INFORMATION: N at positions 17-25 can be A, T, G, or C

<400> SEQUENCE: 27
gagttgcttc aaaaatnnnn nnnnggcgc gagttgatag ctggc             45

<210> SEQ ID NO 28
<211> LENGTH: 1172
<212> TYPE: DNA
<213> ORGANISM: artificial sequence
<220> FEATURE:
<223> OTHER INFORMATION: wtCre

<400> SEQUENCE: 28
tttgggctag cgaattcgag ctcggtaccc ggggatcctc tagactgagt gtgaaatgtc     60
caatttactg accgtacacc aaaatttgcc tgcattaccg gtcgatgcaa cgagtgatga    120
ggttcgcaag aacctgatgg acatgttcag gatcgccag gcgttttctg agcatacctg    180
gaaaatgctt ctgtccgttt gccggtcgtg gcggcatgg tgcaagttga ataaccggaa    240
atggtttccc gcagaacctg aagatgttcg cgattatctt ctatatcttc aggcgcgcgg    300
tctggcagta aaaactatcc agcaacattt gggccagcta acatgcttc atcgtcggtc    360
cgggctgcca cgaccaagtg acagcaatgc tgtttcactg gttatgcggc ggatccgaaa    420
agaaaacgtt gatgccggtg aacgtgcaaa acaggctcta gcgttcgaac gcactgattt    480
cgaccaggtt cgttcactca tggaaaatag cgatcgctgc caggatatac gtaatctggc    540
atttctgggg attgcttata caccctgtt acgtatagcc gaaattgcca ggatcagggt    600
taaagatatc tcacgtactg acggtgggag aatgttaatc catattgca gaacgaaaac    660
gctggttagc accgcaggtg tagagaaggc acttagcctg ggggtaacta aactggtcga    720
gcgatggatt ccgtctctg gtgtagctga tgatccgaat aactacctgt tttgccgggt    780
cagaaaaaat ggtgttgccg cgccatctgc caccagccag ctatcaactc gcgccctgga    840
agggattttt gaagcaactc atcgattgat ttacggcgct aaggatgact ctggtcagag    900
atacctggcc tggtctggac acagtgcccg tgtcggagcc gcgcgagata tggcccgcgc    960
tggagtttca ataccggaga tcatgcaagc tggtggctgg accaatgtaa atattgtcat   1020
gaactatatc cgtaacctgg atagtgaaac agggcaatg gtgcgcctgc tggaagatgg   1080
cgattagcca ttaacgcgta atgataagc ttggctgttt tggcggatga gaagatttt   1140
tcagcctgat acagattaaa tcagaacgca ga                                1172
```

<210> SEQ ID NO 29
<211> LENGTH: 1172
<212> TYPE: DNA
<213> ORGANISM: artificial sequence
<220> FEATURE:
<223> OTHER INFORMATION: mxoxox1

<400> SEQUENCE: 29

| | | | | | |
|---|---|---|---|---|---|
| tttgggctag | cgaattcgag | ctcggtaccc | ggggatcctc | tagactgagt | gtgaaatgtc | 60 |
| caatttactg | accgtacacc | aaaatttgcc | tgcattacct | gtcgatgcaa | cgagtgatga | 120 |
| ggttcgcaag | aacctgatgg | ccatgttcag | ggatcgccag | gcgttttctg | agcatacctg | 180 |
| gaaaatgctt | ctgtccgttt | gccggtcgtg | ggcggcatgg | tgcaagttga | ataaccggaa | 240 |
| atggtttccc | gcagaacctg | aagatgttcg | cgattatctt | ctatatcttc | aggcgcgcgg | 300 |
| tctggcagta | aaaactatcc | agcaacattt | gggccagcta | acatgcttc | atcgtcggtc | 360 |
| cgggctgcca | cgaccaagtg | acagcaatgc | tgtttcactg | gttatgcggc | ggatccgaaa | 420 |
| agaaaacgtt | gatgccggtg | aacgtgcaaa | acaggctcta | gcgttcgaac | gcactgattt | 480 |
| cgaccaggtt | cgttcactca | tggaaaatag | cgatcgctgc | caggatatac | gtaatctggc | 540 |
| atttctgggg | attgcttata | acaccctgtt | acgtatagcc | gaaattgcca | ggatcagggt | 600 |
| taaagatatc | tcacgtacta | acggtgggag | aatgttaatc | catattggca | gaacgaaaac | 660 |
| gctggttagc | accgcaggtg | tagagaaggc | acttagtctg | ggggtaacta | aactggtcga | 720 |
| gcgatggatt | tccatctctg | gtgtagctga | tgatccgaat | aactacctgt | tttgccgggt | 780 |
| cagaaaaaat | ggtgttgccg | cgccatctgc | caccagccag | ctatcaactc | gcgccctggg | 840 |
| agggattttt | gaagcaactc | atcgattgat | ttacggcgct | aaggatgact | ctggtcagag | 900 |
| ataccctggcc | tggtctggac | acagtgcccg | tgtcggagcc | gcgcgagata | tggcccgcgc | 960 |
| tggagtttca | ataccggaga | tcatgcaagc | tggtggctgg | accaatgtaa | atattgtcat | 1020 |
| gaactatatc | cgtaacctgg | atagtgaaac | aggggcaatg | gtgcgcctgc | tggaagatgg | 1080 |
| cgattagcca | ttaacgcgta | aatgataagc | ttggctgttt | tggcggatga | gagaagattt | 1140 |
| tcagcctgat | acagattaaa | tcagaacgca | ga | | | 1172 |

<210> SEQ ID NO 30
<211> LENGTH: 1172
<212> TYPE: DNA
<213> ORGANISM: artificial sequence
<220> FEATURE:
<223> OTHER INFORMATION: mxoxox2

<400> SEQUENCE: 30

| | | | | | |
|---|---|---|---|---|---|
| tttgggctag | cgaattcgag | ctcggtaccc | ggggatcctc | tagactgagt | gtgaaatgtc | 60 |
| caatttactg | accgtacacc | aaaatttgcc | tgcattacct | gtcgatgcaa | cgagtgatga | 120 |
| ggttcgcaag | aacctgatgg | acatgttcag | ggatcgccag | gcgttttctg | agcatacctg | 180 |
| gaaaatgctt | ctgtccgttt | gccggtcgtg | ggcggcatgg | tgcaagttga | ataaccggaa | 240 |
| atggtttccc | gcagaacctg | aagatgttcg | cgattatctt | ctatatcttc | aggcgcgcgg | 300 |
| tctggcagta | aaaactatcc | agcaacattt | gggccagcta | acatgcttc | atcgtcggtc | 360 |
| cgggctgcca | cgaccaagtg | acagcaatgc | tgtttcactg | gttatgcggc | ggatccgaaa | 420 |
| agaaaacgtt | gatgccggtg | aacgtgcaaa | acaggctcta | gcgttcggac | gcactgattt | 480 |
| cgaccaggtt | cgttcactca | tggaaaatag | cgatcgctgc | caggatatac | gtaatctggc | 540 |
| atttctgggg | attgcttata | acaccctgtt | acgtatagcc | gaaattgcca | ggatcaggt | 600 |

```
taaagatatc tcacgtactg acggtgggag aatgttaatc catattggca gaacgaaaac    660
gctggttagc accgcaggtg tagagaaggc acttagcctg ggggtaacta aactggtcga    720
gcgatggatt tccgtctctg gtgtagctga tgatccgaat aactaccgt tttgccgggt     780 cagaaaaaat ggtgttgccg cgccatctgc caccggccag ctatcaactc gcgccctggg    840
agggattttt gaagcaactc atcgattgat ttacggcgct aaggatgact ctggtcagag    900
atacctggcc tggtccggac acagtgcccg tgtcggagcc gcgcgagata tggcccgcgc    960
tggagtttca ataccggaga tcatgcaagc tggtggctgg tccaatgtaa atattgtcat   1020
gaactatatc cgtaacctgg atagtgaaac aggggcaatg gtgcgcctgc tggaagatgg   1080
cgattagcca ttaacgcgta aatgataagc ttggctgttt tggcggatga gagaagattt   1140
tcagcctgat acagattaaa tcagaacgca ga                                 1172

<210> SEQ ID NO 31
<211> LENGTH: 1172
<212> TYPE: DNA
<213> ORGANISM: artificial sequence
<220> FEATURE:
<223> OTHER INFORMATION: mxoxox3

<400> SEQUENCE: 31
tttgggctag cgaattcgag ctcggtaccc ggggatcctc tagactgagt gtgaaatgtc     60
caatttactg accgtacacc aaaatttgcc tgcattaccg atcgatgcaa cgagtgatga    120
ggttcgcaag aacctgatgg acatgttcag ggatcgccag gcgttttctg agcatacctg    180
gaaaatgctt ctgtccgttt gccggtcgtg ggcggcatgg tgcaagttga ataaccggaa    240
atggtttccc gcagaacctg aagatgttcg cgattatctt ctatatcttc aggcgcgcgg    300
tctggcagta aaaactatcc agcaacattt gggccagcta acatgcttc atcgtcggtc     360 cgggctgcca cgaccaagtg acagcaatgc tgtttcactg gttatgcggc ggatccgaaa    420
agaaaacgtt gatgccggtg aacgtgcaaa acaggctcta gcgttcgaac gcactgattt    480
cgaccaggtt cgttcactca tggaaaatag cgatcgctgc caggatatac gtaatctggc    540
atttctgggg attgcttata cacccctgtt acgtatagcc gaaattgcca ggatcagggt    600
taaagatatc tcacgtacta acggtgggag aatgttaatc catattagca gaacgaaaac    660
gctggttagc accgcaggtg tagagaaggc acttagcctg ggggtaacta aactggtcga    720
gcaatggatt tccgtctctg gtgtagctga tgatccgaat aactaccgt tttgccgggt     780 cagaaaaaat ggtgttgccg cgccatctgc caccagccgg ctatcaactc gcgccctggg    840
agggattttt gaagcaactc atcgattgat ttacggcgct aaggatgact ctggtcagag    900
atacctggcc tggtccggac acagtgcccg tgtcggagcc gcgcgagata tggcccgcgc    960
tggagtttca atactggaga tcatgcaagc tggtggctgg accaatgtaa atattgtcat   1020
gaactatatc cgtaacctgg atagtgaaac aggggcaatg gtgcgcctgc tggaagatgg   1080
cgattagcca ttaacgcgta aatgataagc ttggctgttt tggcggatga gagaagattt   1140
tcagcctgat acagattaaa tcagaacgca ga                                 1172

<210> SEQ ID NO 32
<211> LENGTH: 1172
<212> TYPE: DNA
<213> ORGANISM: artificial sequence
<220> FEATURE:
<223> OTHER INFORMATION: mxoxox4

<400> SEQUENCE: 32
```

-continued

```
tttgggctag cgaattcgag ctcggtaccc ggggatcctc tagactgagt gtgaaatgtc      60
caatttactg accgtacacc aaaatttgcc tgcattaccg gtcgatgcaa cgagtgatga     120
ggttcgcaag aacctgatgg acatgttcag ggatcgccag gcgttttctg agcatacctg     180
gaaaatgctt ctgtccgttt gccggtcgtg ggcggcatgg tgcaagttga ataaccggaa     240
atggtttccc gcagaacctg aagatgttcg cgattatctt ctatgtcttc aggcgcgcgg     300
tctggcagta aaactatcc agcaacattt gggccagcta acatgcttc atcgtcggtc       360
cgggctgcca cgaccaagtg acagcaatgc tgtttcactg gttatgcggc ggatccgaaa     420
agaaaacgtt gatgccggtg aacgtgcaaa acaggctcta gcgttcaaac gcactgattt     480
cgaccaggtt cgttcactca tggaaaatag cgatcgctgc caggatatac gtaatctggc     540
atttctgggg attgcttata cacccctgtt acgtatagcc gaaattgcca ggatcagggt     600
taaagatatc tcacgtactg acggtgggag aatgttaatc catattgcca gaacgaaaac    660
gctggttagc accgcaggtg tagagaaggc acttagcctg ggggtaacta aactggtcga    720
gcgatggatt tccgtctctg gtgtagctga tgatccgaat aactacctgt tttgccgggt    780
cagaaaaaat ggtgttgccg cgccatctgc caccagccag ctatcaactc gcgccctgga   840
agggattttt gaagcaactc atcgattgat ttacggcgct aaggatgact ctggtcagag    900
ataccaggcc tggtctggac acagtgcccg tgtcggagcc gcgcgagata tggcccgcgc   960
tggagtttca ataccggaga tcatgcaagc tggtggctgg accaatgtaa atattgtcat  1020
gaactatatc cgtaacctgg atagtgaaac aggggcaatg gtgcgcctgc tggaagatgg  1080
cgattagcca ttaacgcgta aatgataagc ttggctgttt tggcggatga gagaagattt  1140
tcagcctgat acagattaaa tcagaacgca ga                                 1172
```

<210> SEQ ID NO 33
<211> LENGTH: 1172
<212> TYPE: DNA
<213> ORGANISM: artificial sequence
<220> FEATURE:
<223> OTHER INFORMATION: mxoxox5

<400> SEQUENCE: 33

```
tttgggctag cgaattcgag ctcggtaccc ggggatcctc tagactgagt gtgaaatgtc      60
caatttactg accgtacacc aaaatttgcc tgcattaccg gtcgatgcaa cgagtgatga     120
ggttcgcaag aacctgatgg ccatgttcag ggatcgccag gcgttttctg agcatacctg     180
gaaaatgctt ctgtccgttt gccggtcgtg ggcggcatgg tgcaagttga ataaccggaa     240
atggtttccc gcagaacctg aagatgttcg cgattatctt ctatatcttc aggcgcgcgg     300
tctggcagta aaactatcc agcaacattt gggccagcta acatgcttc atcgtcagtc      360
cgggctgcca cgaccaagtg acagcaatgc tgtttcactg gttatgcggc ggatccgaaa     420
agaaaacgtt gatgccggtg aacgtgcaaa acaggctcta gcgttcgaac gcactgattt     480
cgaccaggtt cgttcactca tggaaaatag cgatcgctgc caggatatac gtaatctggc     540
atttctgggg attgcttata cacccctgtt acgtatagcc gaaattgcca ggatcagggt     600
taaagatatc tcacgtactg acggtgggag aatgttaatc catattgcca gaacgaaaac    660
gctggttagc accgcaggtg tagagaaggc acttagcctg ggggtaacta aacaggtcga    720
gcgatggatt tccgtctctg gtgtagctga tgatccgaat aactacctgt tttgccgggt    780
cagaaaaaat ggtgttgccg cgccatctgc caccagccag ctatcaactc gcgccctggg   840
```

```
agggattttt gaagcaactc atcgattgat ttacggcgct aaggatgact ctggtcagag      900
atacctggcc tggtctggac acagtgcccg tgtcggagcc gcgcgagata tggcccgcgc      960
tggagtttca ataccggaga tcatgcaagc tggtggctgg tccaatgtaa atattgtcat     1020
gaactatatc cgtaacctgg atagtgaaac agggcaatg gtgcgcctgc tggaagatgg     1080
cgattagcca ttaacgcgta aatgataagc ttggctgttt tggcggatga gagaagattt     1140
tcagcctgat acagattaaa tcagaacgca ga                                    1172
```

<210> SEQ ID NO 34
<211> LENGTH: 1172
<212> TYPE: DNA
<213> ORGANISM: artificial sequence
<220> FEATURE:
<223> OTHER INFORMATION: mxoxox6

<400> SEQUENCE: 34

```
tttgggctag cgaattcgag ctcggtaccc ggggatcctc tagactgagt gtgaaatgtc       60
caatttactg accgtacacc aaaatttgcc tgcattaccg gtcgatgcaa cgagtgatga      120
ggttcgcaag aacctgatgg acatgttcag ggatcgccag gcgttttctg agcatacctg      180
gaaaatgctt ctgtccgttt gccggtcgtg ggcggcatgg tgcaagttga ataaccggaa      240
atggtttccc gcagaacctg aagatgttcg cgattatctt ctatatcttc aggcgcgcgg      300
tctggcagta aaactatcc agcaacattt gggccagcta acatgcttc atcgtcggtc       360 cgggctgcca cgaccaagtg acagcaatgc tgtttcactg gttatgcggc ggatccgaaa      420
agaaaacgtt gatgccggtg aacgtgcaaa acaggctcta gcgttcgaac gcactgattt      480
cgaccaggtt cgttcactca tggaaaatag cgatcgctgc caggatatac gtaatctggc      540
atttctgggg attgcttata cacccgtgtt acgtatagcc gaaattgcca ggatcagggt      600
taaagatatc tcacgtactg acggtgggag aatgttaatc catattggca gaacgaaaac      660
gctggttagc accgcaggtg tagagaaggc acttagcctg ggggtaacta aactggtcga      720
gcgatggatt tccgtctctg gtgtagctga tgatccgaat aactacctgt tttgccgggt      780
cagaaaaaat ggtgttgccg cgccatctgc caccagccag ctatcaactc gcgccctggg      840
agggattttt gaagcaactc atcgattgat ttacggcgct aaggatgact ctggtcagag      900
ataccaggcc tggtctggac acagtgcccg tgtcggagcc gcgcgagata tggcccgcgc      960
tggagtttca ataccggaga tcatgcaagc tggtggctgg tccaatgtaa atattgtcat     1020
gaactatatc cgtaacctgg atagtgaaac agggcaatg gtgcgcctgc tggaagatgg     1080
cgattagcca ttaacgcgta aatgataagc ttggctgttt tggcggatga gagaagattt     1140
tcagcctgat acagattaaa tcagaacgca ga                                    1172
```

<210> SEQ ID NO 35
<211> LENGTH: 343
<212> TYPE: PRT
<213> ORGANISM: artificial sequence
<220> FEATURE:
<223> OTHER INFORMATION: mxoxox1

<400> SEQUENCE: 35

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Ala Met Phe Arg
            20                  25                  30

Asp Arg Gln Ala Phe Ser Glu His Thr Trp Lys Met Leu Leu Ser Val

```
                35                  40                  45
Cys Arg Ser Trp Ala Ala Trp Cys Lys Leu Asn Asn Arg Lys Trp Phe
 50                  55                  60
Pro Ala Glu Pro Glu Asp Val Arg Asp Tyr Leu Leu Tyr Leu Gln Ala
 65                  70                  75                  80
Arg Gly Leu Ala Val Lys Thr Ile Gln Gln His Leu Gly Gln Leu Asn
                 85                  90                  95
Met Leu His Arg Arg Ser Gly Leu Pro Arg Pro Ser Asp Ser Asn Ala
            100                 105                 110
Val Ser Leu Val Met Arg Arg Ile Arg Lys Glu Asn Val Asp Ala Gly
            115                 120                 125
Glu Arg Ala Lys Gln Ala Leu Ala Phe Glu Arg Thr Asp Phe Asp Gln
130                 135                 140
Val Arg Ser Leu Met Glu Asn Ser Asp Arg Cys Gln Asp Ile Arg Asn
145                 150                 155                 160
Leu Ala Phe Leu Gly Ile Ala Tyr Asn Thr Leu Leu Arg Ile Ala Glu
                165                 170                 175
Ile Ala Arg Ile Arg Val Lys Asp Ile Ser Arg Thr Asn Gly Gly Arg
            180                 185                 190
Met Leu Ile His Ile Gly Arg Thr Lys Thr Leu Val Ser Thr Ala Gly
            195                 200                 205
Val Glu Lys Ala Leu Ser Leu Gly Val Thr Lys Leu Val Glu Arg Trp
            210                 215                 220
Ile Ser Ile Ser Gly Val Ala Asp Pro Asn Asn Tyr Leu Phe Cys
225                 230                 235                 240
Arg Val Arg Lys Asn Gly Val Ala Ala Pro Ser Ala Thr Ser Gln Leu
                245                 250                 255
Ser Thr Arg Ala Leu Gly Gly Ile Phe Glu Ala Thr His Arg Leu Ile
            260                 265                 270
Tyr Gly Ala Lys Asp Asp Ser Gly Gln Arg Tyr Leu Ala Trp Ser Gly
            275                 280                 285
His Ser Ala Arg Val Gly Ala Ala Arg Asp Met Ala Arg Ala Gly Val
            290                 295                 300
Ser Ile Pro Glu Ile Met Gln Ala Gly Gly Trp Thr Asn Val Asn Ile
305                 310                 315                 320
Val Met Asn Tyr Ile Arg Asn Leu Asp Ser Glu Thr Gly Ala Met Val
                325                 330                 335
Arg Leu Leu Glu Asp Gly Asp
            340

<210> SEQ ID NO 36
<211> LENGTH: 343
<212> TYPE: PRT
<213> ORGANISM: artificial sequence
<220> FEATURE:
<223> OTHER INFORMATION: mxoxox2

<400> SEQUENCE: 36

Met Ser Asn Leu Leu Thr Val His Gln Asn Leu Pro Ala Leu Pro Val
 1               5                  10                  15
Asp Ala Thr Ser Asp Glu Val Arg Lys Asn Leu Met Asp Met Phe Arg
                20                  25                  30
Asp Arg Gln Ala Phe Ser Glu His Thr Trp Lys Met Leu Leu Ser Val
            35                  40                  45
Cys Arg Ser Trp Ala Ala Trp Cys Lys Leu Asn Asn Arg Lys Trp Phe
```

-continued

```
                    50                  55                  60
Pro Ala Glu Pro Glu Asp Val Arg Asp Tyr Leu Leu Tyr Leu Gln Ala
 65                  70                  75                  80

Arg Gly Leu Ala Val Lys Thr Ile Gln Gln His Leu Gly Gln Leu Asn
                 85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Gly Arg Thr Asp Phe Asp Gln
130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Gly Gln Leu
                245                 250                 255

Ser Thr Arg Ala Leu Gly Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 37
<211> LENGTH: 343
<212> TYPE: PRT
<213> ORGANISM: artificial sequence
<220> FEATURE:
<223> OTHER INFORMATION: mxoxox3

<400> SEQUENCE: 37

```
Met Ser Asn Leu Leu Thr Val His Gln Asn Leu Pro Ala Leu Pro Ile
 1               5                  10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
```

-continued

```
                65                  70                  75                  80
Arg Gly Leu Ala Val Lys Thr Ile Gln Gln His Leu Gly Gln Leu Asn
                    85                  90                  95
Met Leu His Arg Arg Ser Gly Leu Pro Arg Pro Ser Asp Ser Asn Ala
                    100                 105                 110
Val Ser Leu Val Met Arg Ile Arg Lys Glu Asn Val Asp Ala Gly
                    115                 120                 125
Glu Arg Ala Lys Gln Ala Leu Ala Phe Glu Arg Thr Asp Phe Asp Gln
                    130                 135                 140
Val Arg Ser Leu Met Glu Asn Ser Asp Arg Cys Gln Asp Ile Arg Asn
145                 150                 155                 160
Leu Ala Phe Leu Gly Ile Ala Tyr Asn Thr Leu Leu Arg Ile Ala Glu
                    165                 170                 175
Ile Ala Arg Ile Arg Val Lys Asp Ile Ser Arg Thr Asn Gly Gly Arg
                    180                 185                 190
Met Leu Ile His Ile Ser Arg Thr Lys Thr Leu Val Ser Thr Ala Gly
                    195                 200                 205
Val Glu Lys Ala Leu Ser Leu Gly Val Thr Lys Leu Val Glu Gln Trp
210                 215                 220
Ile Ser Val Ser Gly Val Ala Asp Asp Pro Asn Asn Tyr Leu Phe Cys
225                 230                 235                 240
Arg Val Arg Lys Asn Gly Val Ala Ala Pro Ser Ala Thr Ser Arg Leu
                    245                 250                 255
Ser Thr Arg Ala Leu Gly Gly Ile Phe Glu Ala Thr His Arg Leu Ile
                    260                 265                 270
Tyr Gly Ala Lys Asp Asp Ser Gly Gln Arg Tyr Leu Ala Trp Ser Gly
                    275                 280                 285
His Ser Ala Arg Val Gly Ala Ala Arg Asp Met Ala Arg Ala Gly Val
                    290                 295                 300
Ser Ile Leu Glu Ile Met Gln Ala Gly Gly Trp Thr Asn Val Asn Ile
305                 310                 315                 320
Val Met Asn Tyr Ile Arg Asn Leu Asp Ser Glu Thr Gly Ala Met Val
                    325                 330                 335
Arg Leu Leu Glu Asp Gly Asp
                    340
```

<210> SEQ ID NO 38
<211> LENGTH: 343
<212> TYPE: PRT
<213> ORGANISM: artificial sequence
<220> FEATURE:
<223> OTHER INFORMATION: mxoxox4

<400> SEQUENCE: 38

```
Met Ser Asn Leu Leu Thr Val His Gln Asn Leu Pro Ala Leu Pro Val
1               5                   10                  15
Asp Ala Thr Ser Asp Glu Val Arg Lys Asn Leu Met Asp Met Phe Arg
                    20                  25                  30
Asp Arg Gln Ala Phe Ser Glu His Thr Trp Lys Met Leu Leu Ser Val
                    35                  40                  45
Cys Arg Ser Trp Ala Ala Trp Cys Lys Leu Asn Asn Arg Lys Trp Phe
                    50                  55                  60
Pro Ala Glu Pro Glu Asp Val Arg Asp Tyr Leu Leu Cys Leu Gln Ala
65                  70                  75                  80
Arg Gly Leu Ala Val Lys Thr Ile Gln Gln His Leu Gly Gln Leu Asn
```

```
            85                  90                  95
Met Leu His Arg Arg Ser Gly Leu Pro Arg Pro Ser Asp Ser Asn Ala
            100                 105                 110
Val Ser Leu Val Met Arg Arg Ile Arg Lys Glu Asn Val Asp Ala Gly
            115                 120                 125
Glu Arg Ala Lys Gln Ala Leu Ala Phe Lys Arg Thr Asp Phe Asp Gln
            130                 135                 140
Val Arg Ser Leu Met Glu Asn Ser Asp Arg Cys Gln Asp Ile Arg Asn
145                 150                 155                 160
Leu Ala Phe Leu Gly Ile Ala Tyr Asn Thr Leu Leu Arg Ile Ala Glu
                165                 170                 175
Ile Ala Arg Ile Arg Val Lys Asp Ile Ser Arg Thr Asp Gly Gly Arg
                180                 185                 190
Met Leu Ile His Ile Gly Arg Thr Lys Thr Leu Val Ser Thr Ala Gly
                195                 200                 205
Val Glu Lys Ala Leu Ser Leu Gly Val Thr Lys Leu Val Glu Arg Trp
            210                 215                 220
Ile Ser Val Ser Gly Val Ala Asp Asp Pro Asn Asn Tyr Leu Phe Cys
225                 230                 235                 240
Arg Val Arg Lys Asn Gly Val Ala Ala Pro Ser Ala Thr Ser Gln Leu
                245                 250                 255
Ser Thr Arg Ala Leu Glu Gly Ile Phe Glu Ala Thr His Arg Leu Ile
                260                 265                 270
Tyr Gly Ala Lys Asp Asp Ser Gly Gln Arg Tyr Gln Ala Trp Ser Gly
                275                 280                 285
His Ser Ala Arg Val Gly Ala Ala Arg Asp Met Ala Arg Ala Gly Val
            290                 295                 300
Ser Ile Pro Glu Ile Met Gln Ala Gly Gly Trp Thr Asn Val Asn Ile
305                 310                 315                 320
Val Met Asn Tyr Ile Arg Asn Leu Asp Ser Glu Thr Gly Ala Met Val
                325                 330                 335
Arg Leu Leu Glu Asp Gly Asp
                340

<210> SEQ ID NO 39
<211> LENGTH: 343
<212> TYPE: PRT
<213> ORGANISM: artificial sequence
<220> FEATURE:
<223> OTHER INFORMATION: mxoxox5

<400> SEQUENCE: 39

Met Ser Asn Leu Leu Thr Val His Gln Asn Leu Pro Ala Leu Pro Val
1               5                   10                  15
Asp Ala Thr Ser Asp Glu Val Arg Lys Asn Leu Met Ala Met Phe Arg
                20                  25                  30
Asp Arg Gln Ala Phe Ser Glu His Thr Trp Lys Met Leu Leu Ser Val
            35                  40                  45
Cys Arg Ser Trp Ala Ala Trp Cys Lys Leu Asn Asn Arg Lys Trp Phe
    50                  55                  60
Pro Ala Glu Pro Glu Asp Val Arg Asp Tyr Leu Leu Tyr Leu Gln Ala
65                  70                  75                  80
Arg Gly Leu Ala Val Lys Thr Ile Gln Gln His Leu Gly Gln Leu Asn
                85                  90                  95
Met Leu His Arg Gln Ser Gly Leu Pro Arg Pro Ser Asp Ser Asn Ala
```

-continued

```
            100                 105                 110
Val Ser Leu Val Met Arg Arg Ile Arg Lys Glu Asn Val Asp Ala Gly
        115                 120                 125
Glu Arg Ala Lys Gln Ala Leu Ala Phe Glu Arg Thr Asp Phe Asp Gln
    130                 135                 140
Val Arg Ser Leu Met Glu Asn Ser Asp Arg Cys Gln Asp Ile Arg Asn
145                 150                 155                 160
Leu Ala Phe Leu Gly Ile Ala Tyr Asn Thr Leu Leu Arg Ile Ala Glu
                165                 170                 175
Ile Ala Arg Ile Arg Val Lys Asp Ile Ser Arg Thr Asp Gly Gly Arg
            180                 185                 190
Met Leu Ile His Ile Gly Arg Thr Lys Thr Leu Val Ser Thr Ala Gly
        195                 200                 205
Val Glu Lys Ala Leu Ser Leu Gly Val Thr Lys Gln Val Glu Arg Trp
    210                 215                 220
Ile Ser Val Ser Gly Val Ala Asp Asp Pro Asn Asn Tyr Leu Phe Cys
225                 230                 235                 240
Arg Val Arg Lys Asn Gly Val Ala Ala Pro Ser Ala Thr Ser Gln Leu
                245                 250                 255
Ser Thr Arg Ala Leu Gly Gly Ile Phe Glu Ala Thr His Arg Leu Ile
            260                 265                 270
Tyr Gly Ala Lys Asp Asp Ser Gly Gln Arg Tyr Leu Ala Trp Ser Gly
        275                 280                 285
His Ser Ala Arg Val Gly Ala Ala Arg Asp Met Ala Arg Ala Gly Val
    290                 295                 300
Ser Ile Pro Glu Ile Met Gln Ala Gly Gly Trp Ser Asn Val Asn Ile
305                 310                 315                 320
Val Met Asn Tyr Ile Arg Asn Leu Asp Ser Glu Thr Gly Ala Met Val
                325                 330                 335
Arg Leu Leu Glu Asp Gly Asp
            340

<210> SEQ ID NO 40
<211> LENGTH: 343
<212> TYPE: PRT
<213> ORGANISM: artificial sequence
<220> FEATURE:
<223> OTHER INFORMATION: mxoxox6

<400> SEQUENCE: 40

Met Ser Asn Leu Leu Thr Val His Gln Asn Leu Pro Ala Leu Pro Val
1               5                   10                  15
Asp Ala Thr Ser Asp Glu Val Arg Lys Asn Leu Met Asp Met Phe Arg
            20                  25                  30
Asp Arg Gln Ala Phe Ser Glu His Thr Trp Lys Met Leu Leu Ser Val
        35                  40                  45
Cys Arg Ser Trp Ala Ala Trp Cys Lys Leu Asn Asn Arg Lys Trp Phe
    50                  55                  60
Pro Ala Glu Pro Glu Asp Val Arg Asp Tyr Leu Leu Tyr Leu Gln Ala
65                  70                  75                  80
Arg Gly Leu Ala Val Lys Thr Ile Gln Gln His Leu Gly Gln Leu Asn
                85                  90                  95
Met Leu His Arg Arg Ser Gly Leu Pro Arg Pro Ser Asp Ser Asn Ala
            100                 105                 110
Val Ser Leu Val Met Arg Arg Ile Arg Lys Glu Asn Val Asp Ala Gly
```

```
            115                 120                 125
Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
                180                 185                 190

Met Leu Ile His Ile Gly Arg Thr Lys Thr Leu Val Ser Thr Ala Gly
            195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Gly Gly Ile Phe Glu Ala Thr His Arg Leu Ile
            260                 265                 270

Tyr Gly Ala Lys Asp Asp Ser Gly Gln Arg Tyr Gln Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Ser Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 41
<211> LENGTH: 13
<212> TYPE: DNA
<213> ORGANISM: artificial sequence
<220> FEATURE:
<223> OTHER INFORMATION: loxP
<220> FEATURE:
<221> NAME/KEY: misc_feature
<222> LOCATION: (6)..(7)
<223> OTHER INFORMATION: nn is either TT, TG, GT, GG, TC, CC, or AA

<400> SEQUENCE: 41
ataacnncgt ata                                                      13

<210> SEQ ID NO 42
<211> LENGTH: 13
<212> TYPE: DNA
<213> ORGANISM: artificial sequence
<220> FEATURE:
<223> OTHER INFORMATION: loxK2

<400> SEQUENCE: 42
ataacaacgt ata                                                      13

<210> SEQ ID NO 43
<211> LENGTH: 13
<212> TYPE: DNA
<213> ORGANISM: artificial sequence
<220> FEATURE:
<223> OTHER INFORMATION: loxK1
```

```
<400> SEQUENCE: 43 ataccttttgt ata                                                    13

<210> SEQ ID NO 44
<211> LENGTH: 34
<212> TYPE: DNA
<213> ORGANISM: artificial sequence
<220> FEATURE:
<223> OTHER INFORMATION: loxP

<400> SEQUENCE: 44
ataacttcgt atataccttt ctatagcaag ttat                              34

<210> SEQ ID NO 45
<211> LENGTH: 34
<212> TYPE: DNA
<213> ORGANISM: artificial sequence
<220> FEATURE:
<223> OTHER INFORMATION: loxK2

<400> SEQUENCE: 45
ataacaacgt atataccttt ctatagcttg ttat                              34

<210> SEQ ID NO 46
<211> LENGTH: 34
<212> TYPE: DNA
<213> ORGANISM: artificial sequence
<220> FEATURE:
<223> OTHER INFORMATION: loxK1

<400> SEQUENCE: 46 ataccttttgt atataccttt ctatagaaag gtat                             34

<210> SEQ ID NO 47
<211> LENGTH: 34
<212> TYPE: DNA
<213> ORGANISM: artificial sequence
<220> FEATURE:
<223> OTHER INFORMATION: loxK2 'GG'

<400> SEQUENCE: 47
ataacggcgt atataccttt ctatagcccg ttat                              34

<210> SEQ ID NO 48
<211> LENGTH: 34
<212> TYPE: DNA
<213> ORGANISM: artificial sequence
<220> FEATURE:
<223> OTHER INFORMATION: loxK2 'CC'

<400> SEQUENCE: 48
ataaccccgt atataccttt ctatagcggg ttat                              34

<210> SEQ ID NO 49
<211> LENGTH: 34
<212> TYPE: DNA
<213> ORGANISM: artificial sequence
<220> FEATURE:
<223> OTHER INFORMATION: loxK2 'TC'

<400> SEQUENCE: 49
ataactccgt atataccttt ctatagcgag ttat                              34

<210> SEQ ID NO 50
```

```
<211> LENGTH: 34
<212> TYPE: DNA
<213> ORGANISM: artificial sequence
<220> FEATURE:
<223> OTHER INFORMATION: loxK2 'GT'

<400> SEQUENCE: 50
ataacgtcgt atataccttt ctatagcacg ttat                                34

<210> SEQ ID NO 51
<211> LENGTH: 34
<212> TYPE: DNA
<213> ORGANISM: artificial sequence
<220> FEATURE:
<223> OTHER INFORMATION: loxK2 'TG'

<400> SEQUENCE: 51
ataactgcgt atataccttt ctatagccag ttat                                34

<210> SEQ ID NO 52
<211> LENGTH: 34
<212> TYPE: DNA
<213> ORGANISM: artificial sequence
<220> FEATURE:
<223> OTHER INFORMATION: LoxP

<400> SEQUENCE: 52
ataacttcgt ataatgtatg ctatacgaag ttat                                34

<210> SEQ ID NO 53
<211> LENGTH: 34
<212> TYPE: DNA
<213> ORGANISM: artificial sequence
<220> FEATURE:
<223> OTHER INFORMATION: LoxK1

<400> SEQUENCE: 53
gagcctttgt atataccttt ctatacaaag gctt                                34

<210> SEQ ID NO 54
<211> LENGTH: 34
<212> TYPE: DNA
<213> ORGANISM: artificial sequence
<220> FEATURE:
<223> OTHER INFORMATION: loxK2

<400> SEQUENCE: 54
gatacaacgt atataccttt ctatacgttg tatt                                34

<210> SEQ ID NO 55
<211> LENGTH: 64
<212> TYPE: DNA
<213> ORGANISM: artificial sequence
<220> FEATURE:
<223> OTHER INFORMATION: Gene

<400> SEQUENCE: 55
gctagcgaat tcgagcttcg gtacccgggg atcctctaga gtcgacctgc aggcatgcaa    60
gctt                                                                 64

<210> SEQ ID NO 56
<211> LENGTH: 33
<212> TYPE: DNA
<213> ORGANISM: artificial sequence
<220> FEATURE:
<223> OTHER INFORMATION: oligonucleotide
```

```
<400> SEQUENCE: 56
agcttggagg ctatcatgtc gaccaagcta gca                              33

<210> SEQ ID NO 57
<211> LENGTH: 33
<212> TYPE: DNA
<213> ORGANISM: artificial sequence
<220> FEATURE:
<223> OTHER INFORMATION: oligonucleotide

<400> SEQUENCE: 57
gatctgctag cttggtcgac atgatagcct cca                              33

<210> SEQ ID NO 58
<211> LENGTH: 35
<212> TYPE: DNA
<213> ORGANISM: artificial sequence
<220> FEATURE:
<223> OTHER INFORMATION: oligonucleotide

<400> SEQUENCE: 58
gatctgatat ctgcggccgc tgacgtgact cgagt                            35

<210> SEQ ID NO 59
<211> LENGTH: 35
<212> TYPE: DNA
<213> ORGANISM: artificial sequence
<220> FEATURE:
<223> OTHER INFORMATION: oligonucleotide

<400> SEQUENCE: 59
ctagactcga gtcacgtcag cggccgcaga tatca                            35

<210> SEQ ID NO 60
<211> LENGTH: 13
<212> TYPE: DNA
<213> ORGANISM: artificial sequence
<220> FEATURE:
<223> OTHER INFORMATION: oligonucleotide

<400> SEQUENCE: 60
gaagttccta ttc                                                    13

<210> SEQ ID NO 61
<211> LENGTH: 8
<212> TYPE: DNA
<213> ORGANISM: artificial sequence
<220> FEATURE:
<223> OTHER INFORMATION: oligonucleotide

<400> SEQUENCE: 61 tctagaaa                                                           8

<210> SEQ ID NO 62
<211> LENGTH: 13
<212> TYPE: DNA
<213> ORGANISM: artificial sequence
<220> FEATURE:
<223> OTHER INFORMATION: oligonucleotide

<400> SEQUENCE: 62
gtataggaac ttc                                                    13

<210> SEQ ID NO 63
```

```
<211> LENGTH: 27
<212> TYPE: DNA
<213> ORGANISM: artificial sequence
<220> FEATURE:
<223> OTHER INFORMATION: oligonucleotide

<400> SEQUENCE: 63
gaagttccta ttccgaagtt cctattc                               27

<210> SEQ ID NO 64
<211> LENGTH: 6
<212> TYPE: DNA
<213> ORGANISM: artificial sequence
<220> FEATURE:
<223> OTHER INFORMATION: oligonucleotide

<400> SEQUENCE: 64 tctaga                                                       6

<210> SEQ ID NO 65
<211> LENGTH: 13
<212> TYPE: DNA
<213> ORGANISM: artificial sequence
<220> FEATURE:
<223> OTHER INFORMATION: oligonucleotide

<400> SEQUENCE: 65
gaagttcata ttc                                              13

<210> SEQ ID NO 66
<211> LENGTH: 13
<212> TYPE: DNA
<213> ORGANISM: artificial sequence
<220> FEATURE:
<223> OTHER INFORMATION: oligonucleotide

<400> SEQUENCE: 66
gtatatgaac ttc                                              13

<210> SEQ ID NO 67
<211> LENGTH: 13
<212> TYPE: DNA
<213> ORGANISM: artificial sequence
<220> FEATURE:
<223> OTHER INFORMATION: oligonucleotide

<400> SEQUENCE: 67
gaagttacta ttc                                              13

<210> SEQ ID NO 68
<211> LENGTH: 13
<212> TYPE: DNA
<213> ORGANISM: artificial sequence
<220> FEATURE:
<223> OTHER INFORMATION: oligonucleotide

<400> SEQUENCE: 68
gtatagtaac ttc                                              13
```

METHOD FOR SELECTING RECOMBINASE VARIANTS WITH ALTERED SPECIFICITY

CROSS-REFERENCE TO RELATED APPLICATIONS

This application claims benefit of U.S. Provisional Application No. 60/127,977, filed Apr. 6, 1999. Application Ser. No. 60/127,977, filed Apr. 6, 1999, is hereby incorporated herein by reference.

BACKGROUND OF THE INVENTION

Recombinases, integrases and resolvases (collectively referred to herein as recombinases) mediate the site-specific recombination of DNA. These recombinases were first identified in phage that integrate into host chromosomes. Such integration allows the phage to remain latent in the cell as a prophage.

Site-specific recombinases catalyze conservative DNA rearrangements at specific target sequences. The 38 kDa Cre recombinase (cyclization recombination), derived from the bacteriophage P1, is a well characterized and widely used enzyme of the Integrase family (reviewed by Sauer, Methods, 14:381–392 (1998)). Cre plays two essential roles in the life cycle of P1: First, it provides a host-independent mechanism for P1's genome cyclization after infection, which can be important when the recombination system of the host is compromised. Second, Cre resolves dimerized P1 prophage plasmids to guarantee proper segregation during cell division.

Cre acts on a 34 bp sequence located on both ends of the linear P1 genome, that is called loxP (locus of crossover of P1; Sternberg and Hamilton, J. Mol. Biol., 150:467–486 (1981)), loxP consists of two 13 bp inverted repeats flanking a non-palindromic 8 bp core that defines the assigned direction of the sequence (as shown on the upper part of FIG. 1). Depending on this direction recombination catalyzed by Cre leads to excision of insertion of DNA flanked by loxP sites oriented in the same direction (indicated by loxP$^2$), but leads to inversion when oriented in the opposite direction (FIG. 2).

In general, Cre-recombination involves the following four events: (i) DNA binding, (ii) synapsis (as defined below), (iii) cleavage, and (iv) strand exchange. To study this process in greater detail, mutants defective for each step have been isolated using several screening procedures (Wierzbicki et al., J. Mol. Biol., 195:785–794 (1987)). In addition, the crystal structure of Cre complexed with an artificial suicide substrate has been recently resolved, providing additional insights into site-specific recombination (Guo et al., Nature, 389:40–46 (1997)). From these studies, the following has been proposed: Four interacting Cre molecules are necessary for recombination between two lox sites, with each enzyme binding one inverted repeat plus the two outermost bp of the non-symmetric core region (DNA binding). This leads to the formation of a clamp, allowing DNA contacts in the major, as well as in the minor groove. In the step referred to as synapsis, the two lox sites with the bound Cre molecules, are aligned in parallel leading to an approximate 100° bending of the DNA. In the following step of strand cleavage, one of the two Cre molecules on each lox site causes a staggered cut in the core region, as indicated by the vertical arrows in FIG. 1. This leads to a 6 bp 5' overhang and a covalent 3' phosphotyrosine linkage between the catalytic residue tyrosine 324 of Cre and the guanine (position 4) at the cleaving site of loxP. The created phosphotyrosine intermediate is thought to provide the energy for the reaction, thereby explaining why Cre does not require an external energy source. In the next step, the first strand is exchanged between the two nicked lox sites, creating an intermediate, named Holliday structure (Sigal and Alberts, J. Mol. Biol., 71:789–793 (1972)). Of note, this first strand exchange is asymmetric, since the bottom strand (FIG. 1) is always exchanged first (Hoess et al., Proc. Natl. Acad. Sci. USA, 84:6840–6844 (1987)). During the final step, the second strand is exchanged and Cre released from its substrate.

Because of the simplicity and the ability of Cre to function in yeast and mammalian cells (Sauer, B., Mol. Cell. Biol., 7:2087–2096 (1987); Sauer and Henderson, Proc. Natl. Acad. Sci. USA, 85:5166–5170 (1988), Sauer and Henderson, Nucl. Acids Res., 17:147–161 (1989), and Sauer and Henderson, The New Biologist, 2:441–449 (1990), Cre assisted site-specific recombination has become an important tool for efficient, specific, and conditional manipulations of eukaryotic genomes (Lakso et al., Proc. Natl Acad. Sci. USA, 89:6232–6236 (1992)): Kilby et al., Genet., 9:413–421 (1993); Sauer, B., Meth. enzymol., 225:890–900 (1993); Kühn et al., Science, 269:1427–1429 (1995); Metzger et al., Pro. Natl. Acad. Sci. USA, 92:6691–6995 (1995).

However, there are some inconveniences for the successful use of Cre-related technologies, that include the following: (i) lox sites need to be introduced by homologous recombination at the desired region into the genome before Cre can be used, (ii) the frequency of correct site-specific recombination due to Cre expression is not 100%, and consequently, (iii) selectable markers are necessary in most strategies involving Cre for genome manipulation in higher eukaryotes. These markers, e.g. neo or TK, may introduce problems in subsequent studies, particular in those related to animal development. The number of available selectable markers that can be used in limited also. Additional site-specific recombinases that also function efficiently in eukaryotic systems, but recognize different sites from lox would be helpful. Similar inconveniences limit the usefulness of other recombinases.

Therefore, it is an object of the present invention to provide method of identifying variant recombinases that can mediate recombination between variant recombination sites.

It is another object of the present invention to provide variant recombinases that can mediate recombination between variant recombination sites.

It is another object of the present invention to provide a method of recombining nucleic acid molecules in vitro and in vivo.

It is another object of the present invention to provide Cre variants that recognize variant recombination sites.

BRIEF SUMMARY OF THE INVENTION

Disclosed is a method for identifying variant forms of recombinases that can mediate recombination between variant recombination sites. The method involves producing mutant recombinases and testing the mutant recombinases with specially designed constructs. The constructs contain variant recombination sites that are not recognized by non-mutant recombinase but will undergo recombination in the presence of a mutant recombinase with altered specificity. Recombination at the variant recombination sites can be monitored or detected by any suitable means. It is preferred that recombination is detected by screening or selection based on the expression or lack of expression of a reporter gene. This can be accomplished by using constructs containing a reporter gene associated with the variant recombination sites such that the reporter gene is rearranged or deleted, or a spacer sequence interrupting the reporter gene is rearranged or deleted, as a result of recombination at the recombination sites. Recombination of such constructs will result in a loss of expression of the reporter gene, where the construct contained a functional reporter gene, or in a gain in expression of the reporter gene, where the construct contained a non-functional reporter gene.

The disclosed method also involves determining whether a variant recombinase retains the ability to mediate recombination at recombination sites recognized by non-variant recombinase. This can be accomplished by using constructs containing recombination sites recognized by non-variant recombinase. Recombination at these recombination sites can be monitored or detected by any suitable means. It is preferred that recombination is detected by screening or selection based on the expression or lack of expression of a reporter gene. This can be accomplished by using constructs containing a reporter gene associated with the recombination sites recognized by non-variant recombinase such that the reporter gene is rearranged or deleted, or a spacer sequence interrupting the reporter gene is rearranged or deleted, as a result of recombination at the recombination sites. Recombination of such constructs will result in a loss of expression of the reporter gene, where the construct contained a functional reporter gene, or in a gain in expression of the reporter gene, where the construct contained a non-functional reporter gene.

When variant recombinases are tested for activity on both variant recombination sites and recombination sites recognized by non-variant recombinase in the same system or at the same time, it is preferred that two different reporter genes, which can be separately detected or monitored, be used. In this case, the first reporter gene can be associated with the variant recombination sites and the second reporter gene can be associated with recombination sites recognized by non-variant recombinase.

Recombination between two recombination sites require (1) that the recombinase recognize the sites as recombination sites, and (2) that the sequences of the two sites is sufficiently similar. It has been discovered that recombination between two recombination sites (both of which are recognized by a recombinase) can be substantially reduced or prevented by using different compatibility sequences for the recombination sites (the recognition sequences can also differ if the recombinase can recognize different sequences). Thus, it is also preferred that the variant recombination sites be made incompatible with the recombination sites recognized by non-variant recombinase by using different compatibility sequences for the two sets of recombination sites.

Compatibility sequences in a recombination site are those sequences in the recombination site, other than the sequences required for recognition of the site by the recombinase, that must be similar in a pair of recombination sites for recombination to occur between them. Many recombination sites contain repeats of a characteristic sequence separated by spacer sequences. In such recombination sites, the spacer sequences are generally compatibility sequences and the repeats (or parts of the repeats) are recognition sequences. Recombinases require specific recognition sequences but allow wide variation in compatibility sequences. Thus, recombination sites that are recognized by a given recombinase but are incompatible with each other can be readily designed using the disclosed principles.

Also disclosed are variant recombinases made or identified by the disclosed method that have broadened specificity for the site of recombination. Specifically, the disclosed variants mediate recombination between sequences other than recombination sites on which the wild type recombinase is active. In general, the disclosed recombinase variants can mediate efficient recombination between recombination sites that wild type recombinase can act on (referred to as wild type recombination sites), between variant recombination sites not efficiently utilized by wild type recombinase (referred to as variant recombination sites), and between a wild type recombination site and a variant recombination site.

Also disclosed are methods of recombining nucleic acids using the disclosed variant recombinases. For example, the disclosed variant recombinases can be used in any method or technique where wild type recombinases can be used. In addition, the disclosed variant recombinases allow different alternative recombination to be performed since the variant recombinases can allow much more efficient recombination between wild type recombination sites and variant recombination sites. Control of such alternative recombination can be used to accomplish more sophisticated sequential recombinations to achieve results not possible with wild type recombinases. The disclosed variant recombinases also allow recombination at specific genomic sites without the need to first introduce a recombination site.

Also disclosed are variants of Cre recombinase that have broadened specificity for the site of recombination. Specifically, the disclosed variants mediate recombination between sequences other than the loxP sequence and other lox site sequences on which wild type Cre recombinase is active. In general, the disclosed Cre variants mediate efficient recombination between lox sites that wild type Cre can act on (referred to as wild type lox sites), between variant lox sites not efficiently utilized by wild type Cre (referred to as variant lox sites), and between a wild type lox site and a variant lox site. Also disclosed are methods of recombining nucleic acids using the disclosed Cre variants. For example, the disclosed Cre variants can be used in any method or technique where Cre recombinase (or other, similar recombinases such as FLP) can be used. In addition, the disclosed Cre variants allows different alternative recombinations to be performed since the Cre variants allow much more efficient recombination between wild type lox sites and variant lox sites. Control of such alternative recombination can be used to accomplish more sophisticated sequential recombinations to achieve results not possible with wild type Cre recombinase.

BRIEF DESCRIPTION OF THE DRAWINGS

FIG. 1 is a comparison of three different lox sites. loxP (SEQ ID NO: 52) is the original recombination site for Cre recombinase. loxK1 and loxK2 (SEQ ID NO: 53–54) are variant lox sites.

FIGS. 8A and 8B are a diagram of the construction of selection plasmids pBS583 and pBS584.

FIG. 12A shows examples of deletion constructs (flanked and interrupted). FIG. 12B shows examples of inverted constructs. FIG. 12C shows examples of constructs that combine through recombination to reconstitute an intact gene.

FIG. 15 is a table comparing recombination frequencies in vitro obtained with a variety of lox sites altered at positions 11 and 12. (SEQ ID NO:41).

DETAILED DESCRIPTION OF THE INVENTION

Figure 2:
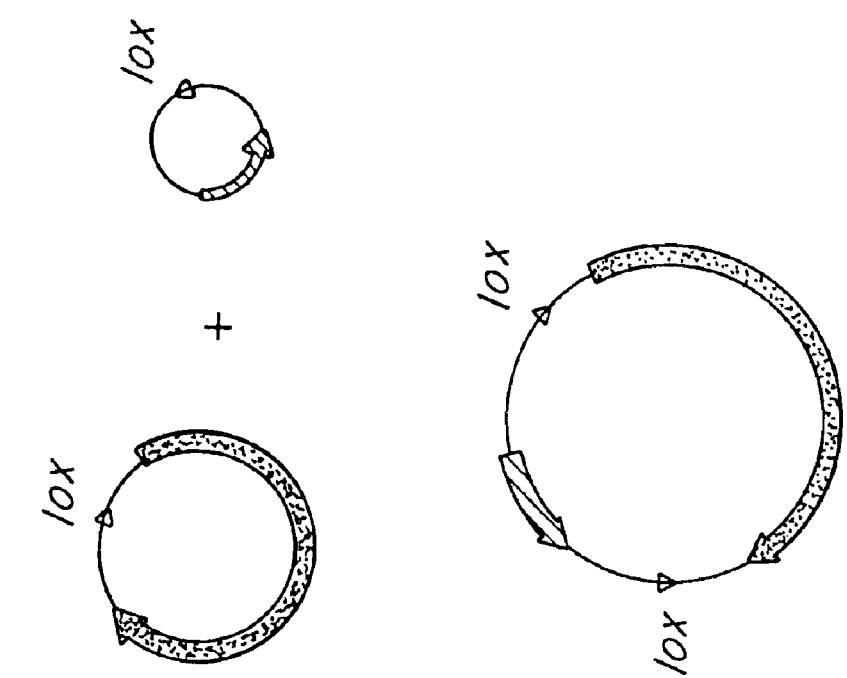
FIG. 2 is a diagram of two different forms of construct and the resulting recombination products.
Figure 2:
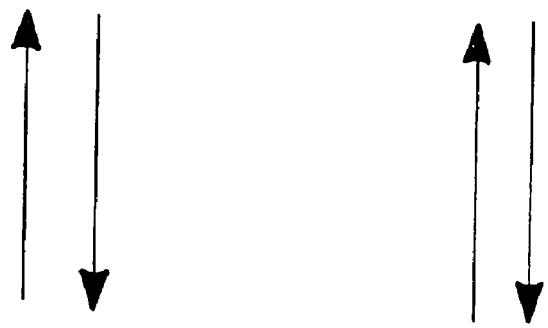
Figure 2:
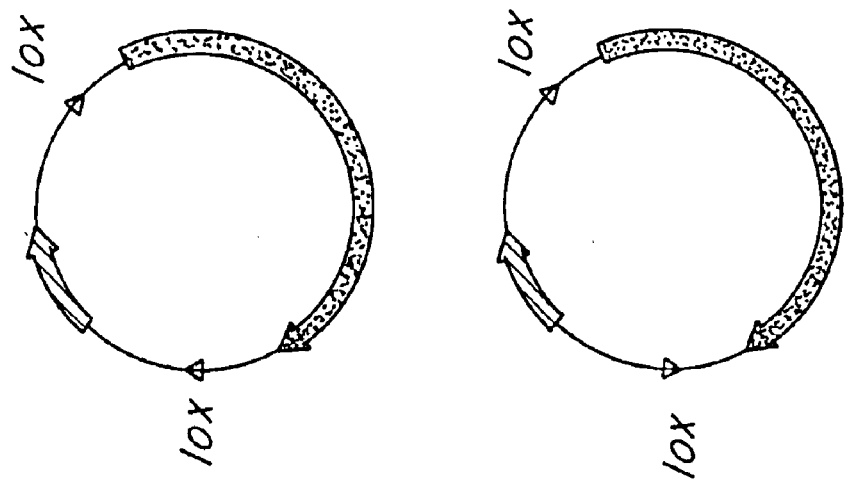
Figure 3:
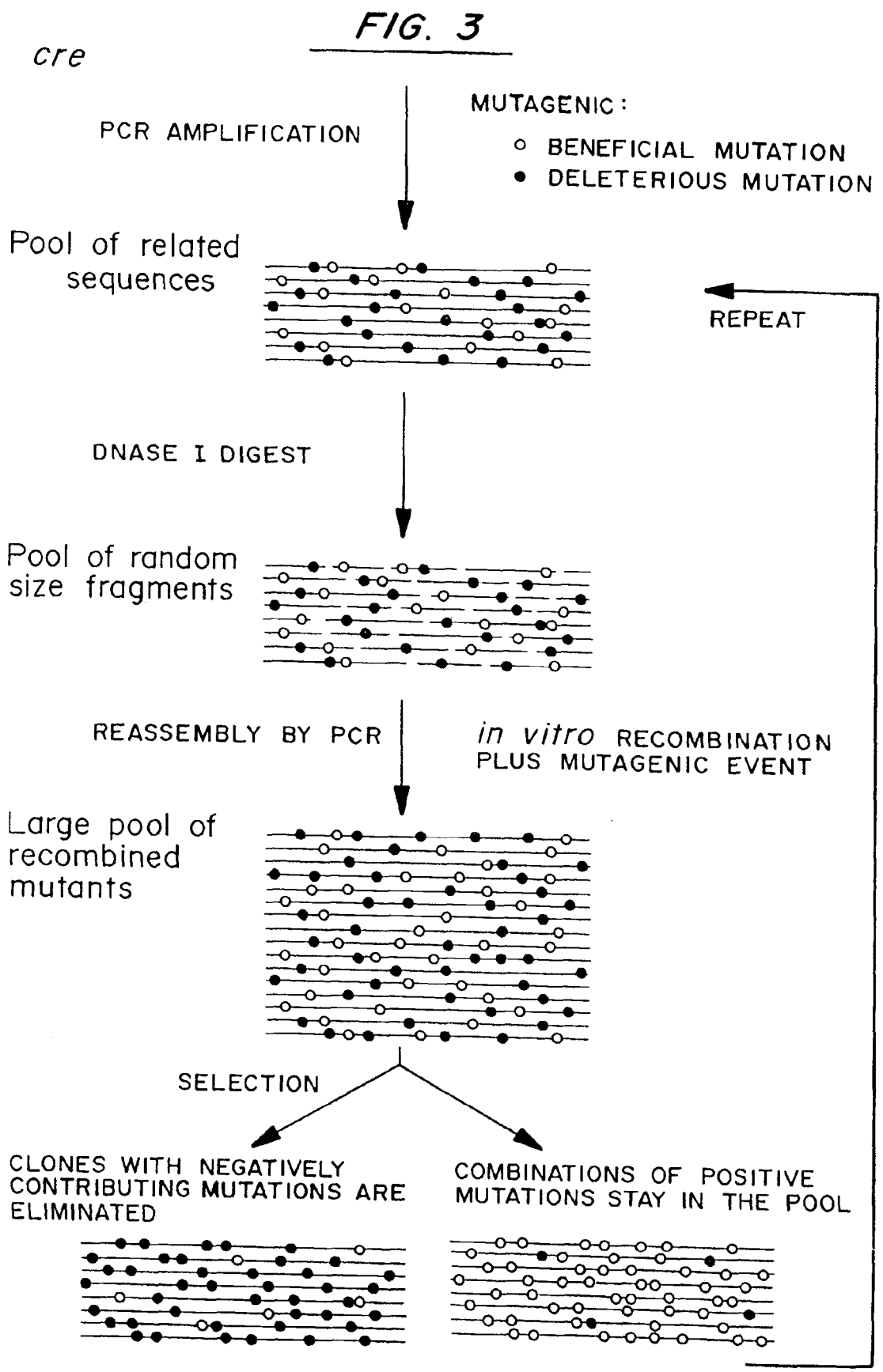
FIG. 3 is a diagram of an example of a random mutagenesis using DNA shuffling.

Disclosed is a method for identifying variant forms of recombinases that can mediate recombination between variant recombination sites. The method involves producing mutant recombinases and testing the mutant recombinases with specifically designed constructs. The constructs contain variant recombination sites that are not recognized by non-mutant recombinase but will undergo recombination in the presence of a mutant recombinase with altered specificity. The disclosed method also involves determining whether a variant recombinase retains the ability to mediate recombination at recombination sites recognize by non-variant recombinase.

When variant recombinases are tested for activity on both variant recombination sites and recombination sites recognized by non-variant recombinase in the same system or at the same time, it is preferred that two different reporter genes which can be separately detected or monitored be used. In this case, a first reporter gene can be associated with the variant recombination sites and as second reporter gene can be associated with recombination sites recognized by non-variant recombinase. It is also preferred that the variant recombination sites be made incompatible with the recombination sites recognized by non-variant recombinase by using different compatibility sequences for the two set of recombination sites. This allows separate assessment of the ability of a variant recombinase to mediate recombination between variant recombination sites and recombination sites recognized by non-variant recombinase.

Also disclosed are variant recombinases made or identified by the disclosed method that have broadened specifically for the site of recombination. Also disclosed are methods of recombining nucleic acids using the disclosed variant recombinases. For example, the disclosed variant recombinases can be used in any method or technique where wild type recombinases can be used. In addition, the disclosed variant recombinases allow different alternative recombinations to be performed since the variant recombinases can allow much more efficient recombination between wild type recombination sites and variant recombination sites. Control of such alternative recombination can be used to accomplish more sophisticated sequential recombinations to achieve results not possible with wild type recombinases.

Also disclosed are variants of Cre recombinase that have broadened specificity for the site of recombination. Specifically, the disclosed variants mediate recombination between sequences other than the loxP sequence and other lox site sequences on which wild type Cre recombinase is active Preferred forms of the disclosed Cre variants have the amino acid sequences SEQ ID NO:1 (top sequence, Table 11) altered by one or more amino acid substitutions, deletions, or insertions, where the glutamic acid at amino acid 262 has been substituted with an amino acid other than glutamic acid, and where the Cre variant recognize (that is, mediates recombination at) a variant lox recombination site. Useful Cre variants include proteins that recognize a variant lox recombination site and have the amino acid sequence SEQ ID NO:1 altered by substitution of the glutamic acid at amino acid 262 with an amino acid other than glutamic acid and one or more of the following amino acid substitutions: isoleucine at amino acid 16, alanine at amino acid 29, glutamine at amino acid 101, glycine at amino acid 138, asparagine at amino acid 189, serine at amino acid 198, glutamine at amino acid 220, glutamine at amino acid 223, isoleucine at amino acid 277, glycine at amino acid 254, arginine at amino acid 255, glutamine at amino acid 284, leucine at amino acid 307, and serine at amino acid 316. Preferred amino acid substitutions at amino acid position 262 include alanine, tryptophan, or glycine.

Examples of preferred Cre variants include proteins having the amino acid sequences SEQ ID NO:1 altered by substitutions E262G and D189N; proteins having the amino acid sequence SEQ ID NO:1 altered by substitutions E262G and T316S; proteins having the amino acid sequence SEQ ID NO:1 altered by substitutions E262G and D29A; proteins having the amino acid sequence SEQ ID NO:1 altered by substitutions E262G, V16I, D189N, G198S, R223Q, Q255R, and P307L; proteins having the amino acid sequences SEQ ID NO:1 altered by substitution E262G; proteins having the amino acid sequence SEQ ID NO:1 altered by substitution E262A; and proteins having the amino acid sequence SEQ ID NO:1 altered by substitution E262W. The substitutions above are listed using the convention where the first letter is the original amino acid (in single letter amino acid code), the number is the amino acid position in the protein (in this case, using the positions of wild type Cre (SEQ ID NO:1)), and the last letter is the new amino acid (in single letter amino acid code). All of these Cre variants recognize both wild type lox sites and variant lox sites with an inverted repeat sequence NNNACNNCG-TATA (SEQ ID NO:2).

The disclosed Cre variants recognize variant lox recombination sites. Preferred variant lox sites are variant lox sites recognized by the Cre variant but not recognized by wild type Cre. Examples of useful variant lox sites include sites having two 13 base pair inverted repeats flanking 8 base pairs, where one of the inverted repeats has the sequence NNNACNNCGTATA (SEQ ID NO:2); sites having the sequence $N_1N_2N_3ACN_4N_5CGTATANNNNNNNN$ TATACGN$_5$'N$_4$'GTN$_3$'N$_2$'N$_1$' (SEQ ID NO:3), where N$_1$', N$_2$', N$_3$', N$_4$', and N$_5$' are complementary to $N_1$, $N_2$, $N_3$, $N_4$, and $N_5$, respectively; sites having the sequence $N_1N_2N_3ACN_4N_5CGTATANNNNNNNNTATACGN_5$'N$_4$' GN$_3$'N$_2$'N$_1$' (SEQ ID NO:3), where $N_4N_5$ are AA, TC, GT, TG, GG, or CC; and sites having the sequence GATA-CAACGTATATACCTTTCTATACGTTGTATA (SEQ ID NO:4).

Also disclosed is a method for producing site-specific recombination of DNA in cells using the disclosed Cre variants. DNA sequences comprising first and second lox sites are introduced into cells and contacted with a Cre variant, thereby producing recombination at the lox sites. As with wild type Cre, the location and orientation of the lox sites determines the nature of the recombination.

As used herein, the expression "site-specific recombination" refers to three different types of recombination events:

1. deletion of a pre-selected DNA segment flanked by recombination sites,
2. inversion of the nucleotide sequence of a pre-selected DNA segment flanked by recombination sites, and
3. reciprocal exchange of DNA segments proximate to recombination sites located on different DNA molecules.

It is to be understood that this reciprocal exchange of DNA segments can result in an integration event if one or both of the DNA molecules are circular. "Nucleic acid segment" refers to a linear segment of single- or double-stranded nucleic acid, which can be derived from any source. The segment may be a fragment consisting of the segment or a segment within a larger nucleic acid fragment or molecule. The expression "nucleic acid in eukaryotic cells" includes all nucleic acid present in eurkaryotic cells. The expression "nucleic acid in yeast" includes all nucleic acid present in yeast cells. "DNA segment" refers to a linear segment of single- or double-stranded deoxyribonucleic acid (DNA), which can be derived from any source. The expression "DNA in eukaryotic cells" includes all DNA present in eukaryotic cells. The expression "DNA in yeast" includes all DNA present in yeast cells. As used herein, a "gene" is intended to mean a DNA segment which is normally regarded as a gene by those skilled in the art. The expression "regulatory molecule" refers to a polymer of ribonucleic acid (RNA) or a polypeptide which is capable of enhancing or inhibiting expression of gene.

"Regulatory nucleotide sequence," as used herein, refers to a nucleotide sequence located proximate to a gene whose transcription is controlled by the regulatory nucleotide sequence in conjunction with the gene expression apparatus of the cell. Generally, the regulatory nucleotide sequence is located 5' to the gene. The expression "nucleotide sequence" refers to a polymer of DNA or RNA, which can be single- or double-stranded, optionally containing synthetic, non-natural, or altered nucleotides capable of incorporation into DNA or RNA polymers. As used herein, a "regulatory nucleotide sequence" can include a promoter region, as that term is conventionally employed by those skilled in the art. A promoter region can include an association region recognized by an RNA polymerase, one or more regions which control the effectiveness of transcription initiation in response to physiological conditions, and a transcription initiation sequence. "Gene product" refers to a polypeptide resulting from transcription, translation, and, optionally, post-translational processing of a selected DNA segment.

MATERIALS

A. Recombinases

Recombinases suitable for use in the disclosed method include any enzyme that medicare recombination at specific sites. This includes enzymes identified as recombinases as well as other enzymes that function to produce recombination such as integrases and resolvases. As used herein, recombination at specific sites does not refer only to recombination at completely defined sequences. Rather, a recombinase is considered to mediate recombination at specific sites when the sites of recombination are limited in some way by sequence. For example, wild type Cre recombinase mediates recombination between sites having the sequence $N_1N_2N_3$ACTTCGTATANNNNNNNT ATACGAA GTN$_3$'N$_2$'N$_1$' (SEQ ID NO: 5), which includes both specific and non-specific sequences. The sequences ACTTCGTATA (bases 4–13% SEQ ID NO:5) and TATACGAAGT (bases 22–31 of SEQ ID NO:7) (an inverted repeat of the first sequence) are recognized by the Cre recombinase. The non-specific sequences (positions with "N" in the recognition sequence), although not limited in sequence, must be compatible with the non-specific sequences of the partner recombination site in order for recombination to be efficient. The recombination sites need not have any particular number of specific nucleotides. All that is required is some constraint on the sequence of the site such that the recombinase is limited to recombination at some set of sites.

Examples of recombinases that can be used in the disclosed method include Cre recombinase, FLP recombinase, Beta recombinase of pSM19035 (Diaz et al., *J Biol Chem* 274: 6634–6640 (1999)), Int recombines (Nunes-Döby et al., *Nucleic Acids Res.* 26:391–406 (1998)), and resolvases (Hallet et al., FEMS *Microbiol Rev.* 21: 157–178 (1997); Oram et al., *Curr Biol.* 5: 1106–1109 (1995); Mondragon, *Structure* 3: 755–758 (1995)).

B. Recombination Sites

Recombination sites are locations within a nucleic acid where recombination mediated by a recombinase takes place. Recombination sites generally include specific sequences, referred to as recognition sequences, through which the recombinase recognizes a given nucleotide sequence as a recombination site. Different recombinases generally recognize different recognition sequences. Recombination between two recombination sites requires (1) that the recombinase recognize the sites as recombination sites, and (2) that the sequences of the two sites are sufficiently similar. It has been discovered that recombination between two recombination sites (both of which are recognized by a recombinase) can be substantially reduced or prevented by using different compatibility sequences for the recombination sites (the recognition sequences can also differ if the recombinase can recognize different sequences). Thus, it is also preferred that the variant recombination sites be made incompatible with the recombination sites recognized by non-variant recombinase by using different compatibility sequences for the two sets of recombination sites. Compatibility sequences in a recombination site are those sequences in the recombination site, other than the sequences required for recognition of the site by the recombinase, that must be similar in a pair of recombination sites for recombination to occur between them. Generally, recombinases require specific recognition sequences but allow wide variation in compatibility sequences. Thus, recombination sites that are recognized by a given recombinase but are incompatible with each other can be readily designed using the disclosed principles.

It should be understood that, for a given recombinase site or for a given recombinase, whether a given base position in the recombination site is a recognition sequence base or a compatibility sequence base may depend on other sequences in the recombination site. For example, a particular base may function as a compatibility sequence base in a recombination site having one sequence while the same base may function as a recognition sequence base in a recombination site having a different sequence. It should also be understood that recognition sequences and compatibility sequences do not necessarily occur in blocks within a recombination site. That is, recognition sequence base and compatibility sequence bases may be interspersed in a given recombination site. As discussed below, what is and is not a recognition sequence or a compatibility sequence in a given recombination site is determined functionally.

The disclosed variant recombination sites and the variant recombinases the can act on them allow more freedom in the selection of sites of recombination. In particular, the disclosed variant recombinases can allow amino acid changes in a protein of interest while retaining the ability to recombine at a given site.

1. Recognition Sequences

Recognition sequences are regions within a recombination site that must have a specific sequence, or defined range of sequences, for the cognate recombinase to recognize the recombination site. Recognition sequences in a recombination site need not be contiguous. Thus, required nucleotides dispersed in a recombination site are collectively considered recognition sequences. Nucleic acid segments can be said to have a defined range of sequences when every nucleotide position in the nucleic acid segment(s) is limited to one, two, or three nucleotide bases. That is, so long as a nucleotide position cannot have one of the possible nucleotide bases, that position has a defined range of sequence. For example, a nucleotide sequence ATRVBYGC (SEQ ID NO:6) has a defined range of sequences since each nucleotide position has at least one limitation. Standard nonmenclature for nucleic acid sequences is used herein. Thus, in this example, R represents A or G; V represents A, C, or G; B represents C, G, or T; and Y represents C or T.

Recognition sequences for recombinases are known or can be determined through routine analysis. In general, recognition sequences can be determined by varying the sequence of recombination sites and determining if recombination between the sites can still occur. For this purpose, the pair of sites to be recombined should be identical. That is, the same sequence changes should be made to both sites. This eliminates any incompatibility effect between the recombination sites. If recombination is eliminated or significantly reduced when a specific nucleotide is changed, then that nucleotide is required for recognition of the recombination site by the recombinase.

Examples of dissection of the critical sequences in recombination sites of recombinases are described by Hoess et al., *Nucleic Acids Res.* 14:2287–2300 (1986) (involving P1 recombinase); Sauer B., *Nucleic Acids Res.,* 24:4608–4613 (1996) (involving Cre recombinase); Lee and Saito, *Gene* 216(1):55–65 (1998) (involving Cre recombinase); and Umlauf and Cox, *EMBO J* 7(6):1845–52 (1988)(involving FLP recombinase). Similar techniques can be used to determine the recognition sequences of other recombinases.

2. Compatibility Sequences

Compatability sequences are regions in a recombination site that must be similar in a pair of recombination to occur between them. In general, the sequence of recombination sites must be similar for recombination to occur between them. Examples of compatibility sequences are spacer sequences between repeats in recombination sequences. All or some of the nucleotides in the recognition sequences for a recombination site may be involved in compatibility. For example, where some degeneracy of the recognition sequences is allowed, similar recognition sequences may be required in a pair of recombination sites for recombination to occur between them. Thus, compatibility between recombination sites can be affected by using different sequences in the compatibility sequences other than the sequences required for recognition of the site by the recombinase (that is, recognition sequences), compatibility sequences that are part of the recognition sequences, or both. It is preferred that compatibility between recombination sites be altered by using different sequences in the compatibility sequences other than the sequences required for recognition of the site by the recombinase.

Compatibility sequences for many recombinases are known or can be determined through routine analysis. In general, compatibility sequences can be easily determined by varying the sequence of recombination sites and determining if recombination between the sites can still occur. For this purpose, only one of the sites in the pair of sites to be recombined should be altered. That is, the same sequence changes should not be made to both sites. The isolates incompatibility effect between the recombination sites. Further, only those nucleotide positions that are not a part of the recognition sequence of the site should be altered to avoid recognition problems. If recombination is eliminated or significantly reduced when a specific nucleotide is changed, then that nucleotide is required for compatibility of the recombination site.

Examples of dissection of the critical sequences in recombination sites of recombinases are described by Hoess et al., *Nucleic Acids Res.* 14:2287–2300 (1986)(involving P1 recombinase); Sauer B. *Nucleic Acid Res.,* 24:4608–4613 (1996)(involving Cre recombinase); Lee and Saito, *Gene* 216(1):55–65 (1998) (involving Cre recombinase); and Umlauf and Cox, *EMBO J* 7(6):1845–52 (1988)(involving FLP recombinase). Similar techniques can be used to determine the compatibility sequences of other recombinases.

Recognition and compatibility sequences can be further understood using Cre recombination sites as an example.

Wild type Cre recombinase mediates recombination between sites having the sequence $N_1N_2N_3$ACTTCGTATANN NNNNNNTATACG AAGTN$_3$'N$_2$'N$_1$' (SEQ ID NO:5), which includes both specific and non-specific sequences (that is, recognition sequences and compatibility sequences respectively). The sequences ACTTCGTATA (bases 4–13% SEQ ID NO:5) and TATACGAAGT (bases 22–31 of SEQ ID NO: 7) (an inverted repeat of the first sequence) are recognized by the Cre recombinase and are the recognition sequences in Cre recombinase sites. Variant Cre recombinases recognize sites having different recognition sequences. The non-specific sequences (positions with "N" in the recognition sequence), although not limited in sequence, must be compatible with the non-specific sequences of the partner recombination site in order for recombination to be efficient. Thus, the non-specific sequences are the compatibility sequences of a recombinase site.

C. Recombination Constructs

Recombination constructs are designed to provide an observable change when recombination between recombination sites occurs. Preferred recombination constructs include two pairs of recombination sites, one pair having a variant seuqence and another pair having a sequence recognized by non-mutant recombinase (for example, wild type recombinase). Sites in the first pair are referred to as variant recombination sites. Generally, recombination constructs include a first nucleic acid sequence that includes a first reporter gene and first and second recombination sites, where the first and second recombination sites are variant recombination sites, and a second nucleic acid sequence that includes a second reporter gene and third and fourth recombination sites, where the third and fourth recombination sites can be recombined by a non-mutant recombinase. The first and second nucleic acid sequences need not be present on the same vector or on the same nucleic acid molecule (for example, the chromosome), although this is preferred. It is preferred that recombination constructs be embodied in vectors, such as plasmids.

In one embodiment of the disclosed recombination constructs, the sequence of the recombination sites in the constructs are chosen such that the recognition sequences of the first and second recombination sites differ from the recognition sequences of the third and fourth recombination sites. The sequence of the recombination sites can also be chosen such that the compatibility sequences of the first and second recombination sites differ from the compatibility sequences of the third and fourth recombination sites such that the first and second recombination sites cannot recombine with the third and fourth recombination sites. The sequence of the recombination sites can also be chosen such that the compatibility sequences of the first and second recombination sites are sufficiently similar to allow recombination between the first and second recombination sites, and such that the compatibility sequences of the third and fourth recombination sites are sufficiently similar to allow recombination between the third and fourth recombination sites. The above sequence relationships result in constructs where the first and second recombination sites can recombine (in the presence of a recombinase that recognizes the sites), the third and fourth recombination sites can recombine, but where the neither the first nor second recombination site can recombine with either the third or fourth recombination site (since differences in the compatibility sequences prevent recombination).

Arriving at recombination sites having relationships as described above is preferably accomplished in the following way. Starting with a given recombination site sequence (which can be recombined by a non-mutant recombinase), parallel changes are made in the compatibility sequences of the first and second recombination sites. These altered recombination sites should then be tested to make sure that the non-mutant recombinase can still mediate their recombination. This helps insure that compatibility sequence changes have not inadvertently affected the function of the recombination sites. Once this is confirmed, changes can be made to the recognition sequences of the first and second recombination sites. These changes result in variant recombination sites for which variant recombinases can be identified using the method disclosed herein. The resulting recombination sites have the desired propertied: incompatibility with the third and fourth recombination sites and variant recognition sequences that extend the range of recombination-competent sites.

The recombination sites can have a variety of properties and relationships that make them useful for particular purposes. For example, the recombination sites can be designed such that the first and second recombination sites cannot be recombined by non-mutant recombinase to s significant extent. The allows separate assessment of cleavage by mutant and non-mutant recombinase. It is also useful if the first and second recombination sites have identical sequences, and the third and fourth recombination sites have identical sequences.

Recombination between the recombination sites can have a variety of effects that allow detection of recombination. For example, the constructs can be designed such that recombination between the first and second recombination sites alter the expression of the first reporter gene, where recombination between the first and second recombination sites is determined by determining if expression of the first reporter gene is altered; recombination between the third and fourth recombination sites alters the expression of the second reporter gene, where recombination between the third and fourth recombination sites is determined by determining if expression of the second reporter gene is altered; recombination between the first and second recombination sites allow the first reporter gene to be expressed; the first nucleic acid sequence includes a spacer sequence flanked by the first and second recombination sites, where the spacer sequence interrupts the first reporter gene such that the first reporter gene is not expressed, and where recombination of the first and second recombination sites excise the spacer sequence which allows the first reporter gene to be expressed; and/or a portion of the first reporter gene is initiated, wherein the inverted portion of the first reporter gene is flanked by the first and second recombination sites, wherein recombination of the first and second recombination sites inverts the inverted portion of the first reporter gene which allows the first reporter gene to be expressed.

The constructs can also be designed such that recombination between the first and second recombination sites prevents expression of the first reporter gene; the first reporter gene is flanked by the first and second recombination sites, where recombination of the first and second recombination sites excises the first reporter gene which prevents expression of the first reporter gene; a portion of the first reporter gene is flanked by the first and second recombination sites, where recombination of the first and second recombination sites inverts the flanked portion of the first reporter gene which prevents expression of the first reporter gene; recombination between the third and fourth recombination sites allows the second reporter gene to be expressed, and/or the second nucleic acid sequence includes a spacer sequence flanked by the third and fourth recombination sites, where the spacer sequence interrupts the second reporter gene such that the second reporter gene is not expressed, and where recombination of the third and fourth recombination sites excises the spacer sequence which allows the second reporter gene to be expressed.

The constructs can also be designed such that a portion of the second reporter gene is inverted, where the inverted portion of the second reporter gene is flanked by the third and fourth recombination sites; and where recombination of the third and fourth recombination sites inverts the inverted portion of the second reporter gene which allows the second reporter gene to be expressed; recombination between the third and fourth recombination sites prevents expression of the second reporter gene to be expressed; the second reporter gene is flanked by the third and fourth recombination sites, where recombination of the third and fourth recombination sites excises the second reporter gene which prevents expression of the second reporter gene; and/or a portion of the second reporter gene is flanked by the third and fourth recombination sites, where recombination of the third and fourth recombination sites inverts the flanked portion of the second reporter gene which prevents expression of the second reporter gene.

Expression of a reporter gene can include transcription of the gene, translation of the transcript (if the gene encodes a protein), and/or production of an active protein. As used therein, whether a reporter gene is expressed depends on the context. In general, a gene is considered to be expressed if it produces the expression product to be detected. Such expression products include full or partial transcripts of the gene, full or partial proteins, including active or inactive forms of the proteins, translated from the transcript. Since the goal in using reporter genes in the disclosed method is the detection of expression, any of these forms of expression product can be the object of detection. For example, if the gene's transcript is to be detected, the gene will be considered to be expressed if it produces the transcript, regardless of whether the transcript is translated or whether the resulting protein is active. If the an active protein encoded by the gene is to be detected, the gene is not expressed unless active protein is produced—mere transcription of the gene, or even translation to produce an inactive protein, will not be enough in this context. As a consequence, the expression product to be detected will influence the manner in which reporter genes should be interrupted or invented in the disclosed constructs. For example, nearly any interruption of a reporter gene would prevent expression of an active protein encoded by the gene. On the other hand, an interruption of the coding region will usually not prevent production of a transcript. The structure of the disclosed constructs should be designated with these principals in mind. As used herein, an inactive expression product refers to an expression product that does not have an activity exhibited by the active form of the expression product where the activity is required for detection of expression in the assay scheme being used.

The constructs can be designed such that the first nucleic acid sequence is a first nucleic acid constructs and the second nucleic acid sequence is on a second nucleic acid construct; the first nucleic acid construct is an extrachromosomal vector and the second nucleic acid construct is in the genome of a host cell; and/or the first and second nucleic acid constructs are on the same nucleic acid construct.

D. Reporter Genes

Reporter genes are used to monitor whether recombination occurs in the disclosed constructs. Reporter genes can be any gene the expression of which can be detected either directly or indirectly. These include genes encoding enzymes, such as β-galactosidase, luciferase, and alkaline phosphatase, that can produce specific detectable products, and genes encoding proteins that can be directly detected. Virtually any protein can be directly detected by using, for example, specific antibodies to the protein. A preferred reporter protein that can be directly detected is the green fluorescent protein (GFP). GFP, from the jellyfish *Aequorea victoria*, produces fluorescence upon exposure to ultraviolet light without the addition of a substrate (Chalfie et al., *Science* 263:802–5 (1994)). A number of modified GFPs have been created that generate as much as 50-fold greater fluorescence than does wild type GFP under standard conditions (Cormack et al., *Gene* 173:33–8 (1996); Zolotukhin et al., *J. Virol* 70:4646–54 (1996)). This level of fluorescence allows the detection of low levels of expression in cells.

Reporter genes encoding proteins producing a fluorescent signal are useful since such a signal allows cells to be sorted using FACS. Another way of sorting cells based on expression of the reporter gene involves using the reporter protein as a hook to bind cells. For example, a cell surface protein such as a receptor protein can be bound by a specific antibody. Cells expressing such a protein can be captured by, for example, using antibodies bound to a solid substrate, using antibodies bound to magnetic beads, or capturing antibodies bound to the reporter protein. Many techniques for the use of antibodies as capture agents are known and can be used with the disclosed method.

The reporter gene can also encode an expression product that regulates the expression of another gene. This allows detection of expression of the reporter gene by detecting expression of the regulated gene. For example, a repressor protein can be encoded by the reporter gene. Loss of expression of the reporter gene (via recombination) would then result in derepression of the regulated gene. This type of indirect detection allows positive detection of loss of the expression of the reporter gene by the affector RNA molecule. One preferred form of this type of regulation is the use of an antibiotic resistance gene regulated by a repressor protein encoded by the reporter gene. By exposing the host cells to the antibiotic, only those cells in which expression of the reporter gene has been inhibited will grow since expression of the antibiotic resistance gene will be derepressed.

E. Expression Sequences

The reporter genes can be expressed using any suitable expression sequences. Numerous expression sequences are known and can be used for expression of the reporter genes. Expression sequences can generally be classified as promoters, terminators, and, for use in eukaryotic cells, enhancers. Expression in prokaryotic cells also requires a Shine-Dalgarno sequence just upstream of the coding region for proper translation initiation. Inducible promoters are preferred for use with first reporter gene since it is preferred that expression of the first gene be adjustable.

Promoters suitable for use with prokaryotic hosts illustrated include the β-lactamase and lactose promoter systems, tetracycline (tet) promoter, alkaline phosphatase promoter, the tryptophan (trp) promoter system and hybrid promoters such as the tack promoter. However, many other functional bacterial promoters are suitable. Their nucleotide sequences are generally known.

Suitable promoting sequences for use with yeast hosts include the promoters for 3-phosphoglycerate kinase, enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosphosphate isomerase, phosphoglucose isomerase, and glucokinase. Examples of inducible yeast promoters suitable for use in the disclosed vectors include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Yeast enhancers also are advantageously used with yeast promoters.

Preferred promoters for use in mammalian host cells include promoters from polymoma virus, Simian Virus 40(SV40), adenovirus, retroviruses, hepatitis B virus, herpes simplex virus (HSV), Rous sarcoma virus (RSV), mouse mammary tumor virus (MMTV), and most preferably cytomegalovirus (CMV), or from heterologous mammalian promoters such as the β actin promoter. Particularly preferred are the early and late promoters of the SV40 virus and the immediate early promoter of the human cytomegalovirus, MMTV LTR, RSV-LTR, and the HSV thimidine kinase promoter.

Transcription of the reporter gene by higher eukaryotes can be increased by inserting an enhancer sequence into the vector. Many enhancer sequences are now known from mammalian genes (globin, elastase, albumin, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers.

The disclosed vectors preferably also contain sequences necessary for accurate 3' end formation of both reporter and affector RNAs. In eukaryotic cells, this would be a polyadenylation signal. In prokaryotic cells, this would be a transcription terminator.

METHOD

A. Identification of Variant Recombinases

The disclosed method involves producing mutant recombinases and testing the mutant recombinases with specially designed constructs. The constructs contain variant recombination sites that are not recognized by non-mutant recombinase but will undergo recombination in the presence of a mutant recombinase with altered specificity. The disclosed method also involves determining whether a variant recombinase retains the ability to mediate recombination in recombination sites recognized by non-variant recombinase. This can be accomplished by using constructs containing recombination sites recognized by non-variant recombinase. Recombination at these recombination sites can be monitored or detected by any suitable means. It is preferred that recombination is detected by screening or selection based on the expression or lack of expression of a reporter gene. This can be accomplished by using constructs containing a reporter gene associated with the recombination sites such that the reporter gene is rearranged or deleted, or a spacer sequence interrupting the reporter gene is rearranged or deleted, as a result of recombination at the recombination sites. Recombination of such constructs will result in a loss of expression of the reporter gene, where the construct contained a functional reporter gene, or in a gain in expression of the reporter gene, where the construct contained a non-functional reporter gene.

1. Production of Mutant Recombinases

Mutant recombinases can be produced by any suitable technique. In general, all that is required is a method of generating a variety of recombinase proteins having a variety of amino acid sequences. the most preferred way of doing this is to mutagenize or alter nucleic acid encoding the recombinase and then expressing the mutant recombinases. Numerous techniques for introducing alterations into nucleic acid sequences are known and can be used in the disclosed method. For example, alterations can be made by chemical mutagenesis, introduction of degenerate nucleic acid fragments into the base nucleic acid molecule, and low fidelity PCR. The goal of this mutagenesis or alteration will be the generation of a population or set of mutant recombinases having a variety of sequences. The broader the range of variants, the more raw material for the identification process.

2. Identification of Variant Recombinases That Recognize Variant Recombination Sites Variant recombinases that can mediate recombination at variant recombination sites are identified in the disclosed method by selecting for, screening for, or otherwise detecting recombination of specially designed constructs having variant recombination sites. Recombination at variant recombination sites can be monitored or detected by any suitable means. It is preferred that recombination is detected by screening or selection based on the expression or lack of expression of a reporter gene. This can be accomplished by using constructs containing a reporter gene associated with the variant recombination sites such that the reporter gene is rearranged or deleted, or a spacer sequence interrupting the reporter gene is rearranged or deleted, as a result of recombination at the recombination sites. Recombination of such constructs will result in a loss of expression of the reporter gene, where the construct contained a functional reporter gene, or in a gain in expression of the reporter gene, where the construct contained a non-functional reporter gene.

3. Identification of Variant Recombinases That Recognize Non-Variant Recombination Sites Variant recombinases that can mediate recombination at recombination sites recognized by non-variant recombinase (non-variant recombination sites) are identified in the disclosed method by selecting for, screening for, or otherwise detecting recombination of specially designed constructs having recombination sites recognized by non-variant recombinase. Recombination at these recombination sites can be monitored or detected by any suitable means. It is preferred that recombination is detected by screening or selection based on the expression or lack of expression of a reporter gene. This can be accomplished by using constructs containing a reporter gene associated with the recombination sites recognized by non-variant recombinase such that the reporter gene is rearranged or deleted, or a spacer sequence interrupting the reporter gene is rearranged or deleted, as a result of recombination at the recombination sites. Recombination of such constructs will result in a loss of expression of the reporter gene, where the construct contained a functional reporter gene, or in a gain in expression of the reporter gene, where the construct contained a non-functional reporter gene.

It is preferred that the ability of a variant recombinase to mediate recombination at both variant recombination sites and recombination sites recognized by non-variant recombinase be assessed in the same system (such as a cell strain) either sequentially or simultaneously. When variant recombinases are tested for activity on both variant recombination sites and recombination sites recognized by non-variant recombinase in the same system or at the same time, it is preferred that two different reporter genes which can be separately detected or monitored be used. In this case, a first reporter gene can be associated with the variant recombination sites and a second reporter gene can be associated with recombination sites recognized by non-variant recombinase.

B. Use of Variant Recombinases

Variant recombinases produced in the disclosed method can be used for any purpose that unmodified recombinases can be used. The advantage is that the variant recombinases have a different or broader site specificity. In general, the disclosed variant recombinases can be used to mediate recombination of any nucleic acid in any setting, including in vitro, in cell culture, and in vivo. Recombination can be obtained in single celled organisms, such as bacterial cells, fungal cells, yeast cells, prokaryotic cells, and archae bacterial cells, the cells of multicellular organisms, including plants and animals, both in the organism and in culture. The disclosed variant recombinases can also be used in combination with other recombinases (including other variant recombinases) having a different site specificity. Such combinations allow more complex recombination schemes to be used. Examples of such schemes are discussed below.

For some uses of the disclosed recombinases, first, second, and fourth DNA sequences comprising a first recombination site, a second recombination site, and a third recombination site, respectively, are introduced into cells. As used herein the expression "recombination site" means a nucleotide sequence at which a recombinase or variant recombinase can catalyze a site-specific recombination.

Methods for introducing a DNA sequence into cells are known in the art. These methods typically include the use of a DNA vector to introduce the sequence into the DNA of a single or limited number of eukaryotic cells and then growing such cell or cells to generate a suitable population of cells. As used herein, the term "vector" includes plasmids, viruses, and viral vectors. Preferably, the DNA sequences are introduced by a plasmid capable of transforming a selected cell while carrying a DNA sequence. The particular vector which is employed to introduce the DNA sequence into a selected cell is not critical.

In the present method, the recombination sites are contacted with a variant recombinase, thereby producing the site specific recombination. A preferred means of contacting the DNA to be recombined with a variant recombinase is to place the DNA to be recombined into a cell expressing nucleic acid encoding the variant recombinase. Preferably, expression of the variant recombinase is under the control of a regulatory nucleotide sequence. Suitable regulatory nucleotide sequences are known in the art. The regulatory nucleotide sequence which is employed with a selected eukaryotic cell is not critical to the method. A partial list of suitable regulatory nucleotide sequences includes the long terminal repeat of Moloney sarcoma virus described by Blochlinger and Diggelmann, *Mol. Cell Biol.*, 4:292–2931 (1984); the mouse metallothionein-I promoter described by Pavlakis and Hamer, *Proc. Natl. Acad. Sci. USA*, 80:397–401 (1983); the long terminal repeat of Rous sacroma virus described by Gorman et al., *Proc. Natl. Acad. Sci USA*, 79:6777–6781 (1982); and the early region promoter of SV40 described by Southern and Berg, *J. Mol. Appl. Genet.*, 1:327–341 (1982).

In an embodiment where the cells are yeast, suitable regulatory nucleotide sequences include GAL1, GAL10, ADH1, CYC1, and TRP5 promoters. GAL1 and GAL10 promoters are present on plasmid pBM150 which is described by Johnston and Davis, *Molec. Cell. Biol.*, 4:1440 (1984). The ADH1 promoter, also called ADC1, is present on plasmid pAAH5 which is described by Ammer, *Methods Enzymol.*, 101:192 (1983). The CYC1 promoter is described by Stiles et al., *Cell.* 25:277 (1981). The TRP5 promoter is described by Zalkin and Yanofsky, *J. Biol. Chem.*, 257:1491 (1982). Preferably, the regulatory nucleotide sequence is a GAL1 promoter.

In one embodiment where the cell is yeast, the first, second, and optionally, third and fourth DNA sequences are introduced into one strain of yeast. Alternatively, the DNA sequences are introduced into two different strains of yeast of opposite mating types which are subsequently mated to form a single strain having all three or four DNA sequences. Preferably, the plasmid contains either (1) a nucleotide sequence of DNA homologous to a resident yeast sequence to permit integration into the yeast DNA by the yeast's recombination system or (2) a nucleotide sequence of DNA which permits autonomous replication in yeast. One nucleotide sequence which permits autonomous replication in yeast is an ARS sequence described by Stinchcomb et al., *Nature*, 289:39 (1979). A partial list of plasmids capable of transforming yeast includes YIP5, YRP17 and YEP24. These plasmids are disclosed and described by Botstein and Davis, The Molecular Biology of the Yeast Saccharomyces, Metabolism and Gene Expression (ed. Strathern et al.), (Cold Spring Harbor Laboratory, Cold Spring Harbor, N.Y., 1982), at page 607.

Since most recombination sites are asymmetrical nucleotide sequences, two recombination sites on the same DNA molecule can have the same or opposite orientations with respect to each other. Recombinations between recombination sites in the same orientation result in a deletion of the DNA segment located between the two recombination sites and a connection between the resulting ends of the original DNA molecule. The deleted DNA segment forms a circular molecule of DNA. The original DNA molecule and the resulting circular molecule each contain a single recombination site (see FIG. 2). Recombination between recombination sites in opposite orientations on the same DNA molecule result in an inversion of the nucleotide sequence of the DNA segment located between the two recombination sites (see FIG. 2). In addition, reciprocal exchange of DNA segments proximate to recombination sites located on two different DNA molecules can occur. All of these recombination events are catalyzed by recombinases, including the disclosed variants and wild type recombinases.

Recombination using the disclosed variant recombinases can be used in vitro produce site-specific recombination of nucleic acid molecules. This is useful for a wide variety of manipulations that currently employ wild type recombinases or involve traditional restriction enzyme cleavage followed by ligation. Examples include recombination of libraries of DNA fragments into vectors or in desired structures, and labeling of DNA via recombination. Recombined DNA formed by in vitro recombination can then be introduced into cells. For example, constructs formed in vitro can be introduced into cells to resolve the structures formed in vitro or to select active structures. In particular, large concatemers of subject DNA and spacer/vector fragments can be made, introduced into cells, and circularized into vector units in the cells. Such recombination could also be performed in vitro if desired.

The disclosed variant recombinases can be used to labeled DNA by recombining a DNA molecule of interest with a labeled DNA molecule. Use of a recombinase for labeling is advantageous since it involves fewer steps than traditional labeling via DNA synthesis or ligation. These considerations are particularly important when large DNA molecules (over 20 kb) are to be labeled since such large molecules with fragment more the more they are manipulated.

Recombination mediated by the disclosed variant recombinases and variant recombination sites can be used to manipulate a host cell genome as desired and simultaneously introduce a marker gene flanked by the recognition sites of a second recombinase. After selection, leading to an accumulation of cells carrying the desired genomic alteration, one could simply remove the marker gene by expression of the second site-specific recombinase. A large number of recombinases suitable for this purpose exists in nature, including δ Integrase (Int), yeast Flp, etc. (Nunes-Döby et al., *Nucl. Acids Res.*, 26:391–406 (1998)). Variant recombinases having different site specificity can also be used.

Since the disclosed variant recombinases recognize both wild type recombination sites and variant recombination sites that are not recognized by wild type recombinase, wild type recombinase and variant recombinases can be used to mediate sequential recombination between nucleic acids containing a combination of wild type recombination sites and variant recombination sites. For example, generation of knockout animals and plants can be made more efficient by using a structure wild type recombination site-selectable marker-wild type recombination site-endogenous gene-variant recombination site (rather than the conventional wild type recombination site-selectable marker-wild type recombination site-endogenous gene-wild type recombination site). Such a structure allows the selectable marker to be removed by the action of wild type recombinase without disturbing the gene since wild type recombinase will not recognize the variant recombination site to any significant degree. The endogenous gene can then be removed later by the action of a variant recombinase since the disclosed variant recombinases recognize both wild type and variants recombination sites.

In a preferred embodiment of the disclosed method, the first and second DNA sequences are introduced into cells connected by a pre-selected DNA segment. The segment can be a gene or any other sequence of deoxyribonucleotides of homologous, heterologous or synthetic origin. Preferably, the pre-selected DNA segment is a gene for a structural protein, an enzyme, or a regulatory molecule. If the first and second recombination sites have the same orientation, activation of the regulatory nucleotide sequence produces a deletion of the pre-selected DNA segment. If the first and second recombination sites have opposite orientation, activation of the regulatory nucleotide sequence produces an inversion of the nucleotide sequence of the pre-selected DNA segment.

If a fourth DNA sequence (containing the third recombination site) is also introduced into cells, it is preferred that the second and fourth DNA sequences be introduced into cells connected by a second pre-selected DNA segment. The second segment can be a gene or any other sequence of deoxyribonucleotides of homologous, heterologous or synthetic origin. Preferably, the second pre-selected DNA segment is a gene for a structural protein, an enzyme, or a regulatory molecule. If the second and third recombination sites have the same orientation, activation of the regulatory nucleotide sequence produces a deletion of the second pre-selected DNA segment. If the second and third recombination sites have opposite orientation, activation of the regulatory nucleotide sequence produces an inversion of the nucleotide sequence of the second pre-selected DNA segment.

Combinations of wild type and variant recombination sites, and combination of different orientations of the recombination sites, in DNA introduced into cells can multiply recombination options. For example, if the first and second recombination sites are wild type recombination sites and the third recombination site is a variant recombination site (all in the same orientation) then wild type recombinase can produce a deletion of the first pre-selected DNA segment (but not the second) and a variant recombinase can produce a deletion of the first, second, or both pre-selected DNA segments. This arrangement allows sequential deletion of the first and second pre-selected DNA segments.

If the first and segment recombination sites are wild type recombination sites and the third recombination site is a variant recombination site, and the first recombination site has the opposite orientation from the second and third recombination sites (which, of course, have the same orientation) when wild type recombinase can produce an inversion of the first pre-selected DNA segment and a variant recombinase can produce a deletion of the second pre-selected DNA segment (and/or produce an inversion of the first pre-selected DNA segment or the entire section spanning the first, second, and third recombination sites).

If the first and third recombination sites are wild type recombination sites and the second recombination site is a variant recombination site, and the second recombination site has the opposite orientation from the first and third recombination sites (which, of course, have the same orientation) then wild type recombinase can produce a deletion of the entire section spanning the first, second, and third recombination sites, and a Cre variant can produce an inversion of the first, second, or both pre-selected DNA segments.

If the first and third recombination sites are wild type recombination sites and the second recombination site is a variant recombination site, and the first recombination site has the opposite orientation from the second and third recombination sites (which, of course, have the same orientation) then wild type recombinase can produce an inversion of the entire section spanning the first, second, and third recombination sites, and a variant recombinase can produce a deletion of the second pre-selected DNA segments and an invention of the first pre-selected DNA segment.

Many more combinations of wild type and variant recombination sites and or recombination site orientations are possible. For example, the variant recombinase can also be used with a different variant recombinase having a different site specificity rather than wild type recombinase. The above examples illustrate the general principles involved in designing specific recombinations that may be desired. It should be understood that the above combinations of recombination sites can be extended to the use of more recombination sites (that is more than three) and more intervening, pre-selected DNA segments.

For some uses of the disclosed recombinases, first, second, and fourth DNA sequences comprising a first lox site, a second lox site, and third lox site, respectively, are introduced into cells. As used herein the expression "lox site" means a nucleotide sequence at which the gene product of the cre gene, referred to herein as Cre, and/or the disclosed Cre variants, can catalyze a site-specific recombination. LoxP site is a 34 base pair nucleotide sequence (FIG. 1) which can be directly synthesized or isolated from bacteriophage P1 by methods known in the art. The Lox P site is an example of a wild type lox site. One method for isolating a LoxP site from bacteriophage P1 is disclosed by Hoess et al., *Proc. Natl. Acad. Sci. USA*, 79:3398–3402 (1982). The LoxP site consists of two 13 base pair inverted repeats separated by an 8 base pair spacer region. The nucleotide sequences of the insert repeats and the spacer region are as follows ATAACTTCGTATAATGTATGCTATACGAAG
       TTAT                                  (SEQ ID NO.7)

Other wild type lox sites include LoxB, LoxL and LoxR sites which are nucleotide sequences isolated from *E. coli*.

These sequences are disclosed and described by Hoess et al., *Proc. Natl. Acad. Sci. USA,* 79:3398–3402 (1982). Preferred wild type lox sites are LoxP or LoxC2. Lox sites can also be produced by a variety of synthetic techniques which are known in the art. For example, synthetic techniques for producing lox sites are disclosed by Ito et al., *Nuc. Acid Res.,* 10:1755 (1982) and Ogilvie et al., Science, 214:270 (1981).

The gene product of the cre gene is a recombinase herein designated "Cre" which effects site-specific recombination of DNA as lox sites. As used herein, the expression "cre gene" means a nucleotide sequence which codes for a gene product which effects site-specific recombination of DNA in cells at lox sites. One cre gene (the wild type cre gene) can be isolated from bacteriophage P1 by methods known in the art. One method for isolating a cre gene from bacteriophage P1 is disclosed by Abremski et al., *Cell,* 32:1301–1311 (1983), the disclosure of which is incorporated herein by reference.

Genes engineered into cells for producing a foreign protein are often placed under the control of a highly active promoter. The activity of the promoter can result in an overproduction of the protein which interferes with the growth of the engineered cell. This over production of the protein can make it difficult to grow the engineered cell in sufficient quantity to make protein production economically feasible. The present invention provides a method whereby engineered cells can be grown to a desired density prior to expressing the engineered gene. The engineered gene is expressed, as desired, by activating a regulatory nucleotide sequence responsible for controlling expression of DNA encoding a variant recombinase. Methods of controlling the expression of an engineered gene include the following:

(1) A DNA segment flanked by recombination sites in the same orientation is introduced into DNA in a cell between a promoter and an engineered gene to render the promoter incapable of expressing the gene. A second DNA sequence comprising a regulatory nucleotide sequence and DNA encoding a variant recombinase is also introduced in the DNA. After the engineered cells are grown to a desired density, the regulatory nucleotide sequence is activated thereby effecting expression of the variant recombinase and producing a deletion of the DNA segment. The engineered gene would then be expressed.

(2) A gene for a regulatory molecule flanked by recombination sites in the same orientation is introduced into DNA in a cell. The regulatory molecule inhibits expression of an engineered gene. A second DNA sequence comprising a regulatory nucleotide sequence and DNA encoding a variant recombinase is also introduced into the DNA. After the engineered cells are grown to a desired density, the regulatory nucleotide sequence is activated thereby effecting expression of the variant recombinase and producing a deletion of the gene for the regulatory molecule. The engineered gene would then be expressed.

(3) An engineered gene lacking a promoter and flanked by two recombination sties in opposite orientations is introduced into DNA in a cell such that the 3' end of the gene lies adjacent to the transcription start site of a regulatory nucleotide sequence. A second DNA sequence comprising a regulatory nucleotide sequence and DNA encoding a variant recombinase is also introduced into the DNA. Since the engineered gene would be transcribed in the antisense direction, no engineered protein would be produced. After the engineered cell is grown to a desired density, the regulatory nucleotide sequence is activated thereby effecting expression of the variant recombinase and producing an inversion of the desired gene. The engineered gene could then be transcribed in the proper direction and expressed.

Numerous methods and techniques have been developed for the use of Cre recombinase and other, similar recombinases such as FLP. The disclosed variant recombinases can also be used in any of these methods. Adaptation of these methods to the use of the disclosed variant recombinases is straightforward. Generally, all that is required is substitution of a variant recombinase (or a gene expressing a variant recombinase) for the original recombinase (or recombinase gene) and, if appropriate, substitution of variant (or wild type) recombination sites for the original recombination sites used in the method.

Examples of methods involving wild type recombinases and wild type recombination sites that can be adapted for use with the disclosed variant recombinases and recombination sites include recombination of DNA in phage packaging systems, recombination of DNA to form phage display libraries (for example, Fisch et al., *Proc. Natl. Acad Sci USA* 93(15):7761–6 (1996), and Waterhouse et al., *Nucleic Acids Res* 21(9):2265–6 (1993), and other uses (for example, (Sauer et al., *Proc. Natl. Acad. Sci. USA* 84: 9108–9112 (1987), Mullins et al., *Nucleic Acids Res* 25(12):2539–40 (1997), Aoki et al., *Mol Med* 5(4):224–31 (1999)).

Other examples of specific methods in which the disclosed variant recombinases can be used or substituted include methods disclosed in U.S. Pat. No. 5,888,981, U.S. Pat. No. 5,888,732, U.S. Pat. No. 5,885,836, U.S. Pat. No. 5,885,793, U.S. Pat. No. 5,885,779, U.S. Pat. No. 5,885,776, U.S. Pat. No. 5,882,893, U.S. Pat. No. 5,882,888, U.S. Pat. No. 5,877,400, U.S. Pat. No. 5,871,907, U.S. Pat. No. 5,866,755, U.S. Pat No. 5,866,361, U.S. Pat. No. 5,859,310, U.S. Pat. No. 5,858,657, U.S. Pat. No. 5,854,067, U.S. Pat. No. 5,851,808, U.S. Pat. No. 5,849,995, U.S. Pat. No. 5,849,989, U.S. Pat. No. 5,849,708, U.S. Pat. No. 5,849,572, U.S. Pat. No. 5,849,571, U.S. Pat. No. 5,849,553, U.S. Pat. No. 5,844,079, U.S. Pat. No. 5,843,744, U.S. Pat. No. 5,843,742, U.S. Pat. No. 5,843,694, U.S. Pat. No. 5,840,540, U.S. Pat. No. 5,837,844, U.S. Pat. No. 5,837,242, U.S. Pat. No. 5,834,202, U.S. Pat. No. 5,830,729, U.S. Pat. No. 5,830,698, U.S. Pat. No. 5,830,461, U.S. Pat. No. 5,817,492, U.S. Pat. No. 5,814,618, U.S. Pat. No. 5,814,500, U.S. Pat. No. 5,814,300, U.S. Pat. No. 5,807,995, U.S. Pat. No. 5,807,708, U.S. Pat. No. 5,801,030, U.S. Pat. No. 5,800,998, U.S. Pat. No. 5,795,734, U.S. Pat. No. 5,795,726, U.S. Pat. No. 5,792,833, U.S. Pat. No. 5,792,632, U.S. Pat. No. 5,789,156, U.S. Pat. No. 5,777,194, U.S. Pat. No. 5,776,449, U.S. Pat. No. 5,773,697, U.S. Pat. No. 5,770,384, U.S. Pat. No. 5,767,376, U.S. Pat. No. 5,763,240, U.S. Pat. No. 5,756,671, U.S. Pat. No. 5,744,343, U.S. Pat. No. 5,744,336, U.S. Pat. No. 5,736,377, U.S. Pat. No. 5,733,744, U.S. Pat. No. 5,733,743, U.S. Pat. No. 5,733,733, U.S. Pat. No. 5,731,182, U.S. Pat. No. 5,723,765, U.S. Pat. No. 5,723,333, U.S. Pat. No. 5,723,287, U.S. Pat. No. 5,721,367, U.S. Pat. No. 5,721,118, U.S. Pat. No. 5,700,470, U.S. Pat. No. 5,686,595, U.S. Pat. No. 5,679,523, U.S. Pat. No. 5,677,177, U.S. Pat. No. 5,658,772, U.S. Pat. No. 5,656,438, U.S. Pat. No. 5,654,182, U.S. Pat. No. 5,654,168, U.S. Pat. No. 5,650,491, U.S. Pat. No, 5,650,308, U.S. Pat. No. 5,650,298, U.S. Pat. No. 5,643,727, U.S. Pat. No. 5,641,866, U.S. Pat. No. 5,641,748, U.S. Pat. No. 5,639,726, U.S. Pat. No. 5,635,381, U.S. Pat. No. 5,629,179, U.S. Pat. No. 5,629,159, U.S. Pat. No. 5,614,389, U.S. Pat. No. 5,612,205, U.S. Pat. No. 5,596,089, U.S. Pat. No. 5,591,609, U.S. Pat. No. 5,589,362, U.S. Pat. No. 5,539,094, U.S. Pat. No. 5,530,191, U.S. Pat. No. 5,527,695, U.S. Pat. No. 5,510,099, U.S. Pat. No. 5,478,731, U.S. Pat. No. 5,441,884, U.S. Pat. No. 5,434,066, U.S. Pat. No. 5,378,618, U.S. Pat. No. 5,354,668, U.S. Pat. No. 5,334,515, U.S. Pat. No. 5,300,431, and U.S. Pat. No. 4,959,317.

1. Use of Variants Recombinases in Plants and Plant Cells

Methods for introducing a DNA sequence into plant cells are known in the art. Nucleic acids can generally be introduced into plant protoplasts, with or without the aid of electroporation, polyethylene glycol, or other processes known to alter membrane permeability. Nucleic acid constructs can also be introduced into plants using vectors comprising part of the Ti- or Ri-plasmid, a plant virus, or an autonomously replicating sequence. Nucleic acid constructs can also be introduced into plants by microinjection or by high-velocity microprojectiles, also termed "particle bombardment" or "biolistics" (Sanford, J. C., *Tibtech* 6: 299 (1988)), directly into various plant parts. The preferred means of introducing a nucleic acid fragment into plant cells involves the use of *A. tumefaciens* containing the nucleic acid fragment between T-DNA borders either on a disarmed Ti-plasmid (that is, a Ti-plasmid from which the genes for tumorigenicity have been deleted) or in a binary vector in trans to a disarmed Ti-plasmid. The Agrobacterium can be used to transform plants by inoculation of tissue explants, such as stems, roots, or leaf discs, by co-cultivation with plant protoplasts, or by inoculation of seeds or wounded plant parts.

Foreign genes can be introduced into a wide range of crop species. Thus, the disclosed variant recombinases and method are applicable to a broad range of agronomically or horticulturally useful plants. The particular method which is employed to introduce the DNA sequence into a selected plant cell is not critical. In a preferred embodiment, DNA sequences are introduced into plant cells by co-cultivation of leaf discs with *A. tumefaciens* essentially as described by Horsch et al., *Science,* 227: 12279–1231 (1985) omitting the nurse cultures.

In the present method, the recombination sites are contacted with a variant recombinase, thereby producing the site specific recombination. In one embodiment, a variant recombinase, or messenger RNA encoding a variant recombinase, is introduced into the cells directly by microinjection, biolistics, or other protein or RNA introduction procedure. In a preferred embodiment, DNA encoding the variant recombinase is introduced into the plant cell under the control of a promoter that is active in plant cells. Suitable regulatory nucleotide sequences are known in the art. The promoter which is employed with a selected plant cell is not critical to the method of the invention. A partial list of suitable promoters include the 35S promoter of cauliflower mosaic virus described by Odell et al., *Nature,* 313: 810–812 (1985); the promoter from the nopaline synthase gene of *A. tumefaciens* described by Depicker et al., *J. of Mol. Appl. Genet.,* 1:561–573 (1982); the promoter from a Rubisco small subunit gene described by Mazur and Chui, *Nucleic Acids Research* 13: 2373–2386 (1985); the 1' or 2' promoter from the TR-DNA of *A. tumefaciens* described by Velten et al., *EMBO J.* 12: 2723–2730 (1984); the promoter of a chlorophyll a/b binding protein gene described by Dunsmuir et al., *J. Mol. Appl. Genet.* 2: 285–300 (1983); the promoter of a soybean seen storage protein gene described by Chen et al., *Proc. Natl. Acad. Sci. USA,* 83: 8560–8564 (1986); and the promoter from the wheat EM gene described by Marcotte et al., *Nature* 335: 454–457 (1988). Variant recombinases can be expressed throughout the plant generally in all cells at all stages of development, or expression of variant recombinases can be more specifically controlled through the use of promoters or regulatory nucleotide sequences having limited expression characteristics. Variant recombinases can be expressed in a tissue specific manner, for example only in roots, leaves, or certain flower parts. Variant recombinases can be expressed in a developmentally specific time period, for example only during seed formation or during reproductive cell formation. Expression of variant recombinases can also be placed under the control of a promoter that can be regulated by application of an inducer. In this case expression is off or very low until the external inducer is applied. Promoters active in plant cells have been described that are inducible by heat shock (Gurley et al., *Mol. Cell. Biol.* 6: 559–565 (1986)), ethylene (Bfoglie et al., *Plant Cell* 1: 599–607 (1989)), auxin (Hagan and Guilfoyle, *Mol. Cell. Biol.* 5: 1197–1203 (1985)), abscisic acid (Marcotte et al., *Nature* 335: 454–457 (1988)), salicylic acid (EPO 332104A2 and EPO 337532A1), and substituted benzenesulfonamide safeners (WO 90/11361). Control of expression of variant recombinases by the safener-inducible promoter 2—2, or its derivatives, allows the expression to be turned on only when the inducing chemical is applied and not in response to environmental or phytohormonal stimuli. Thus expression can be initiated at any desired time in the plant life cycle. Preferably, the regulatory nucleotide sequence is a 35S promoter or a 2—2 promoter. The above techniques and materials can also be used to express wild type recombinase in plant cells if required by the particular recombination pattern to be accomplished.

One application of the disclosed variants recombinases is in controlling male fertility in a method for producing hybrid crops. Hybridization of a crop involves the crossing of two different lines to produce hybrid seed from which the crop plants are grown. Hybrid crops are superior in that more of the desired traits can be introduced into the production plants. For instance, quality traits such as oil content, herbicide resistance, disease resistance, adaptability to environmental conditions, and the like, can be hybridized in offspring so that the latter are invested with the most desirable traits of its parents. In addition, progeny from a hybrid cross may possess new qualities resulting from the combination of the two parental types, such as yield enhancement resulting from the phenomenon known as heterosis. Controlled cross-fertilization to produce hybrid seeds has been difficult to achieve commercially due to competing self-fertilization, which occurs in most crop plants.

Hybrid seed production is typically performed by one of the following means: (a) mechanically removing or covering the male organs to prevent self-fertilization followed by exposing the male-disabled plants to plants with male organs that contain the trait(s) desired for crossing; (b) growing genetically male-sterile plants in the present of plants with fertile male organs that contain the trait that is desired for crossing; or (c) treating plants with chemical hybridizing agents (CHA) that selectively sterilize male organs followed by exposing the male-disabled plants to plants with fertile male organs that contain the trait that is desired for crossing. Some disadvantages to each of these methods include: (a) applicability only to a few crops, such as corn, where the male and female organs are well separated; and it is labor intensive and costly; (b) genetically male sterile lines are cumbersome to maintain, requiring crosses with restorer lines; (c) all CHAs exhibit some degree of general phytotoxicity and female fertility reduction. Also CHAs often show different degrees of effectiveness toward different crop species, or even toward different varieties within the same species.

A molecular genetic approach to hybrid crop production applicable to a wide range of crops and involves genetic male sterility is described in EPA 89-344029. This system involves the introduction of a cell disruption gene that is expressed only in the tapetal tissue of anthers thereby destroying the developing pollen. The resulting genetically male sterile plants serve as the female parents in the cross to produce hybrid seed. This system could be highly effective and desirable. However one disadvantage is that since the male sterile parent is heterozygous for the sterility gene which acts as a dominant trait, only 50% of the plants grown from the hybrid seed are fertile, the rest retain the sterility gene. This situation will result in reduced pollen shed in the production field which may lead to reduce seed set and yield. Addition of recombinase technology to this hybrid scheme allows restoration of fertility to a much higher percentage of plants in the production field, as well as elimination of the cell disruption gene. Placing the male sterility gene between recombination sites allows it to be deleted following introduction of a variant recombinase into the hybrid from the male parent.

Another application of the disclosed variant recombinases is in making seedless produce. Seedlessness is desirable in consumed produce for convenience and taste. Currently "seedless" watermelon is sold that actually contains some developed seed and a large number of immature seed that varies in size up to that of fully mature seed. To produce these watermelon first a hybrid cross is made between a tetraploid maternal parent and a diploid pollinator. The resulting triploid seed produces self-infertile plants that are crossed with a diploid pollinator to produce seedless fruit (Kihara, *Proc. Soc. Hart. Sci.,* 58: 217–230, (1951)). This production scheme suffers the following problems: (i). Creating a tetraploid plant, which is accomplished by a chromosome duplication method, is difficult. Also the number of seeds per fruit on this tetraploid plant must be low since this has a positive correlation with seed number in the final product (Andrus, Production of Seedless Watermelons, USDA Tech. Bull. No. 1425 (1971)); (ii) good combining ability of the diploid pollinator and the tetraploid plant is difficult to achieve (Henderson, *J. Amer. Soc. Hort. Sci.,* 102: 293–297 (1977)); (iii) the triploid seeds are much inferior to regular diploid seeds in vigor and germinability (Maynard, *Hort. Sci.,* 24: 603–604 (1989)).These problems, together with incomplete seedlessness in the final product, make the development of seedless watermelon slow and difficult. This ploidy-based approach to seedlessness is possible only in those few species where unusual euploidy plants (tetraploid and triploid for watermelon, for example) are viable.

A molecular genetic approach to seedlessness involving the disclosed variant recombinases is much more efficient, resulting in a more reliably seedless product and does not involve changes in ploidy. Thus it is more generally applicable to a wider range of species. A recombination site/poly A-inactivated cell disruption gene regulated by a seed-specific promoter is introduced into a plant. When this plant is crossed to a plant expressing a variant recombinase, the disruption gene is activated expressed in the seed, thereby disrupting seed development. The certainty of endosperm failure (caused by the cell disruption gene product) leading to the abortion of the whole seed is very high. In most dicots, the endosperm supplies the nutrients needed for early embryo development. Endosperm abortion invariably leads to seed abortion (Brink and Cooper, *Bot. Rev.* 8: 423–541 (1947)).

The seed-specific promoter used can be selected from the group of promoters known to direct expression in the embryo and/or the endosperm of the developing seed, most desirably in the endosperm. Examples of seed-specific promoters include but are not limited to the promoters of seed storage proteins. The seed storage proteins are strictly regulated, being expressed almost exclusively in seeds in a highly tissue-specific and stage-specific manner (Higgins et al., *Ann. Rev. Plant Physiol.* 35: 191–221 (1984); Golderg et al., *Cell* 56: 149–60 (1989)). Also, different seed storage proteins may be expressed at different stages of seed development and in different parts of the seed.

There are numerous examples of seed-specific expression of seed storage protein genes in transgenic dicotyledonous plants. These include genes from dicotyledonous plants for bean β-phaseolin (Sengupta-Goplalan et al., *Proc. Natl. Acad. Sci. USA* 82: 3320–3324 (1985) and Hoffman et al., Plant Mol. Biol. 11: 717–729 (1988)), bean lectin (Voelker et al., *EMBO J* 6: 3571–3577 (1987), soybean lectin (Ocamuro et al., *Proc. Natl. Acad. Sci. USA* 83: 8240–8344 (1986)). soybean kunltz trypsin inhibitor (Perez-Grau and Goldberg Plant Cell 1: 1095–1109 (1989)), soybean β-conglycinin (Beachy et al., *EMBO J* 4: 3047–3053 (1985), Barker et al., *Proc. Natl. Acad. Sci.* 85: 458–462 (1988), Chen. et al. *EMBO J* 7: 297–302 (1988), Chen et al., Dev. Genet. 10: 112–122 (1989), Naito et al., *Plant Mol. Biol.* 11: 683–695 (1988)), pea vicillin (Higgins et al., *Plant Mol. Biol.* 11: 109–123 (1988)), pea convicilllin (Newbigin et al., *Planta* 180: 461 (1990)), pea legumin (Shirsat et al., *Mol. Gen. Genetics* 215: 326 (1989)), rapeseed napin (Radke et al., *Theor. Appl. Genet.* 75: 685–694 (1988)), as well as genes from monocotyledonous plants such as for maize 15-kd zein (Hoffman et al., *EMBO J* 6: 3213–3221 (1987)), barley β-hordein (Marris et al., *Plant Mol. Biol.* 10: 359–366 (1988)), and wheat glutenin (Color et al., *EMBO J.* 6: 3559–3564 (1987)). Moreover, promoters of seed-specific genes operably linked to heterologous coding regions in chimeric gene constructions also maintain their temporal and spatial expression pattern in transgenic plants. Such examples include Arabidopsis thaliana 2S seed storage protein gene promoter to express enkephalin peptides in Arabidopsis and Brassica napus seeds (Vandekerckhove et al., *Bio/Technology* 7: 929–932 (1989)), bean lectin and bean β-phaseolin promoters to express luciferase (Riggs et al., *Plant Sci.* 63: 47–57 (1989)), and wheat glutenin promoters to express chloramphenicol acetyl transferase (Colot et al., *EMBO J.* 6: 3559–3564 (1987)). Promoters highly expressed early in endosperm development are most effective in this application. Of particular interest is the promoter from the a subunit of the soybean β-conglycinin gene (Walling et al., *Proc. Natl. Acad. Sci. USA* 83: 2123–2127 (1986)) which is expressed early in seed development in the endosperm and the embryo.

The cell disruption gene used can be selected from a group of genes encoding products that disrupt normal functioning of cells. There are many proteins that are toxic to cells when expressed in an unnatural situation. Examples include the genes for the restriction enzyme EcoRI (Barnes and Rine, *Proc. Natl. Acad. Sci. USA* 82: 1354–1358 (1985)), diphtheria toxin A (Yamaizumi et al., *Cell* 15: 245–250 (1987)), streptavidin (Sano and Cantor, *Proc. Natl. Acad. Sci. USA* 87: 142–146 (1990)), and barnase (Paddon and Hartley, *Gene* 53: 11–19 (1987)). Most preferred for this system is the coding region of barnase which has been shown to be highly effective in disrupting the function of plant cells (EPA 83-344029).

A highly desirable seedless system is one in which fully fertile F1 seed develops, that can then be grown into plants that produce only seedless fruit. This system is economically favorable in that for each cross pollination, a large number of seedless fruits result: the number of F1 seed from one cross X the number of fruits produced on an F1 plant. Also incorporated in this scheme are the advantages of growing a hybrid crop, including the combining of more valuable traits and hybrid vigor. This is accomplished in the same manner as described above except that the recombination site/polyA-inactivated disruption gene is expressed from a seed maternal tissue (seed coat or nucellus)-specific promoter. For example, the seed coat is the outgrowth of the integuments, a strictly material tissue. Therefore the hybrid cross that brings the recombination site/poly A-inactivated disruption gene together with the recombinase gene does not involve this seed coat tissue. The seed coat of the F1 seed has either recombination sites or recombinase, depending on which is used as the female parent, and thus F1 seed develop normally. After the F1 seed gives rise to a fruit-bearing F1 plant, all vegetative cells (including seed coat cells) inherit both recombination sites and recombinase from the embryo. Thus the seed coat of the F1 plant has an activated cell disruption gene.

The seed coat is an essential tissue for seed development and a viability. When the seed is fully matured, the seed coat serves as a protective layer to inner parts of the seed. During seed development, the seed coat is a vital nutrient-importing tissue for the developing embryo. The seed is nutritionally "parasitic" to the mother plant. All raw materials necessary for seed growth must be imported. In seeds of dicotyledonous plants, the vascular tissue enters the seed through the funiculus and then anastamoses in the seed coat tissue. There is no vascular tissue connection or plasmodesmata linkage between the seed coat and the embryo. Therefore, all nutrient solutes delivered into the developing seed must be unloaded inside the seed coat and then move by diffusion to the embryo. Techniques have been developed to study the nutrient composition in the seed coat (Hsu et al., *Plant Physiol.* 75: 181 (1984); Thorne & Rainbird, *Plant Physiol.* 72: 268 (1983); Patrick, *J. Plant Physiol.* 115: 297 (1984); Wolswinkel & Ammerlaan, *J. Exp. Bol.* 36: 359 (1985)), and also the detailed cellular mechanisms of solute unloading (Offler & Patrick, *Aust. J. Plant Physiol.* 11: 79 (1984); Patrick, *Physiol. Plant* 78: 298 (1990). It is obvious that the destruction of this vital nutrient-funneling tissue causes seed abortion.

The disclosed tissue-specific and site-directed DNA recombination can be used to obtain seedless fruit production. This method is useful for the production of seedless watermelon, for example. A combination of gene expression specific for maternally inherited seed tissue and the disclosed recombinase system can be used for the production of seedless watermelon. The system can be universally applied to any horticultural crop in which the presence of seeds is undesirable and difficult to be eliminated through conventional breeding methods. The system also allows the normal production of F1 seeds. The ability to maintain heterosis is an advantage of producing F2 seedless fruits.

The existing production of seedless watermelon indicates that seed development is not essential for the watermelon fruit development. However, conventional production of seedless watermelon using the ploidy imbalance trick has never been very popular due to the difficulty of overcoming the yield and production problems. Creating and maintaining the tetraploid (4n) female germline, and producing the triploid (3n) seeds have made the seed cost high. Cross-pollination is needed for the production of triploid seeds (4n×2n) and seedless fruits (3x×2n). Also triploid seed germination is usually poor due to ploidy imbalance.

The present approach eliminates the dependence on polyploid germlines and provides an efficient system for producing seedless fruit. The products of double fertilization of higher plants are the embryo and endosperm. The seed coat (including the integumentary tapetum) and nucellus (the tissue encompassing the embryo sac) are the remaining seed tissues that are maternally inherited. In addition to general protection, the seed coat and nucellus also play an important role in importing nutrients into the developing embryo and endosperm. Seed development will be aborted if this vital nutrient-importing mechanism of the seed coal/nucellus is debilitated. This will be accomplished by using the recombinase system to activate a cell-damaging gene only in these tissues. Controlling the gene activation in a maternal tissue-specific manner allows production of normal F1 seed, but abortion of F2 seed. A seed coat or nucellus promoter is coupled to a tissue-destructive (lethal) gene in order to prevent seeds from forming. The destructive gene is inactive in the seed parent due to the presence of a blocking transcription terminator. The terminator is flanked by recombination sites for subsequent excision by a recombinase-mediated recombination event. Expression of the recombinase is also controlled by the seed coat/nucellus-specific promoter. When plants carrying the separate recombinase and recombination site constructs are crossed, the F1 seed will be viable because seed coat/nucellus is maternal tissue, and in that tissue recombinase and recombination sites are not combined. When the F1 seed is used as planting seed, the self-pollinated or out-crossed plants will produce seedless fruits or vegetables, since in seed coat/nucellus tissues recombinase and recombination sites are combined, and the lethal gene is activated.

2. Use of Variant Recombinases for Phage Packaging

The disclosed variant recombinases can also be used to aid in phage packaging. The cloning system described herein utilizes a headful in vitro packaging system to clone foreign DNA fragments as large as 95 kb which permits the isolation of DNA fragments that are at least twice the size of those that can be obtained by lambda cosmid cloning. This increased cloning capacity has the following utility:

(1) Genes in the 45–95 kb size range and, more particularly, in the 70–95 kb size range can now be directly cloned and genes in the 25–45 kb size range can be cloned more easily.

(2) Chromosomal "walking" and "jumping" techniques can be speeded up by a factor of at least two and should be more accurate because of the reduced number of contiguous segments that need to be linked together.

(3) The cloning system of the invention is useful as a means for the delivery of DNA efficiently to bacteria which otherwise do not take up DNA from solution well.

Specifically, the headful packaging system of this invention for cloning foreign DNA fragments as large as 95 kb comprises:

(a) modifying vector DNA by inserting a stuffer fragment into a blunt end producing site which is proximal to a pac site;

(b) digesting the product of step (a) to produce two vector arms each of which contains (i) a blunt end, (ii) another end which is compatible with the foreign DNA fragment which is to be cloned, and (iii) a recombination site;

(c) ligating the foregoing DNA to the product of step (b) without generating concatemers;

(d) reacting the product of step (c) with pac cleavage proficient extract and head-tail proficient extract wherein the ratio of large heads to small heads in the head-tail extract is at least 5;1;

(e) infecting a bacterial strain expressing a variant recombinase with the product of step (d); and (f) recovering the cloned DNA.

The term pac is a generic name which refers to the site needed to initiate packaging of DNA. The pac cleavage proficient extract contains the recognition proteins necessary to cleave the pac site and, thus, initiate packaging. The head-tail proficient extract contains the heads and tails needed to package the cloned DNA into a virus particle. The term concatemer means a DNA molecule consisting of repeating units arranged in a heat-to-tail configuration. The term stuffer fragment refers to a DNA fragment which is inserted into the vector DNA at a unique site, and within which headful packaging is terminated. The terms bacteriophage and phage are used interchangeably herein.

Although many of the elements described herein pertain to the P1 bacteriophage cloning system, those skilled in the art will appreciate that, with the exception of the components needed to package DNA (pac and packaging extracts), many of the elements discussed below, such as plasmid replicon and a multicopy or lytic replicon, pertain to the recovery of packaged DNA and can be used to recover DNA in bacteria, such as $E.\ coli$, with other cloning systems, for example, bacteriophage, yeast, etc.

Bacteriophages which are suitable to practice the invention must have a large head capacity and the elements necessary for packaging DNA must be defined. For example, for phages P22 and T1, which utilize headful packaging, the necessary packaging elements are defined. However, P22 and T1 do not have a very large head capacity. On the other hand, for phage T4, which has a large head capacity, the necessary packaging elements have not been defined.

The elements necessary for packaging DNA (i.e., an in vitro headful packaging system) are the following:

(1) a unique site, pac, which is cleaved by recognition proteins; it is the pac cleavage proficient extract which contains the recognition proteins necessary to cleave the pac site; and (2) empty phage heads into which the DNA is packaged until the head has been completely filled, then a cleavage event is triggered (the "headful" cut) which separates the packaged DNA away from the remaining components; it is the head-tail proficient extract which contains the heads and tails needed to package the cloned DNA into virus particle.

Although initiation of packaging is site-specific (cleavage of pac site initiates packaging), termination of packaging is not site-specific. In other words, no unique site is recognized, as packaging will terminate at whatever point the head has been filled.

In the case of P1, the DNA substrate used in the packaging reaction during the viral life cycle is a concatemer consisting of individual units of the P1 chromosome arranged in a head-to-tail manner. Headful packaging, using either P1 phage or any other phage, is a four step process: (1) In the first step a unique site, pac, is recognized and cleaved by the pac recognition proteins (PRPs); (2) DNA on one side of the cleavage is packaged into an empty phage head until the head has been completely filled; (3) a second cleavage event is then triggered (the "headful" out) that separates the packaged DNA away from the rest of the concatemer; and (4) initiation of a second round of DNA packaging from the free end generated by the previous "headful" cut-hence the term processive headful cutting. However, if a concatemer is not generated then processive headful packaging does not occur.

The ends of the packaged P1 DNA do not contain complementary single-stranded sequences, as do the ends of packaged bacteriophage lambda DNA, and consequently after P1 DNA is injected into a bacterium its cyclization does not occur by strand annealing but rather by recombination between homologous sequences present at the ends of the molecule. Because of this circumstance, any vector that uses P1 packaging, or for that matter any headful packaging mechanism, must devise a means of cyclizing the linear packaged DNA by recombination. Cyclizing is accomplished by incorporating recombination sites into the vector and using a disclosed variant recombinase to cyclize the DNA after injection into gram-negative bacterial strains expressing the variant recombinase.

P1 produces two head sizes, a big head that can accommodate 105–110 kb of DNA, and a small head that can accommodate no more than 45 kb of DNA. Normally the ratio of big to small heads in a P1 wild-type infection is 10:1, however, in the cm-2 mutant of P1 used to prepare some of the packaging lysates described herein, the radio of head sizes is 1:1. The head-tail packaging lysate prepared from the cm mutant of P1 contained the usual ratio of bit to small heads which is about 10:1. This is the preferred lysate for preparing head-tail packaging extract. To ensure packaging of DNA exclusively into the big phage heads, the DNA must be bigger than that which can be accommodated by the small heads. It is generally desired that there be a large excess of big heads. However, the ratio of large heads to small heads should not fall below a ratio of about 5:1.

ILLUSTRATION

The following illustration describes an example of how the disclosed method can be used to generate variant FLP recombinase with altered site specificity. As with other recombinase, the method preferably uses the following components:

1. An in vitro mutagenesis system;

2. A recombinase expression plasmid that allows varying levels of expression by a simple environmental control (for example, by the presence of varying amounts of an inducer substance in the growth media, by temperature, or by osmolarity);

3. An indicator/selector bacterial strain. The strain carries both an indicator recombination substrate for detection of recombination at the wild type recombination site and a second recombination substrate that allows selection for recombinase mutants that have gained the ability to recognize and perform recombination at a target mutant recombination site (that is, a variant recombination site). Importantly, the wild type and target mutant sites are designed so that recombination between the mutant and wild type sites is blocked even with a mutant recombinase that can recognize both the wildtype site and also the target mutant site. This design prevents unwanted recombination between the wild type and target mutant recombination sites that could interface with either selection or detection of desired recombinational outcomes. The block is imposed by designing the wild type and mutant sites to have different spacer regions (that is, different compatibility sequences), for example, the normal "wt" spacer for the wildtype recombination site, and an alternative spacer "A1" for the other recombination substrate. In an otherwise nonmutant recombination site DNA recombination proceeds efficiently both for recombination sites having the wt spacer (that is, a recombination between two wt sites) and also for sites having the A1 spacer (that is, a recombination between two A1 sites). yet, recombination between the A1 site and the wt site is blocked (that is, recombination between a wt site and an A1 does not occur). This strategy is applicable to all recombinases that have a recombination target site displaying one or more recombinase binding sites (repeat elements) on each side of a spacer region in which recombination occurs (Nunes-Döby et al., Nucl. Acids Res., 26:391–406 (1998)). Such sites display a requirement for homology in the spacer elements for optimal recombination activity and has been shown to be the case for members of the Int family of recombinases, including Cre, lambda Int. and FLP (Craig, Ann. Rev. Genet 22:77–105 (1988)).

The preferred in vitro mutagenesis system is that of Stemmer (Stemmer, Nature 370:389–391 (1994)), or a variant of that strategy. After mutagenesis and assembly of fragments into a full-length FLP gene, it is cloned into the expression vector.

The expression plasmid to be used can be any of the "inducible" expression plasmids available in bacteria. For this illustration one of the pBAD plasmids for E. coli was chosen that allows expression of recombinase by growth on arabinose (Guzman et al., J. Bacterial. 177:4121–4130 (1995)), and which can be turned off by growth on glucose (and no arabinose). For this illustration the expression plasmid carries the replication origin of pACYC, and the FLP recombinase gene is under the control of the E. coli ara promoter region. In addition, the plasmid carries the selectable marker Cm' which confers resistance to the antibiotic chloramphenicol. Because the pACYC replicon is low copy, its use may be advantageous in preventing excessive expression of FLP. Alternatively, a higher copy replicon could be used, such as that of ColE1. In that case the expression level of FLP must also be carefully controlled using the inducer substance arabinose.

The indicator/selector bacteria carries two different reporter constructs for FLP-mediated recombination. The first reporter construct consists of two FRT sites (FLP recominbation target; that is, the recombination site recognized by FLP recombinase) in direct orientation (an excision substrate) and resides on a low copy replicon that is compatible with the FLP expression construct. In this example the first substrate is integrated into the E. coli genome. This can be done by incorporating the FRT substrate onto phage lambda and then constructing a lambda lysogen. Alternatively the FRT substrate could reside on a low-copy replicon that is compatible with that of the FLP expression vector and which has an additional selectable marker, for example resistance to bleomycin. This FRT substrate carries two FRT sites in direct orientation flanking a gene whose presence can be easily monitored. In this illustration a constitutively expressing lacZ gene was used whose presence can be determined simply by growing colonies plates containing X-gal, upon which they will become blue in color. Loss of the lacZ gene by FLP-mediated recombination results in white colony formation on X-gal plates.

The indicator/selector bacterial strain also carries a second FRT-like substrate. This is a plasmid element having two FRT-M sites in direct orientation flanking DNA sequences (STOP) that disallow expression of a downstream selectable marker. In this example, nonexpression of the selectable marker is achieved by placing genetic elements in the following order: constitutive promoter—FRT-M—STOP—FRT-M—'neo, where 'neo indicates the promoterless neo gene of Tn5. Hence this cassette cannot express neo and cells are sensitive to the antibiotic kanamycin. Excision of STOP by recombination at FRT-M is designed to permit expression of neo so that cells now become resistant to kanamycin. The plasmid carries an additional selectable marker, Ap' conferring resistance to ampicillin, to maintain presence of the plasmid in E. coli. The STOP sequence here is the strong transcriptional terminator rrnBT1T2 (Liebke et al., Nucleic Acids Res. 13:5515–5525 (1985)).

Figure 17:
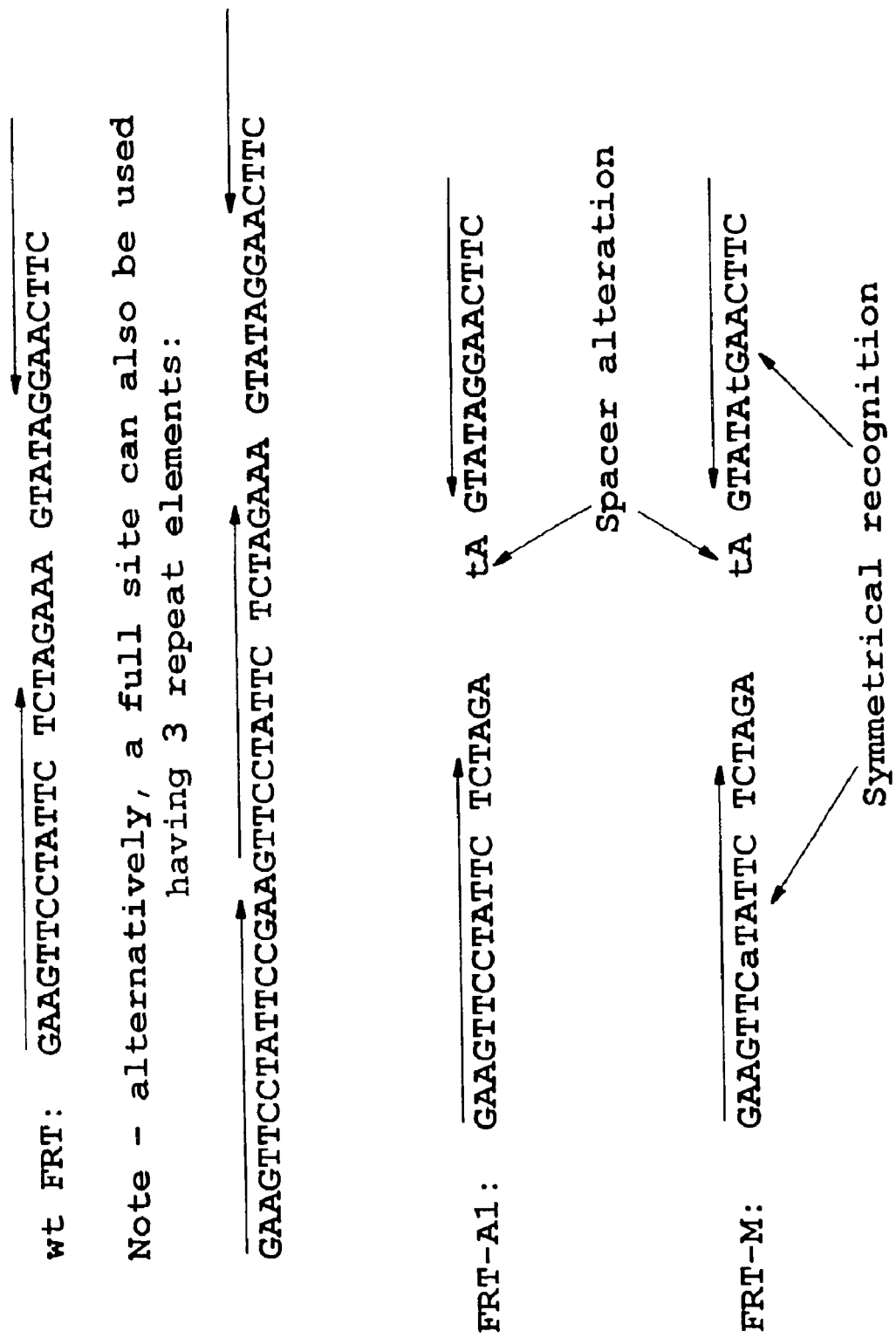
FIG. 17 shows wildtype and target FRT sites (SEQ ID NO:60–66).

FIG. 17 shows wt FRT, FRT-A1, and FRT-M sites used in this illustration. Although the wildtype FRT site displays three inverted repeat elements, recombination proceeds efficiently with sites carrying two of these repeats in the inverted configuration shown (Jayaram, Proc. Natl. Acad. Sci. USA 82:5875–5879 (1985)). Either the full or minimal site can be used since both are recombinationally functional. The FRT-A1 site is designed to have an altered spacer but which is still functional for self X self recombination (Senecoff et at., J. Biol. Chem. 261:7380–7386 (1986)). The target FRT-M site is designed to carry symmetrical mutations in the repeat elements that disallow efficient FLP-mediated recombination (Senecoff et al., J. Mot. Biol. 201:405–421 (1988)), and also the spacer mutation of FRT-A1.

Importantly, the FRT-M site differs from the FRT site in two ways. First, both of the 13 bp inverted repeat elements (that is the recognition sequences) are mutated in a symmetrical manner such that the wt FLP enzyme does not catalyze recombination between two FRT-M sites, or does so only extremely poorly (<0.1%). Second, the spacer region (that is, the compatibility sequence; the 8 bp region between the 13 bp inverted repeats) is replaced with an alternate spacer A1. The alternate spacer when present in an otherwise wt FRT site, which we will call FRT-A1, is permissive for FLP-mediated recombination between two FRT-A1 sites, but does not permit recombination between FRT-A1 and FRT. Use of the FRT-M site which contains the heterologous spacer prevents FLP-mediated recombination between FRT and FRT-M by FLP or a mutant FLP protein that might otherwise catalyze recombination between the wt FRT substrate and the mutant target FRT-M substrate. Unwanted recombination between the wildtype and target mutant recombination sites would decrease efficiency of the selection procedure by (a) not limiting recombination at the target mutant site specifically to these sites and thus compromising the selection (at FRT-M sites) for mutant FLP recombinases, (b) affecting the accuracy of the specific indication of activity at the wt FRT sites, and (c) decreasing either the plasmid stability of the FRT-M selector substrate or the integrity of bacterial chromosome (or compatible plasmid) carrying the wt FRT sites.

Figure 18:
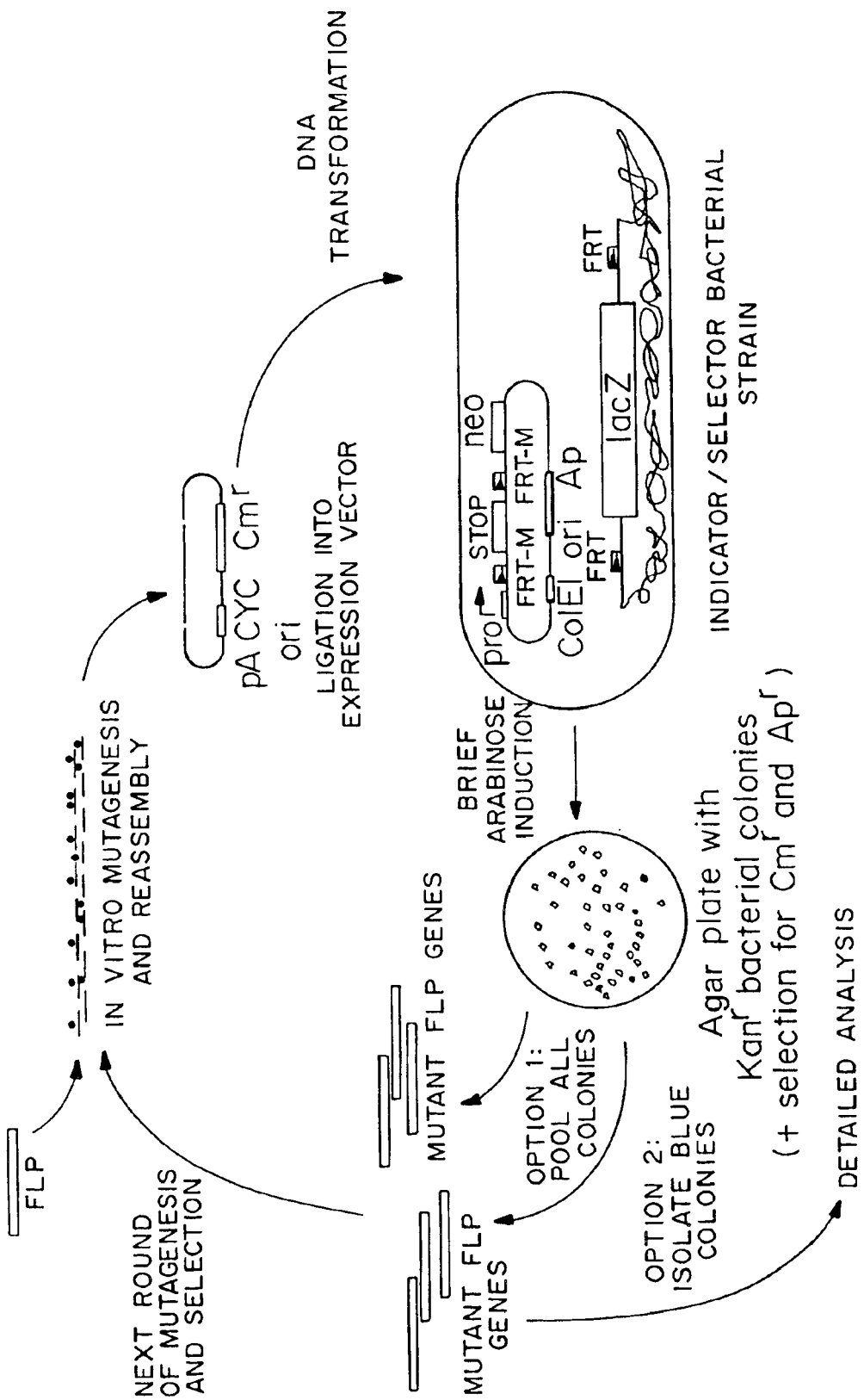
FIG. 18 shows the strategy for selection of altered specificity FLP mutants.

Procedure (FIG. 18): the FLP gene is mutagenized in vitro and then cloned into the inducible expression vector, in this case a pBAD derivative that places FLP under the control of the arabinose-inducible pBAD promoter. The pool of mutagenized FLP genes is transformed into the FRT indicator/selector strain which is pre-induced with arabinose and/or induced with arabinose during DNA transformation. Bacterial colonies are then selected to be simultaneously resistant to chloramphenicol (to retain the FLP expression plasmid), ampicillin or carbenicillin (to retain the selector plasmid) and kanamycin (to select for cells in which FRT-M X FRT-M recombination has occurred) on agar plates containing either arabinose (for continued FLP expression) or glucose (to prevent prolonged FLP expression). In some instances it may be advantageous to limit FLP expression to better enrich for those FLP mutants that either have more avidity for recombination at the FRT-M sites or to better exclude those FLP mutants that retain activity at the wild-type FRT sites. This is because prolonged or high-level FRT expression can lead to inefficient but detectable recombination at mutant sites.

Either all Kan$^r$ colonies or only those that are blue on X-gal plates are then pooled and harvested for DNA preparation. A second round of FRT gene mutagenesis and selection is then initiated by PCR amplification. Multiple rounds of mutagenesis and selection are used to obtain FRT mutants with altered site-specificity. Comparison of various individual isolates allows determination of critical amino acid residues that contribute to the desired mutant phenotype.

Figure 19:
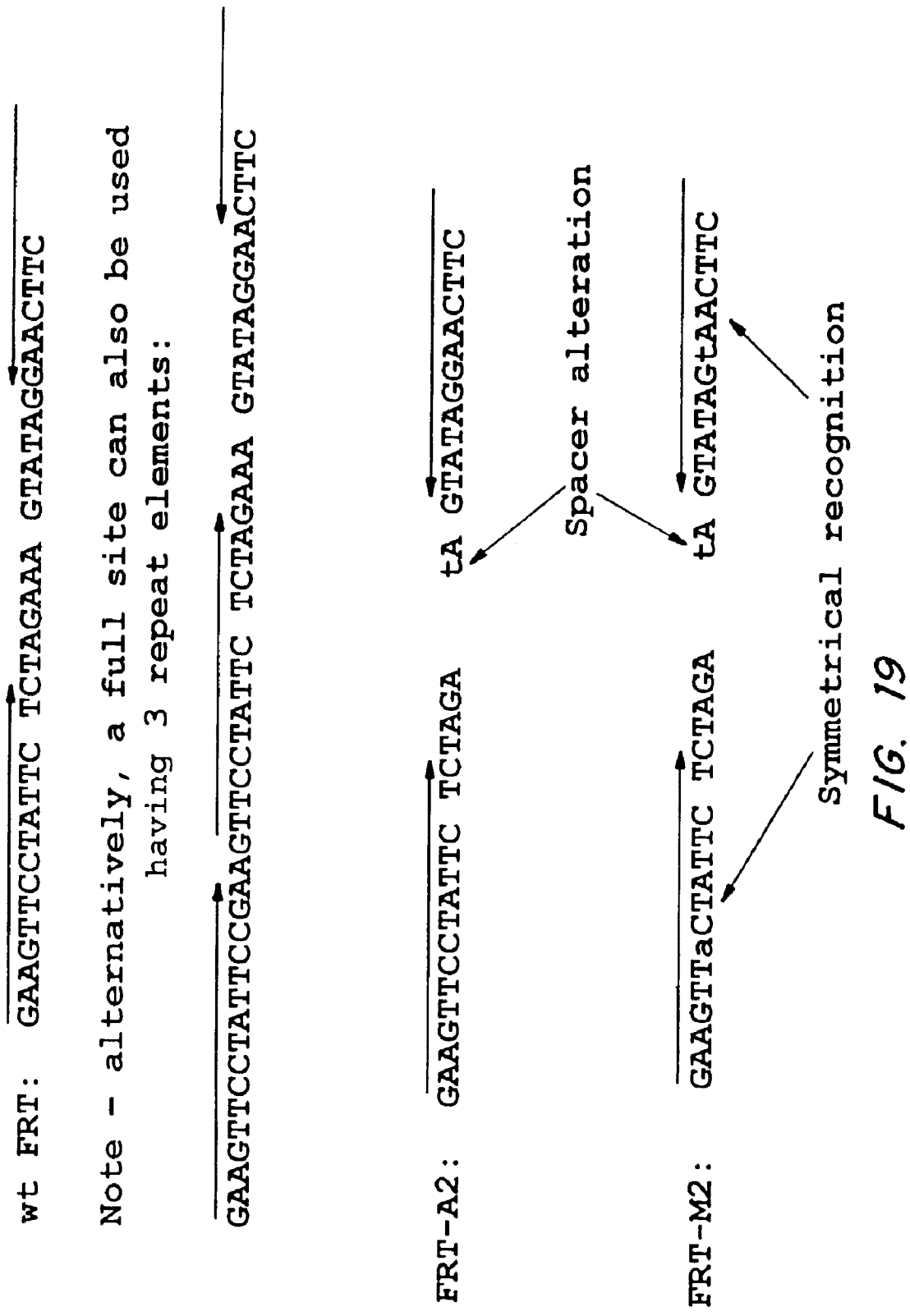
FIG. 19 shows an alternate target mutant FRT site. The design and rationale for design of the target mutant FRT site is as described in FIG. 17. (SEQ ID NO: 60–64), but the mutant FRT-M2 site differs from FRT-M by carrying a different mutational alteration in the repeat elements (SEQ ID NO: 67–68).

The same rationale and procedure can be used to generate a second class of altered FLP recombinases. The target mutant FRT site used is, however, different. In this case the target is the FRT-M2 site (FIG. 19) which carries a different binding site mutation(s) than does the FRT-M site as described above.

EXAMPLES

Example 1

Selection of Variant Cre Recombinases

The following example describes the production and analysis of some examples of the disclosed variant recombinases. Cre mutants characterized by a wider substrate recognition were created, applying a technique called directed molecular evolution: Multiple rounds of a random mutagenesis procedure (DNA shuffling, Stemmer, W. P. C., *Proc. Natl. Acad. Sci. USA*, 91:10747–10751 (1994)) and a sensitive selection for the desired phenotypes allow to accumulate candidate mutants within the generated pools of mutated sequences. The Cre mutants created in this example showed wt-like activity on loxP sites. In addition, they performed on an altered substrate, called loxK2, that is no recognized by the wt enzyme. Two transversions from adenine (loxP) to thymine (loxK2) at positions 11' and 12' of the lox sequence are the barriers that inhibit wt Cre from recognizing loxK2: The two thymines are believed to cause repulsive forces with the acidic side chain of a glutamate residue in the J helix of wt Cre (position 262). This glumtamate was found to be replaced by a glycine in all mutants with remarkably increased activity on loxK2. Additional site-directed mutagenesis experiments, confined to the glutamate at position 262 of Cre, could confirm that E262G but also E262W mutations alone are sufficient to increase loxK2 activity by a factor of $10^3$ without affecting loxP recognition. Other point mutations identified in the analyzed mutants may however be responsible for increasing the newly obtained specificity even further (10 fold compared to E262G alone).

MATERIALS AND METHODS

General Procedures

Standard Reagents

The following reagents were used in all experiments: 10×' TBE (Tris-Borate-EDTA, pH 8.3) was purchased from Biofluids, Inc. (Rockville, Md.) and diluted to 1× with deionized water prior to use. TE (Tris-HCl 10 mM, EDTA 1 mM, pH 8.0 and pH 7.5) and Tris-HCl (1 M, pH 7.5 and 8.0) came from Quality Biological, Inc. (Gaithersburg, Md.), as well as autoclaved LB (Luria-Bertani) and SOC broth. L-(+)-arabinose (>99%) was ordered from Sigma-Aldrich Fine Chemicals (St. Louis, Mo.) and anhydrous D-glucose from Mallinckrodt Laboratory Chemicals (Phillipsburg, N.J.).

Gel Electrophoresis

Figure 4:
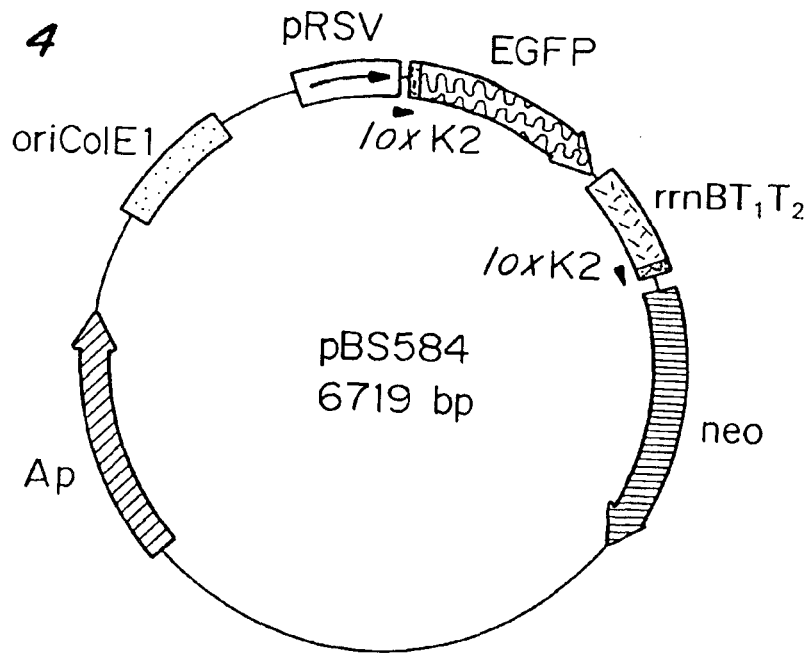
FIG. 4 is a diagram of the selection plasmid for loxK2 recombination pBS584. Recombination of two loxk2 sites by a potent Cre mutant will result in the excision of EGFP and the transcriptional terminator $rrnBT_1T_2$. Subsequently, neo transcription can take place, rendering *E. coli* resistant to kanamycin. Note that the promoter (pRSV) even though of eukaryotic origin was shown to be functional in *E. coli* (Antonucci et al., *J. Biol. Chem.*, 264:17656–17659 (1989)).

For DNA electrophoresis, 0.8% agarose TBE gels were used (GTG Sea Kern Agarose (FMC, Rockland, Me.)). Gels were prestained with 0.25 µg/ml EtBr (Ethidium Bromide, 10 mg/ml (Life Technologies, Inc., Grand Island, N.Y.)). The used electrophoresis apparatus was a DNA SUB CELL™ (BioRad, Hercules, Calif.) with an OSP 105 (OWL, Woburn, Mass.) power supply. Gels were run at 60 V (5 V/cm) as recommended by Sambrook et al., Cold Spring Harbor, New York: Cold Spring Harbor Laboratory Press (Second Edition) (1989). Occasionally, for small amounts of samples, 50 ml minigels were used under similar conditions (Hoefer HE33, Hoefer Scientific Instruments, San Francisco, Calif.). Molecular weight standards were λ/Hind III digest (Research Genetics, Huntsville, Ala.) and Ready-Load™ 100 bp DNA ladder (Life Technologies), providing a standard size range from 100 bp to 23130 bp (FIG. 4). For standard fragment purification from gel, the Geneclean II© Kit (BIO 101, Inc., La Jolla, Calif. (November 1999) was used, following the manufacturers instructions.

Minipreps and Plasmids

Plasmids for diagnostics, cloning, and sequence analysis were prepared using the Wizard™ Minipreps Plus Kit (Promega, Wizard™ Minipres Plus DNA Purification System. Instruction Manual (Madison, Wis.) (January 1996)). Useful ones were assigned a pBS number and stored in TE pH 8.0 at +4° C.

Oligonucleotides

All oligonucleotides used as NCR primers, for plasmid construction, or in the mutagenesis procedure, were ordered from Midland, Inc. (Midland, Tex.) in gel filtration (GF) quality. The lyophilized oligonucleotides were assigned a BSB number, suspended in HPLC grad water (Sigma-Aldrich) at a final concentration of 300 µM, and stored at −20° C.

DNA Digests and Ligations

All enzymes used for DNA manipulations (restriction enzymes, T4 ligase, etc.) were purchased from New England Biolabs, Inc., Catalog. (Beverly, Mass.) (1998/99) and used as recommended in the manufacturer's catalog (1998/99). Briefly, for restriction enzyme digests the total reaction volume was 20 µl with approximately 10 units (U) of enzyme. For DNA fragment ligations, 10 µl with 200 U of T4 DNA ligase were used.

*E. coli* Strains

All *E. coli* strains, except otherwise mentioned, were derived originally from DH5α: endA1 hsdR17 (rkm$_k^+$) supE44 thi-1 recA1 gyrA (Nal$^R$) relA1 Δ(laclZYA-argF) U169 deoR (M80 dlac Δ(lacZ)M15) (Woodcock et al., *Nucl. Acids Res.*, 17:3469–3478 (1989); Raleigh et al., In *Current Protocols in Molecular Biology*, eds. Ausubel, F. M. et. al. (New York: Publishing Associates and Wiley Interscience). Unit 1.4 (1989). After modification with λ prophages or plasmids, strains were catalogued by assigning them a BS number and stored at −80° C. with 10% DMSO (Dimethylsulfoxide) after overnight culture in appropriate selection medium.

Transformation of *E. coli*

For all plasmid transformations of *E. coli* strains, electroporation was preferred over chemical protocols. Elector-competent cells were made and used for electroporation as described by Smith et al., *Focus*, 12:38–40 (1990). The appropriate cell porator and cuvettes were from Life Technologies. Depending on the selection procedure after electroporation, the time in SOC medium (Smith et al., *Focus*, 12:38–40 (1990) at 37° C. under agitation (Lab-Line Orbit Environ-Shaker, Lab Line Instruments, Inc., Melrose Park, Ill.) prior to plating on selection medium was 1 h for ampicillin (Ap) and 2 h or more h for kanamycin (Kan) selection. For induction of cre expression (as described below), the transformants were cultivated in SOB (Smith et al., *Focus*, 12:38–40 (1990)) supplemented with 0.2% of L-(+)-arabinose (Sigma-Aldrich) plus 20 mM of $MgCl_2$ (referred to as induction medium) for 2.5 h and 4 h before plating on the appropriate selection media (see below). Resulting colony numbers were counted after overnight incubation at 37° C. in a gravity convection incubator (Precision Scientific, Chicago, Ill.).

E. coli Cultures

LB (as mentioned above) was used as the standard medium for all *E. coli* cultures (liquid or solid). For selection and screening, the appropriate reagents at the following concentrations were added:

TABLE 1

List of reagents used for selection and screening of *E. coli* cultures.

| Reagent | Concentration | Stock Solution |
| --- | --- | --- |
| Ampicillin (Ap) | 100 μg/ml | 50 mg/ml in $H_2O$ |
| Chloramphenicol (Cm) | 27 μg/ml | 34 mg/ml in EtOH |
| Kanamycin (Kan) | 16 μg/ml | 10 mg/ml in $H_2O$ |
| X-gal | 0.003% | 2% in DMF (w/v) |
| Z-ara | 0.006% | 2% in DMF (w/v) |

The concentration of stock solutions, stored at −20° C. and their dilutions in liquid LB medium or LB-agar plates is given. X-gal stands for 5-bromo-4-chloro-3-indolyl-β-D-galactopyranoside, and Z-ara for 5-bromo-3-indolyl-α-L-arabinofuranoside. All reagents, except Z-ara, were purchased from Life Technologies and aliquoted in the desired stock concentration for storage. Z-ara (Berlin and Sauer, *Anal. Biochem.*, 243:171–175 (1996)) was a generous gift from W. Berlin.

Ready-to-use solid LB-agar plates (2%) plain, or supplemented with Ap (100 μg/ml) were purchased from Digene, Inc. (Beltsville, Md.). For all other reagent combinations in solid medium, plates were poured according to the needs using autoclaved 2% LB agar purchased from Biofluids.

Polymerase Chain Reaction (PCR)

Standard PCR reactions were carried out in 50 μl total volume with the following reagents (all, except noted, from Perkin Elmer, Foster City, Calif.): 1× PE buffer 11 (without $MgCl_2$), 2 mM $MgCl_2$, 250 μM, of each dNTP, 0.8 μM of each primer, ca. 50 ng of template DNA, qsp. $H_2O$ (HPLC grade, Sigma-Aldrich) to 49.5 μl. For mutagenic PCR reactions (also referred to as error-prone PCR), the amount of each dNTP was reduced to 20 μM, and 0.25 mM of $MnCl_2$ added. After denaturation at 95° C. for 5 min, 0.5 μl of 5 U/μl PE Amlpi Taq Polymerase was added at approximately the annealing temperature of the primers. After mixing, the appropriate thermal cycles were carried out (as indicated individually below), using a PTC 200 thermal cycler (DNA Engine, MJ Research, Cambridge, Mass.). When finished, all PCR products immediately were loaded on an agarose gel, or separated from enzyme, nucleotides and primers by applying the Wizard™ PCR Preps Kit (Promega, Wizard™ Minipres Plus DNA Purification System. Instruction Manual (Madison, Wis.) (January 1996)). PCR products were recovered using deionized water and stored frozen at −20° C.

Sequence Analysis

Sequence analysis of plasmid constructions and cre mutants were carried out on a PE ABI PRISM™ 310 Genetic Analyzer (Perkin Elmer) according to recommendations in the manufacturer's protocol P/N 402078 Revision A (1995) for the ABI PRISM™ Dye Terminator Cycle Sequencing Kit (Perkin Elmer). Briefly, a cycle sequencing reaction contained ca. 50 ng of template DNA in miniprep quality, 4 pmol of primer, and 8 μl of the ABI Terminator Ready Reaction Mix (Perkin Elmer), in a total volume of 20 A1, and subjected to the following conditions: (96° C., 10 s; melting temperature of primer, 15 s; 60° C., 4 min) 26 times on a PTC 200 thermal cycler (MI Research). After removal of residual primers and dye by ethanol precipitation, the DNA was resuspended in 25 μl of ABI Template Suppression Reagent (Perkin Elmer) and denatured at 95° C. for 5 min before loading the ABI Genetic Analyzer. The obtained data files were examined using ABI PRISM™ Sequencing Analysis Version3.0 Software (1996, Perkin Elmer). Gene Jockey II (1996, Biosoft, Cambridge, UK) software was used for sequence comparison, translation, and alignments.

Mutagenesis Procedure

Substrate Preparation by PCR

The cre gene for the following DNase 1 shuffling reaction was amplified by PCR using 5' forward primer BSB436 (5' AAATAATCTAGACTGAGTGTGAAATGTCC 3' SEQ ID NO:8) and 3' reverse primer BSB376 (5' ATATATAAGCT-TATCATTTACGCGTTAATGG 3' SEQ ID NO:9). introducing an Xba I and Hind III cloning site, respectively (underlined). Mutagenic and non-mutagenic PCB's were carried out: (94° C., 30 s; 52° C., 30 s; 72° C., 90 s) 45 or 30 times, respectively. The 5' primer was designed to include the endogenous Shine-Dalgamo (SD) of cre, whereas its three endogenous promoters were excluded (position −17, 6; positions refer to the adenine of the start codon of the cre coding sequence as position 1). Thus, after introducing the resulting cre genes into pBAD33 (see below), expression was exclusively under control of the pBAD promoter without interference or background expression due to endogenous promoters. Including the SD sequence of cre was necessary, since pBAD33 does not contain this sequence 5' of its multiple-cloning-site (MCS). The 3' reverse primer was designed to be homologous to the 3' untranslated region (UTR) of cre (position 1057, 1032). Mutagenic events were therefore permitted in 1020 bp of the entire 1026 bp cre coding sequence, excluding the first two codons. For the first round of the directed evolution procedure. The wt cre expression plasmid pBS 185 (Sauer and Henderson, *The New Biologist*, 2:441–449 (1990)) served as template. In following cycles, the pool of mutated cre genes from the previous round was used. In all experiments, both, mutagenic and non-mutagenic PCR's were carried out in parallel using the appropriate template.

Homologous Recombination in Vitro

DNase 1 digest

Approximately 5 μg of the cre PCR product (ca. 1.1 kb) wee digested with 0.03 U of DNase 1, type IV (Sigma-Aldrich) in 20 μl total volume of 50 mM Tris-HCl pH 7.5 plus 1 mM $MgCl_2$ for 2 to 3 minutes at room temperature. After digestion, samples immediately were loaded on a 2% minigel to separate the generated fragments (FIGS. 5B and 5C) fragments of 25 bp to 300 bp were purified from the gel by DE81 (Whatman, Maidstone, GB) extraction and ethanol precipitation (Sambrook et al., Cold Spring Harbor, New York Cold Spring Harbor Laboratory Press (Second Edition) (1989)), before suspending in 5 μl of TE pH 8.0.

Self-Printing PCR

A 60 cycle non-mutagenic PCR (as described above) was carried out without added primers, allowing the fragments to prime themselves and thereby to undergo shuffling while reassembling. Conditions for PCR were: 94° C., 90 s; (94° C., 30 s; 45° C., 30 s; 72° C., 90 s) 60 times; 72° C., 10 min.

Reassembling of cre

Figure 5A:
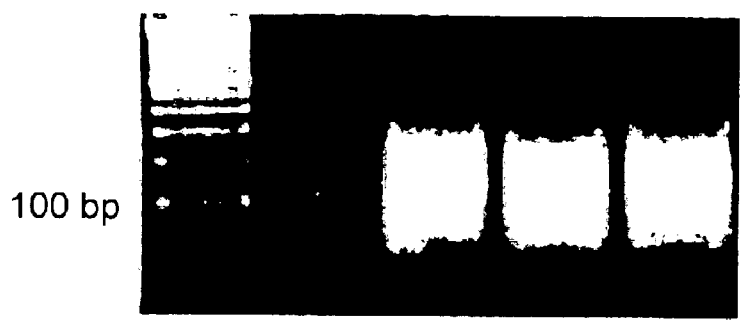
FIGS. 5A, 5B and 5C depict gels of nucleic acid fragments and PCR products generated during the DNA shuffling process.
Figure 5B:
Figure 5C:
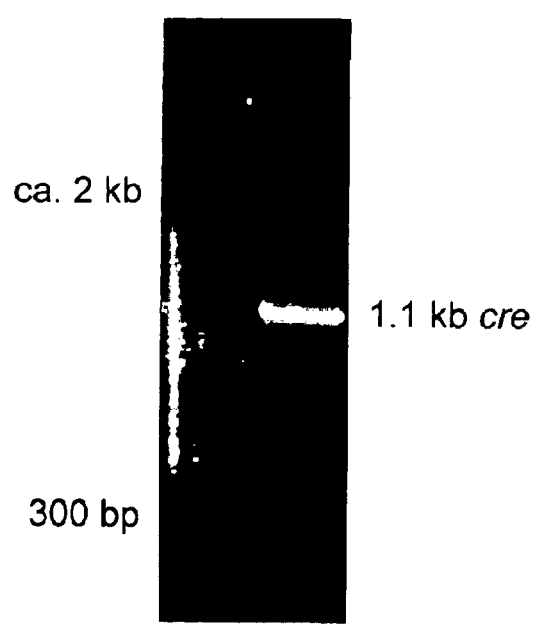

Since the self-priming step never yielded a single size product but rather a range of fragments between 300 bp to 2000 bp (FIGS. 5A, 5B, and 5C) the self-priming PCR mixture was diluted 1/40 in a non-mutagenic PCR mix with primers BSB376 and BSB436 (see above), and subjected to an additional 20 cycles (94° C., 30 s; 52° C., 30 s; 72° C., 90 s). This additional step lead to one product of 1.1 kb size (FIG. 5).

cre Expression

Figure 6:
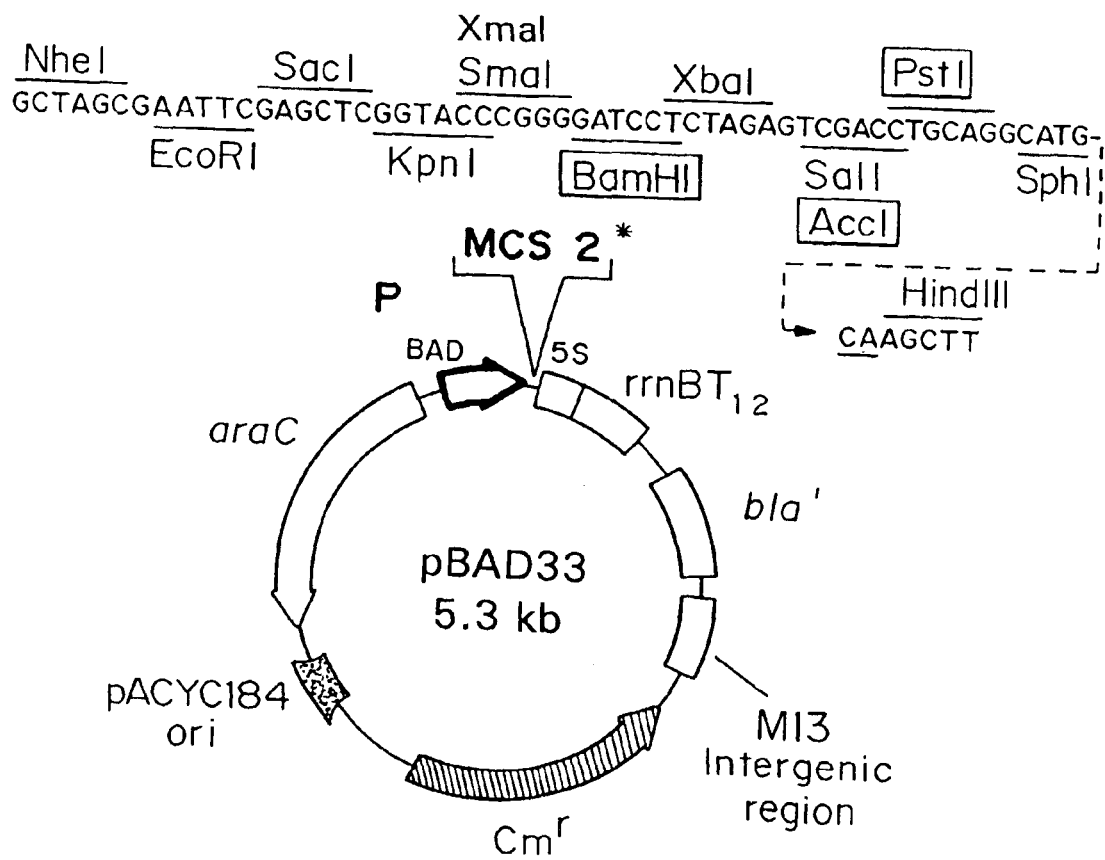
FIG. 6 is a diagram of plasmid pBAD33 used for expression of mutant cre pools (SEQ ID NO: 55).

After digesting the linkers of the generated mutant cre pool with Xba I and Hind III, the fragments were ligated into the identical sites of the MCS of the cre expression vector pBAD33 (FIG. 6). Two features favored the choice of pBAD33 as the vector to express the mutant cre pool for the selection procedure (see below): First, its pACYC184 derived origin of replication is compatible with the ColE1 derived ones of the plasmids used in the selection procedure. Second, pBAD33 contains the promoter of the arabiniose operon (pBAD), as well as expresses the regulatory protein AraC. It is therefore possible to regulate the expression of a gene cloned into the MCS and under PBAD control, from moderately high levels to nearly complete regression, by simply changing 0.2% L-(+)-arabinose in the medium to 0.2% D-glucose (Guzman et al., *J. Bacteriol.*, 177:4121–4130 (1995) and Miyada et al., *Proc. Natl. Acad. Sci. USA*, 81:4120–4124 (1984). As indicated above, the primers for cre PCR were designed in order to include the endogenous SD sequence but to exclude the three cre promoters. cre expression therefore will be under complete control of the PBAD promoter. This is important for the selection procedure (see below) that was intended for few Cre molecules acting on different lox sites. High concentrations or long term background expression of cre could eventually defeat the selection since wt Cre also catalyzes at very low frequencies recombination events between altered lox sites.

Plasmids and *E. coli* Strains Used for Selection and Screen

Mutant lox sites

FIG. 1 compares the original loxP site to the two mutant sites, loxK1 and loxK2, used during the described experiments. The lox sites with 5' Sal I and Xho I compatible, and 3' Xba I and Nhe I compatible ends were received as single stranded oligonucleotides from Midland and annealed by heating the appropriate ones together at 70° C., followed by a gradual cool down.

Plasmids for Selection and Screening

Figure 7A:
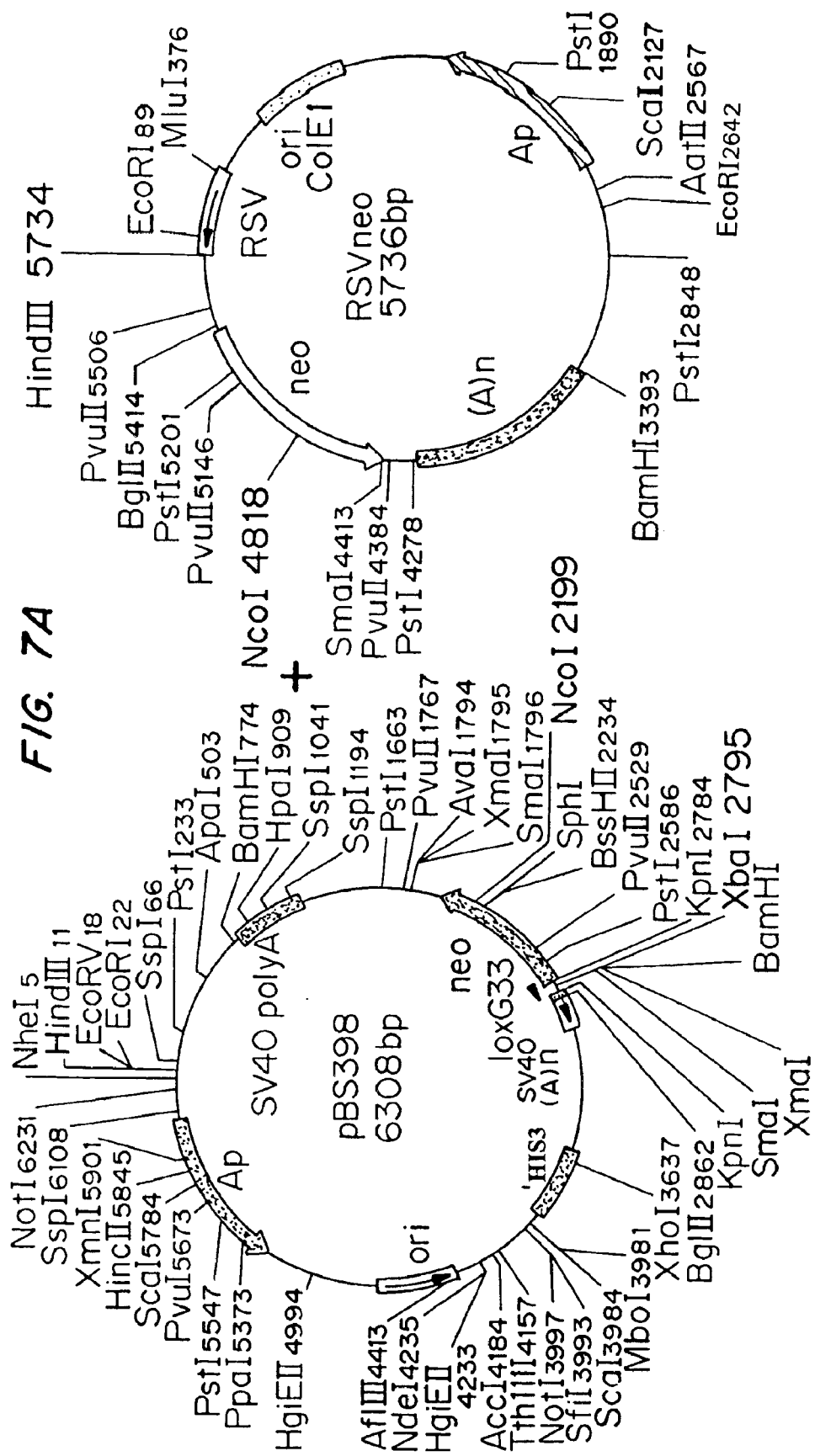
FIGS. 7A, 7B and 7C are a diagram of the construction of selection plasmids pBS568 and pBS569 (SEQ ID NO: 56–59).
Figure 7B:
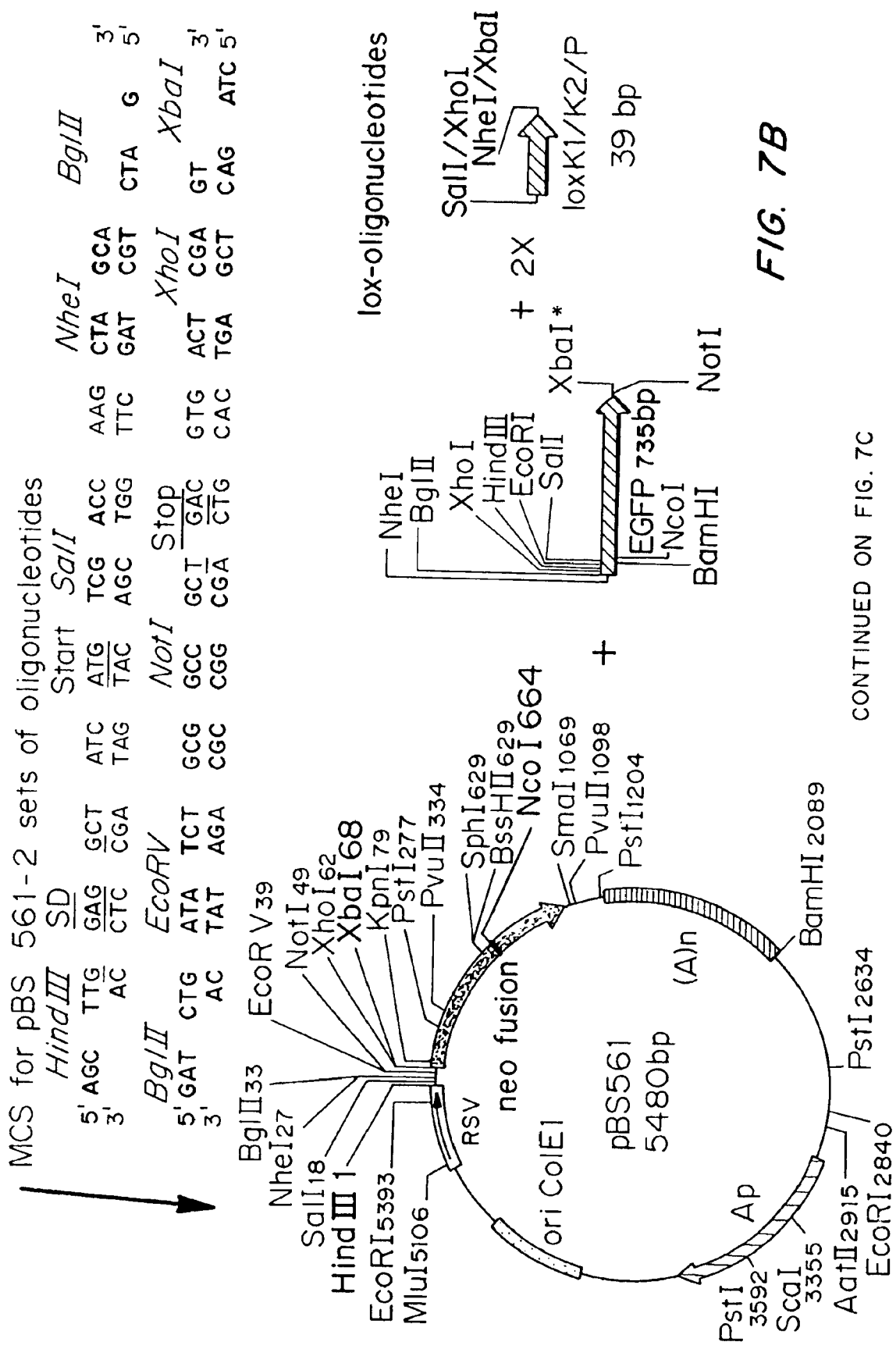
Figure 7C:
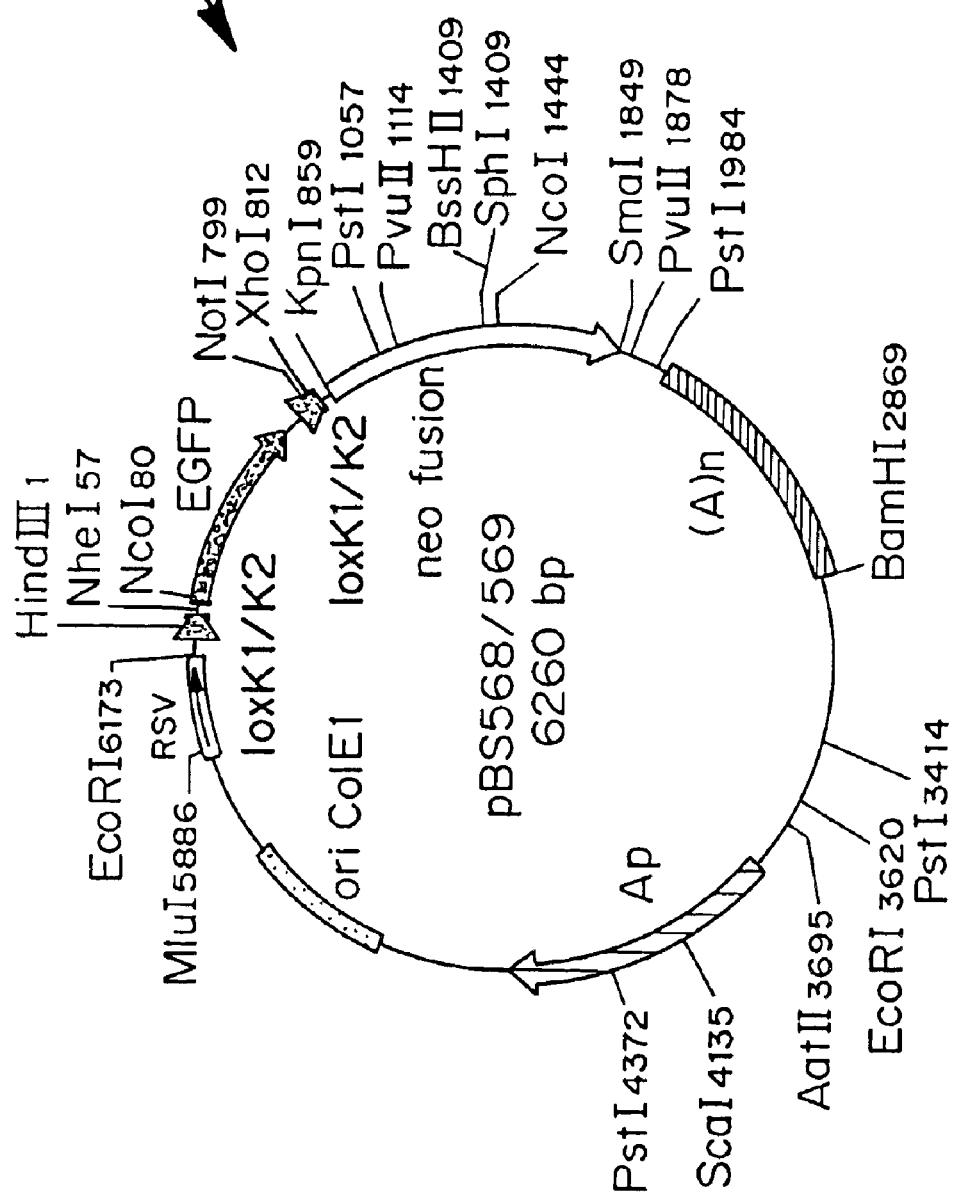
Figure 8B:
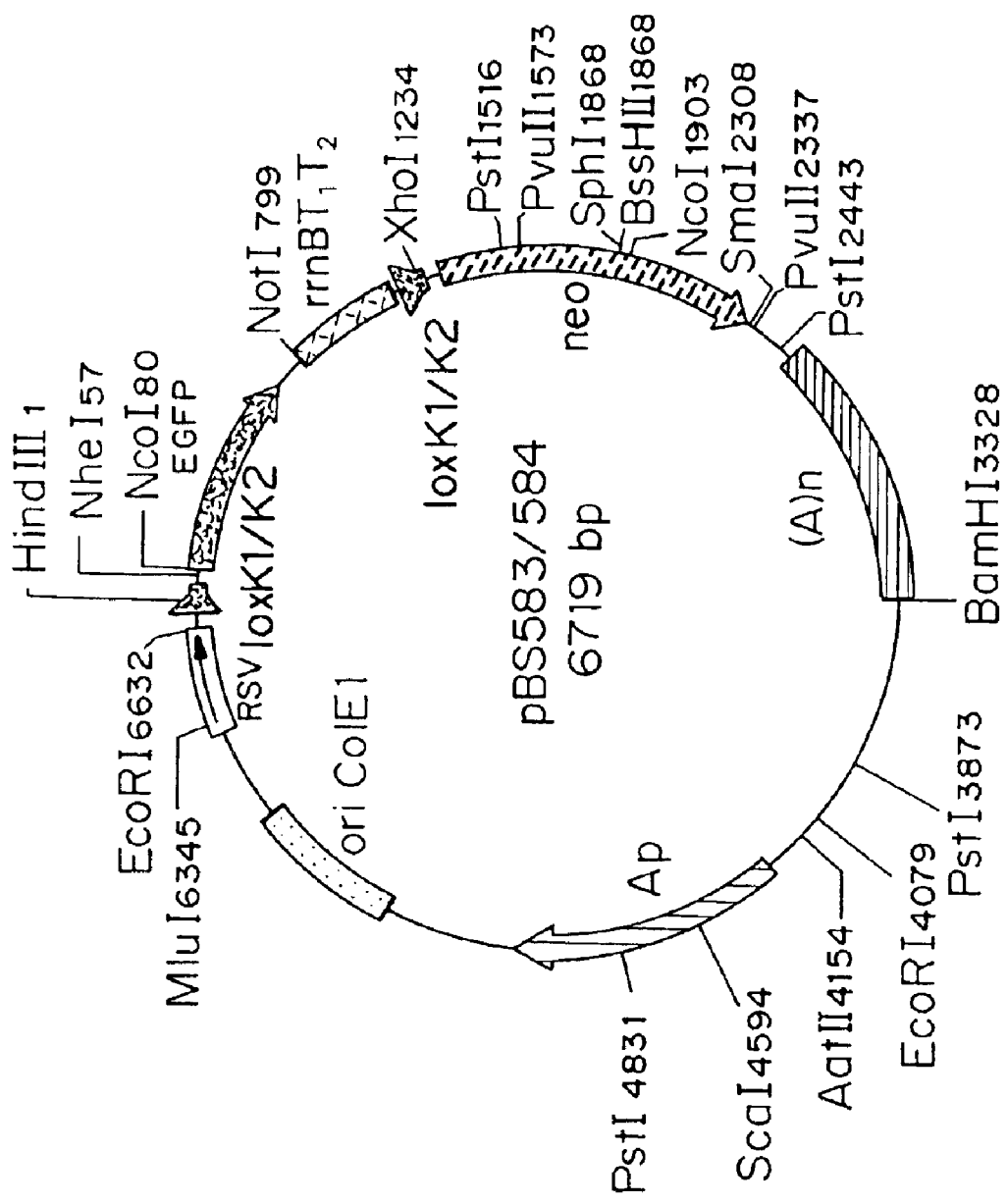

Plasmid pBS561 was constructed using three fragments: (i) the 5' modified neo gene derived from pBS398 (Sauer et al., *Methods*, 4:143–149 (1992), (ii) the RSVneo (Gorman et al., *Science*, 221:551–553 (1983) backbone without the neo gene, and (iii) the oligonucleotide-derived MCS (FIGS. 7A, 7B, and 7C). The EGFP gene derived from pEGFP-N1 (Clontech, Palo Alto, Calif.) was then inserted into the MCS along with 5' and 3' lox sites orientated in the same direction to produce plasmids pBS568 (loxK1$^2$) and pBS569 (loxK2$^2$). FIGS. 8A and 8B summarizes the procedures used to construct plasmids pBS583 and pBS584. To restore the original neo reading frame without the 5' extension, the loxK$^2$ cassettes containing Mlu 1/Kpn 1-fragments from pBS568 and pBS569 were ligated into the RSV neo backbone that contains Mlu I and Bgl II sites. The Bgl II-Kpn I junction was achieved by filling the 3' recessed end of Bgl II with Klenow (NEB) followed by a blunt-end ligation to the Kpn I end. This junction also was checked by sequencing and found to be correct. A transcriptional terminator, rrnBT$_1$T$_2$, derived from pBAD33 bp non-mutagenic PCR with primers BSB425 (5' ATAAGCGGCCGCTGAGCTTG-GCTGTT TTGGCGG 3' SEQ ID NO:10) and BSB426 (5' GCCCGTCTCGAGAGAGTTTGTAGAAACG-CAAAAAGGC 3' SEQ ID NO:11) was inserted into the loxK$^2$ cassette 3' of the EGFP gene after digest of the its Nol I and Xho I linkers (underlined). With this construct, it could be predicted that a catalyzed recombination by K1$^+$ or K2$^+$ Cre mutants between the lox sites would result in the excision of EGFP and the transcriptional terminator, and thereby permit the transcription of the neo gene due to the RSV promoter, located 5'. Expression of neo would no longer be impaired, because it is placed under control of 5' promoter elements present in RSVneo (a Kan$^R$ rendering plasmid in *E. coli*).

Figure 9:
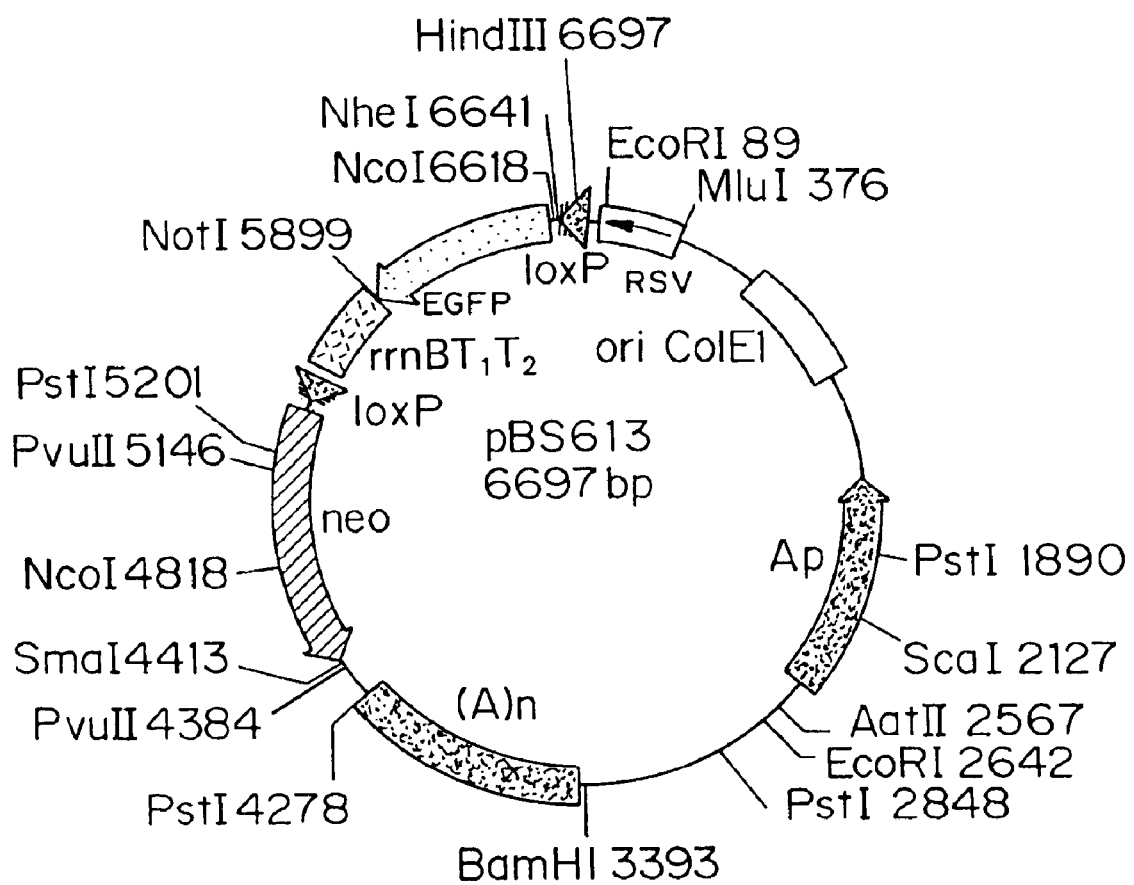
FIGS. 9 is a diagram of control plasmid pBS613.

A similar loxP$^2$ cassette selection plasmid also was designed (pBS613, FIG. 9), to be used as a control. Using this plasmid, the frequency of loxP recombination by Cre mutants could be determined in the same manner as used to evaluate loxK1 or loxK2 recombination by pBS583 and pBS584.

Figure 10A:
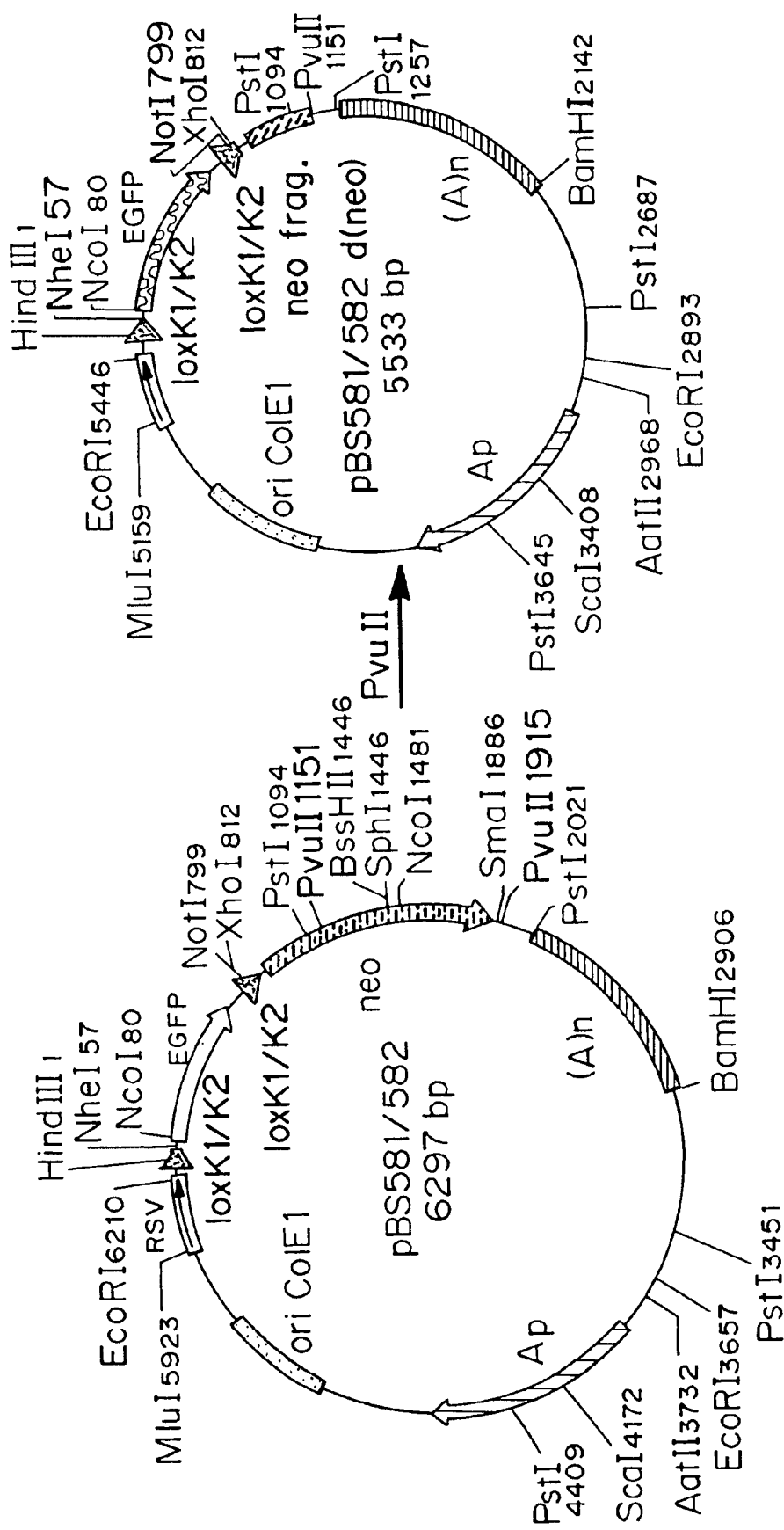
FIGS. 10A, 10B, and 10C are a diagram of the construction of screening plasmids pBS601 and pBS602.
Figure 10B:
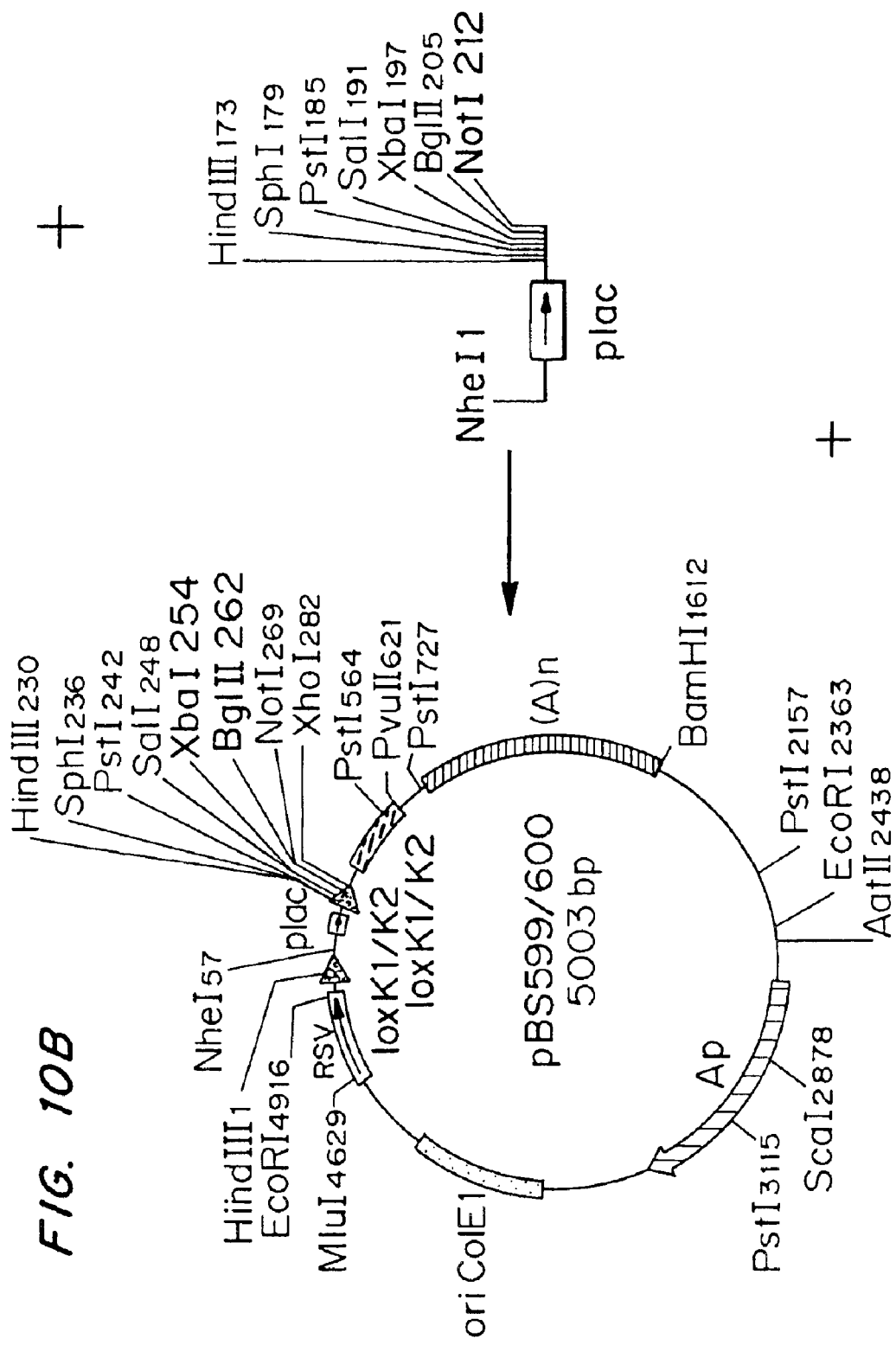
Figure 10C:
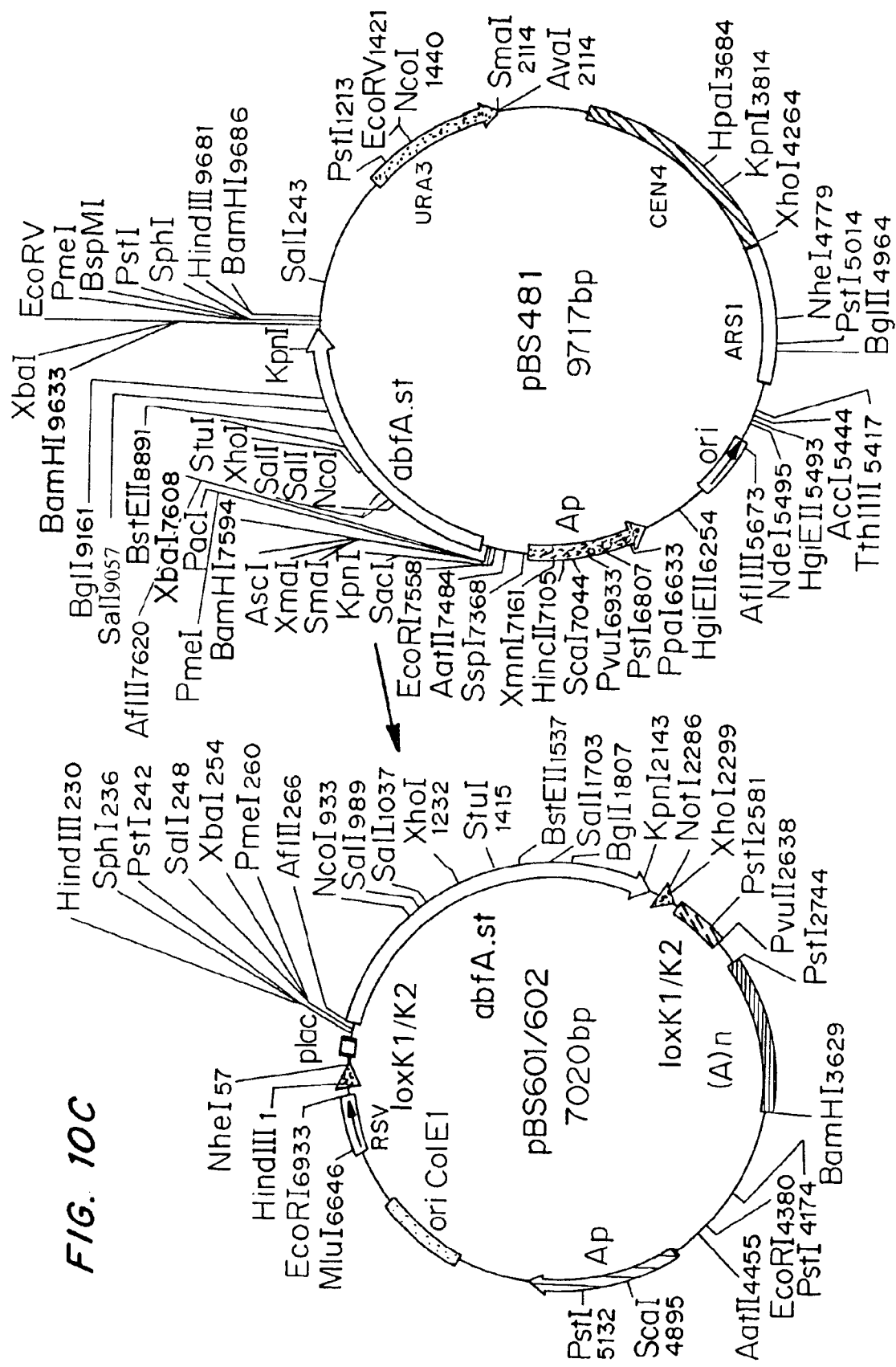
Figure 11:
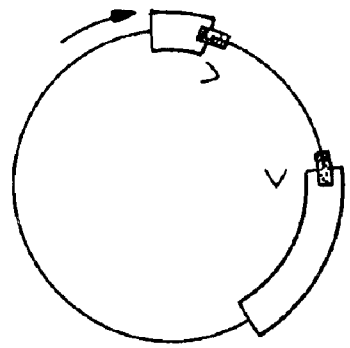
FIG. 11 is a diagram of examples of basic types of constructs useful in the disclosed method. These types of constructs are: (1) interrupted constructs where the gene is interrupted by a nucleic acid segment (which is flanked by recombination sites) that is deleted during recombination, (2) flanked constructs where the gene as a unit is flanked by recombination sites and the gene is deleted by recombination, and (3) inverted constructs where a portion of the gene is on an inverted nucleic acid segment and recombination causes the segment to invert and reconstitute the intact gene. The type of recombination is indicated in parentheses.
Figure 11:
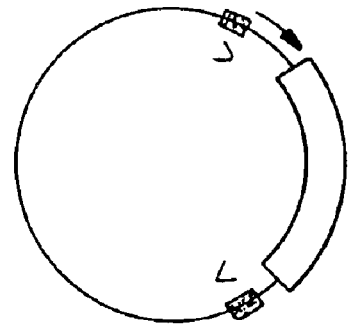
Figure 11:
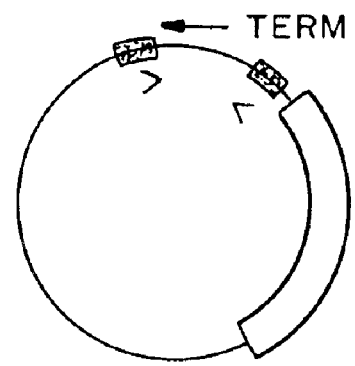
Figure 12A:
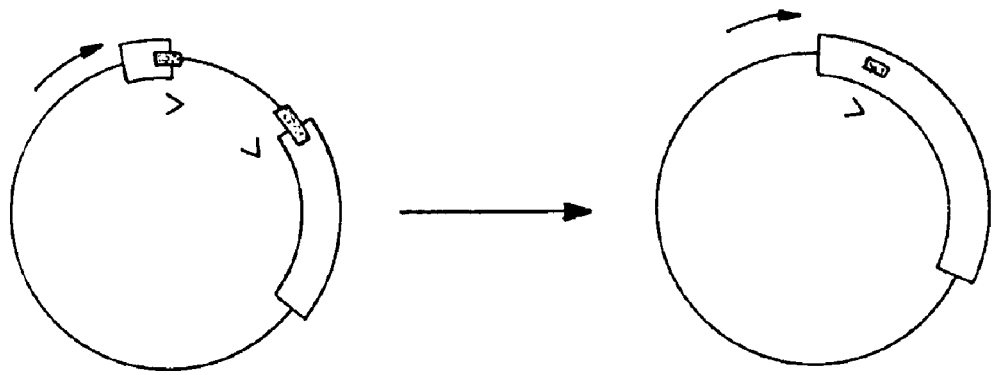
FIGS. 12A, 12B, and 12C are diagrams of examples of constructs and their expected recombination when used in the disclosed method.
Figure 12A:
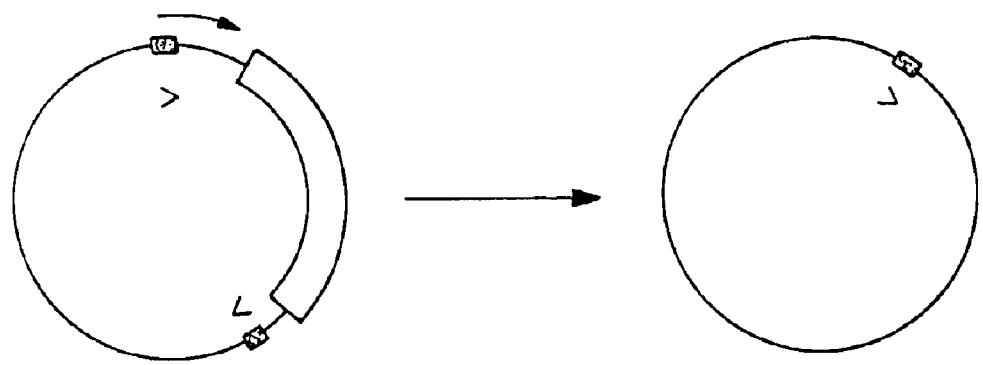
Figure 12A:
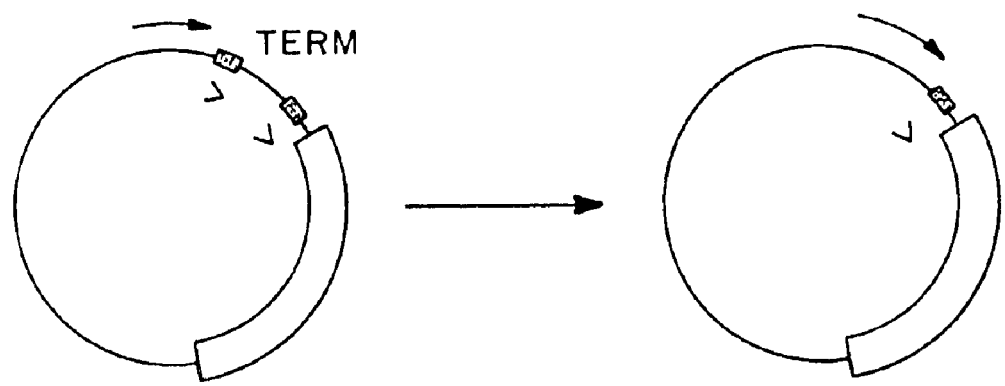
Figure 12B:
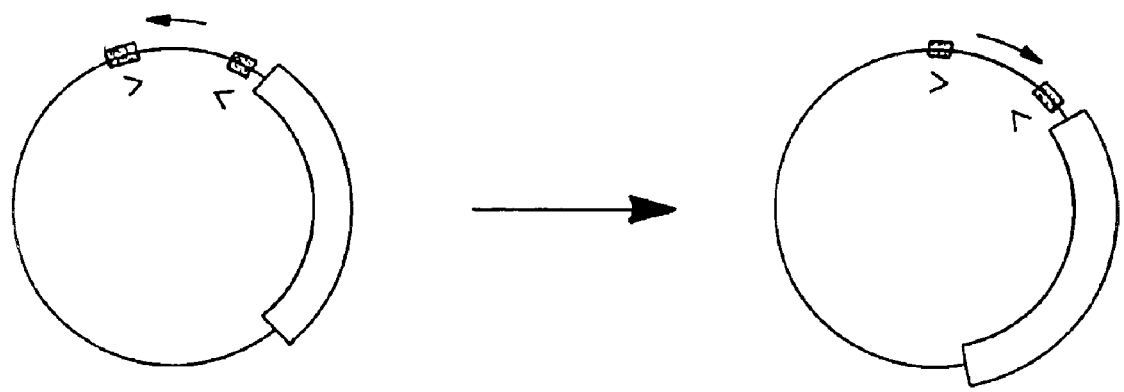
Figure 12B:
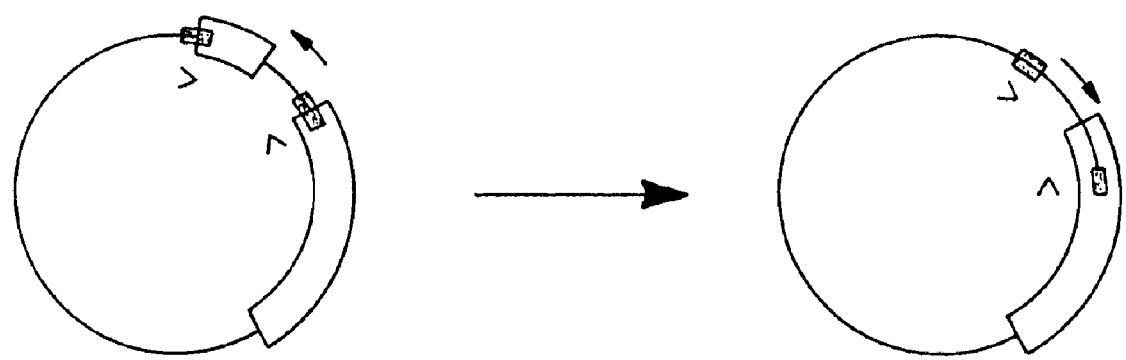
Figure 12C:
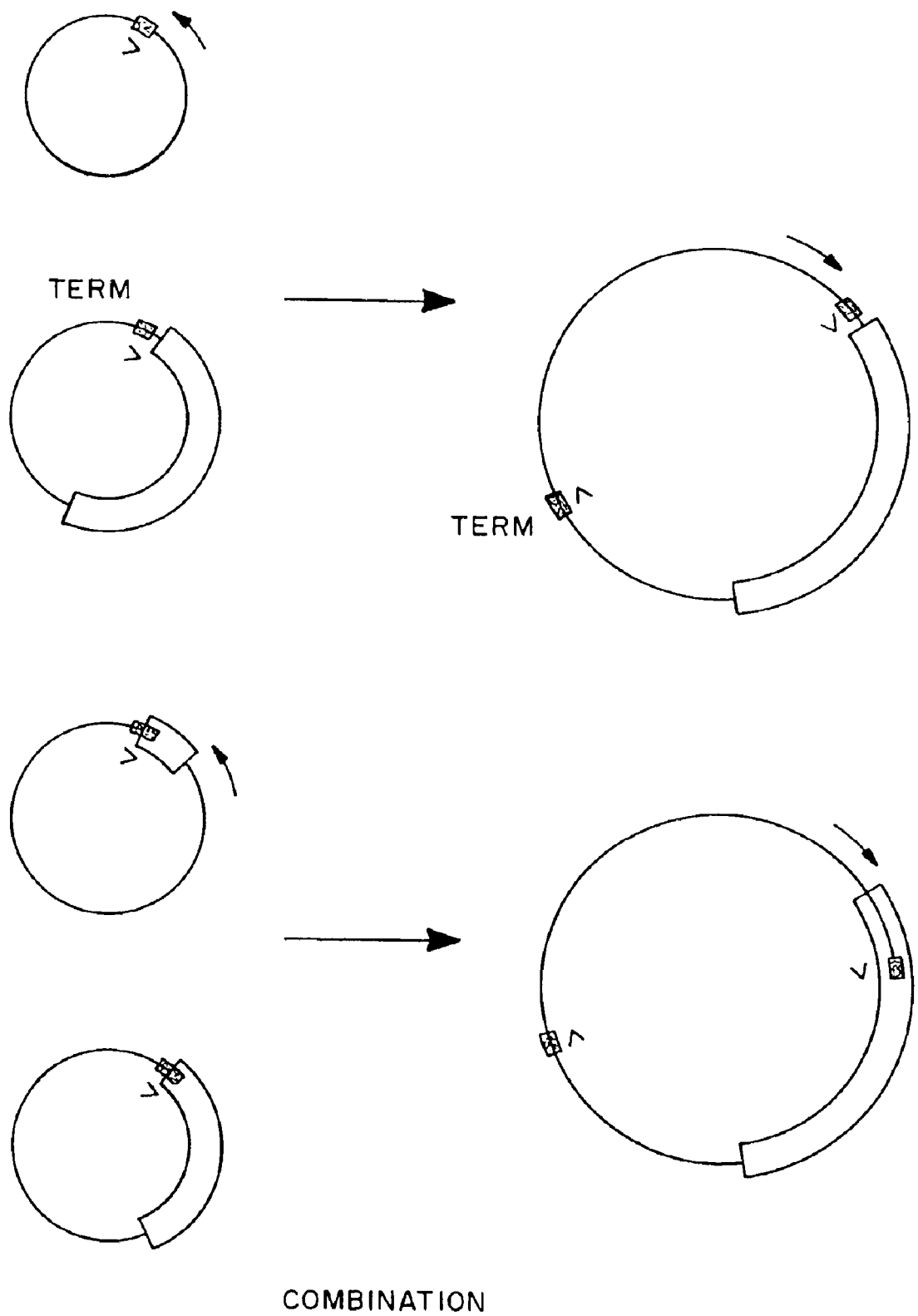

Finally, a completely different set of loxK1$^2$/K2$^2$ cassette plasmids was created. These plasmids were no longer used for selecting mutants that recognize loxK1 or loxK2, but rather were used to screen for these mutants in conjunction with a different bacterial background (see below). FIGS. 10A, 10B, 10C summarize the construction process for pBS601 (loxK1$^2$) and pBS602 (loxK2$^2$): In a first step, the neo resistance marker of pBS581 and pBS582 (intermediates in the construction of pBS583 and pBS584) was removed by deleting the Pvu II fragment and thus restoring the possibility to use neo for a different selection procedure. Following this, the EGFP gene between the lox sites was replaced by the pUC19 (Yanish-Perron, et. al., 1985) derived lac promoter with its 3' MCS. This pUC 19 fragment was obtained by non-mutagenic PCR with primers BSB448 (5' GTCAAGCTAGCTAGCAGGTTTC-CCGACTGG 3' SEQ ID NO:12) and BSB449 (5' ACAT-TGCGGCCGCAGATCTCCTCTAGAGTCGACCTG 3' SEQ ID NO:13). An Nhe I site 5', and a Bgl II and a Not 1 site 3' (underlined) were introduced thereby, which made it possible to replace the Nhe I-Not I EGFP fragment after linker digestion. The newly generated polylinker between the two lox sites permitted insertion of the Xba I-BamH I fragment of pBS481 (that carries the abfA.st marker gene) into its Xba I and Bgl II sites. As shown recently, *E coli* strains expressing a recombinant a-L-arabinofuranosidase gene from *Strepromyces lividans*-(abfA.st), can be detected by eye on LB plates containing 5-bromo-3-indolyl-α-L-arabinofuranoside (Z-ara) Berlin and Sauer, *Anal. Biochem.*, 243:171–175 (1996). This leads to the formation of an indigo blue pigment, that is similar to the classical lacZ15-bromo-4-chloro-3-indolyl-β-D-galactopyranoside (X-gal) marker system. It could therefore be expected that *E. coli* strains expressing mutant Cre recombinases which allow recombination of loxK1 or loxK2 should lose the abfA.st gene and should form white colonies on Z-ara plates. All other clones, however, should be dark blue. Using abfA.st instead of the well established lacZ screen was necessary, because the *E. coli* strain (see below) used for this construct expresses β-galactosidase endogenously.

*E. coli* Strains for Selection and Screen

The *E. coli* strain BS583, DH5 Δlac (λD69 loxP$^2$[lacZ LEU2]), was chosen as the bacterial background for the selection procedure for K1+ or K2+ Cre mutants by plasmids pBS583 or pBS584. Due to the loxP²[lacZ] containing λprophage, Cre activity on loxP can be evaluated simply by using X-gal plates. The selection strains BS1493 and BS1494 were made by introducing the selection plasmids pBS583 and pBS584 into BS583 (Table 2). The loxP2 plasmid pRS613, to be used as a control, needed to be in BS583 cells as well, becoming the strain BS1541 (Table 2).

For the screening plasmids PBS601 and pBS602, *E. coli* strain NS2300 (Sternberg et al., *J. Mol. Biol.*, 187:197–212 (1986)) was selected as host: K12 recA::Tn10 ($\lambda i^{434}$loxP2 [neo]). This strategy combines a kanamycin selection for Cre enzymes, that are no longer active on loxP (P−), with a screen for K1+ or K2+enzymes. By transforming pBS601 and pBS602 into NS2300, the P−selection strains BS1523 and BS1524 were formed (Table 2).

Selection and Screen for CRE Mutants

Selection for K1+/K2+ and Screen for P−

After ligation of the generated mutant cre pool into pBAD33 for 3 h, BS1493 or BS1494 electrocompetent cells were transformed with 2 μl of the microdialyzed reaction mixture (VS membrane, Millipore™ Bedford, Mass.). To induce expression of the cre pool, the transformed cells were incubated at 37° C. in induction medium for 2.5 h and/or 4 h under agitation (as mentioned before). Cultures were diluted 1/500 or 1/5000 and grown on LB plates with the following formulation: Ap, Cm, glucose, and X-gal for determining the transformation efficiency, referred to as non-selection plates. Dilutions of 1/5 and occasionally 1/50 were grown on plates with addition of Kan, used to select for K1+or K2+ mutants and called selection-plates. The formulation of the plates served the following purposes: (i) Ap and Cm were added to assure that all clones contained both, selection and expression plasmid, (ii) X-gal to distinguish between P+ and P− clones (Table 2). After overnight incubation at 37° C., blue and white colonies were counted and pools prepared for the next round of DNA shuffling. Alternatively, certain mutants were chosen for further analysis (see below).

Selection for P− and Screen for K1+ or K2+

After 2.5 h and/or 4 h of expression of the mutant cre pool in the transformed BS 1523 and BS 1524 cells, usually dilutions of $10^{-3}$ or $10^{-4}$ were grown on LB agar plates supplemented with the same reagents as listed above, except, that Z-ara replaced X-gal to allow the K1+/K2+ screen. Non-selection plates were used for determining the transformation efficiency, and Kan containing plates for the P− selection (Table 2).

Mutant Analysis wt cre Expression Plasmid

With fewer cycles (15) of non-mutagenic PCR on the cre expression plasmid pBS185 and after linker digestion, the cre pool obtained was cloned into pBAD33 and transformed into BS583 cells. After 2 h of cre expression, the transformed cells were grown on X-gal plates. After overnight incubation at 37° C., two white colonies (indicating loxP recombination) were picked for plasmid preparation and complete sequencing. No point mutation was found in either one, so that each could be used as a control plasmid for wt Cre expression. One of the two was selected for further use and named pB5606.

Functional Testing

In order to determine the frequency of lox recombination of isolated mutant Cre enzymes by the described selection procedure, it is necessary to separate the cre candidate expression plasmid (pBAD33) from the selection plasmid of the chosen $Kan^R$ candidate. Then, the cleaned expression vector can be used to retransform the appropriate selection and screening strain BS1494, as well as BS 1493 and BS 1541 to determine the candidate's capacity for loxK2, loxK1 and loxP recombination under identical conditions. By comparing the resulting frequencies of $Kan^R$ of different Cre mutants and wt Cre, all treated identically, one can determine quantitatively how well each chosen mutant candidate really performs on the altered lox sites.

Therefore, overnight cultures of candidates were grown in liquid LB supplemented with Cm and Kan for plasmid minipreps yielding a mixture of both the mutant Cre expressing plasmid pBAD33 and the newly $Kan^R$ selection plasmid. In order to eliminate the latter, minipreps were digested with the restriction enzyme Aat II which only cuts the selection plasmid. After transformation of BS583 cells with this digestion mixture and approximately 2 h ere expression, different dilutions were grown on LB agar plates supplemented with Cm and X-gal to select for pBAD33. Plates with Ap plus Cm were used to determine the background of contamination with uncut selection plasmid. The next day, clones obtained by the Cm selection were tested for $Ap^s$ and $Kan^s$ to confirm the elimination of the selection plasmid. A final overnight culture, followed by a miniprep procedure, yielded the unique plasmid for functional testing, as described above.

Sequencing

To obtain the DNA sequence of candidate cre genes in pBAD33, eight primers (BSB454 to BSB461, Table 3), four for each strand, were designed so that the entire gene could be sequenced in both directions.

Site-Directed Mutagenesis

After identifying one essential mutation for the decrease in substrate specificity, the Stratagene QuickChange™ Site-Directed Mutagenesis Kit (Stratagene Cloning Systems, La Jolla, Calif.) was used to create cre mutants with mutations at the determined location, only. Using three different mutant primer sets (BSB 465 to BSB 470, Table 4), all steps were carried out as detailed in the manufacturer's instruction manual, except that electrocompetent BS1494 cells were used for transformation and mutant selection, replacing the provided XL1 blue cells. The made mutant candidates were subjected to functional testing and sequencing as detailed before.

In a different experiment, the DNA shuffling mutagenesis procedure was repeated on wt cre by adding one 5' phosphorylated strand of each set of mutant oligonucleotides (BSB465, BSB467 and BSB469) to the pool of small fragments prior to reassembly. This allowed to incorporate them into the resulting cre pool. The desired mutations should consequently be introduced at much higher frequency than without the addition of oligonucleotides.

RESULTS

Establishment of the Selection Procedure

Selection Plasmids (pBS583 and pBS584)

To test the generated plasmids pBS583 and pB584, a recombination event between their lox sites was mimicked by digesting pBS566 and pBS567 (intermediates of the pBS583/584 construction, containing only the 3' lox site) with Sal I and XhoII, followed by relegation. This lead to excision of the EGFP gene and terminators. After deletion of EGFP and $rrnBT_1T_2$, the $Kan^R$ phenotype was observed as anticipated. In addition, the frequency of spontaneously occurring Kan$^R$ clones carrying the original plasmids was approximately 10$^{-7}$. This background is inconsequential, since the transformation efficiency of BS583 cells was determined as 10$^7$ per μg of pBAD33.

The equivalent loxP control plasmid pBS613 was tested directly with the wt cre expression plasmid pBS606. After 2.5 h of cre expression, 94% of all clones were determined Kan$^R$ and about 6% showed blue color. Without cre expression, no Kan$^R$ and no white colonies were observed. This confirms that the control cell line BS1541 (Table 2) permits the combined P$^+$ selection and P$^-$ screen.

Screening Plasmids pBS601 and pBS602

Only pBS602 was tested before use by expression of wt Cre and a K2$^+$/P$^+$ Cre mutant (see below). On non-selection medium, wt Cre expression resulted in more than 95%, whereas expression of the mutant Cre resulted in less than 3% of blue colonies. This indicates that excision of the loxK2 flanked abfA.st marker by K2$^+$ Cre is possible. On selection medium, very few colonies could be found, since both types of cre have shown activity on loxP before (see below).

Mutagenic vs. Non-Mutagenic PCR

The frequency of P$^-$ Cre mutants obtained after non-mutagenic and after error-prone PCR was determined by the following experiment: After one mutagenic or one non-mutagenic PCR on the wt Cre expression plasmid pBS 185, the resulting cre pools were inserted into the expression vector pBAD33 and transformed into BS583 cells. After 2.5 h of arabinose-mediated induction or glucose-mediated repression (by SOC medium) or cre expression, dilutions were transferred to LB plates with Ap, Cm, glucose and X-gal. The results are presented in Table 5: Under glucose repression, exclusively blue colonies could be identified (first line in Table 5), indicating that cre expression is insufficient for loxP recombination and excision of lacZ of BS583. Induction with L-(+)-arabinose, however, lead to the formation of white colonies at the presented frequencies (second line), indicating that (i) the described control of cre expression by pBAD33 is functioning, and (ii) the mutagenic PCR conditions cause three times more impaired Cre enzymes for loxP recombination than the non-mutagenic conditions (60%) blue colonies vs. 30%). It is worth mentioning that ligation reactions lacking cre insertion resulted in 50 to 100 times less blue colonies than obtained with the ligations with cre insertion. This phenotypically blue background of empty pBAD33 was subtracted before calculating the presented data.

Leung et al., *Technique*, 1:11–15 (1989) reported that the frequency of point mutations created by error-prone PCR is about 0.5%. If this is true, in average five point mutations should occur in each 1 kb cre coding sequence subjected to an error-prone PCR. By extrapolating this data to the three times less P$^-$ enzymes after a non-mutagenic PCR, one can conclude that the frequency for point mutations should also be reduced by a factor of three to 0.18%. Experiments made by Zhou et. al. (1991) showed 11% of a 633 bp marker gene phenotypically impaired after non-mutagenic PCR. About 37% of all genes in the pool, however, carried at least one point mutation. Even though the conditions for the non-mutagenic PCR were similar, the observed discrepancy between 11% and 20% of phenotypical mutants may be due to a variety of reasons, among which: (i) the size difference between the two genes (633 bp vs. 1020 bp), (ii) different elongation times during PCR, and (iii) different sensibility of the two proteins for disabling point mutations.

Testing wt Cre on loxK1$^2$ vs. loxK2$^2$ Substrates

The level of loxK1 and loxK2 recombination due to wt cre expression was determined using the wt Cre control plasmid pBS606. After transformation of the cell lines BS 1493 and BS 1494 with pBS606 and 2.5 h and 4 h of cre expression, cells were grown on selection and non-selection plates (as described previously). The recombination frequency between the altered lox$^2$ sites was considered equal to the observed frequency of Kan$^R$ phenotype: for loxK1, it was about 10$^{-5}$ after 2.5 h and 2×10$^{-5}$ after 4 h of wt cre expression, for loxK2, it changed from about 2×10$^{-5}$ to 2×10$^{-3}$. All colonies found were white, indicating effective loxP recombination by wt Cre within the allowed expression time. This result shows that long term expression of the wt enzyme permits a slight increase in recombination between the altered lox sites. The use of pBAD33 to avoid background lox recombination by suppressing cre expression is therefore justified. Because loxK2 was eventually 100 fold better recognized by wt Cre than loxK1 (but still at low frequency), first the creation of novel Cre recombinases with loxK2 specificity was attempted.

Mutagenesis on loxK2

First Rounds of Directed Evolution

The result of the first four rounds of the described mutagenesis procedure on loxK2 with selection plasmid pBS584 are presented in Table 6. The following symbols are used to describe the status of the DNA shuffling procedure for cre: "o" indicates a non-mutagenic PCR, "m" a mutagenic PCR, and "x" stands for the in vitro reassortment event. For example, mxoxox cre represents a cre pool subjected to three rounds of the directed evolution process, with a mutagenic PCR followed by in vitro shuffling in the first, and non-mutagenic PCRs and shuffling as mutagenic and recombinogenic events in the following two rounds. The phenotypically blue background due to empty pBAD33 was subtracted from all results by control ligations without cre insertion. In every round, error-prone and non-mutagenic PCR served as the necessary mutagenic event on the template pool of the previous round. After in vitro reassortment and selection, always the larger Kan$^R$ population of the two parallel experiments was chosen as template for the next round (as indicated in the last column of Table 6). Only in the first round the error-prone PCP could lead to more candidates, whereas in all following rounds the reduced mutagenic frequency of the non-mutagenic PCR turned out to be more beneficial. The density of point mutations resulting out of two mutagenic PCB's was obviously too high to allow efficient elimination of deleterious mutations from advantageous ones during the in vitro shuffling step. This is confirmed by the high frequencies of blue colonies found within any pool in any round subjected to mutagenic PCB's twice. Error-prone PCR in the context of the applied selection therefore appears to be useful in the first round only, where its three times higher mutagenic frequency increases the amount of beneficial mutations compared to a non-mutagenic PCR. With increasing cycle numbers non-mutagenic PCR's should be preferred to avoid high densities of deleterious mutations.

The established directed molecular evolution process allows effective evolution of cre. Column Five of Table 6 shows that with every round the number of Kan$^R$ colonies is increasing, while the time for cre expression could be lowered from 4 h to 2.5 h (column three). After only three rounds, Cre mutants capable for loxK2 recombination at decreased concentrations due to the reduced expression time were found. However, it was not possible to isolate any blue colony on the selection plates. All identified K2$^+$ mutants therefore are also P$^+$. As mentioned above, high densities of deleterious mutations in the cre pool subjected to error-prone PCR's twice could explain why no blue colonies were seen on selection plates, even with over 90% of P' candidates on non-selection plates.

Evaluation of Six $K2^+/P^+$ cre Mutants

Functional Test

As indicated in Table 6, 36 white $Kan^R$ colonies could be isolated from the mxoxox cre pool after only 2.5 h of cre expression with an 115 dilution grown on selection plates. This result indicated that competent Cre mutant capable of loxK2 recombination were produced. Six were selected for further analysis. After elimination of the selection plasmid from the minipreps (as, described in Materials and Methods), all six of them, as well as wt Cre (pBS606) were subjected to the described functional test on loxK2, but also on loxK1 and loxP recombination with plasmids pBS584, pBS583 and pBS613. The results are presented in Table 7.

Briefly, by selecting for loxK2 recombination, all mutants except mxoxox 4, showed significantly increased percentages of $Kan^R$ (between 3% and nearly 70%), compared to wt Cre (0.002%), as indicated in column three of Table 7. This indicates a $10^3$ to over $10^4$ fold increase in activity on loxK2.

On loxP, all (including mxoxox 4) showed recombination frequencies between 80% and 100% after 2.5 h of cre expression (column 4). This was expected from the results obtained with the X-gal screen for loxP recombination during the selection procedure. 2.5 h of induction for wt cre expression is therefore sufficient for almost complete loxP recombination, justifying 2.5 h of expression of mutant cre pools for selecting competent $K2^+$ Cre mutants. The observed slight decrease in loxP recombination with the mutants mxoxox 3 to 6 either derived from usual variations during experiments, or may indicate a slightly reduced loxP activity. With BS1541 blue colonies on both selection and non-selection plates were found in approximately the same frequency (2% to 20%) as kanamycin sensitivity ($Kan^S3$). This indicates competition between the $loxP^2$ [lacZ] site on the genome and the $loxP^2[EGFP-rrnBT_1T_2]$ sites on pBS613. Since the same Cre mutants never resulted in blue colonies during selection for loxK2 recombination in cell line BS 1494, it is possible to conclude that loxP is still preferred over loxK2. This argument is supported by higher frequencies of loxP recombination, close to 100%, compared to the loxK2 recombination frequencies of 3% to 70%.

All frequencies found for loxK1 recombination, determined by using cell line BS1493, lie below 0.01% after 2.5 h, as well as after 4 h of induction of cre expression (column five). This indicates that no analyzed mutant developed an increased activity on lox K1 compared to wt Cre.

To summarize, five out of the six analyzed mutants showed a significant decrease in specificity, resulting in the possibility for loxP and loxK2 recombination.

Sequencing

The six described mutants have been completely sequenced in both directions to determine the mutations which lead to the observed decrease in specificity. The resulting aligned cre coding and as sequences of all mutants and wt Cre are represented in Tables 10 and 11. Each mutant showed between 3 and 8 point mutations, altogether 31, as listed in column two of Table 8. The overall mutagenic frequency can therefore be calculated at 0.5% (31 mutations in 6 clones of 1020 bp), which is similar to only one round of error-prone PCR (Leung et al., Technique, 1:11–15 (1989)). The reason for the low frequency of point mutations after three rounds of the mutagenesis procedure (i.e. nine PCR's) is the applied selection after each round, cre mutants with low density of point mutations seem to be favored by the stringent kanamycin selection.

26 of the 31 identified point mutations resulted in as changes compared to the wt sequence, as indicated in column three. No deletions or frame-shift mutations, as well as no codons affected by more than one point mutation at the same time could be identified. All possible transition events could be observed, but only half of all possible transversion events (shown in Table 12). Adenine to guanine and vice versa transition events represented almost 30% of all identified point mutations. All other events occurred less frequent (10%, 7%, or never). The represented statistic may however be biased, either since only six mutants were analyzed, or due to the directed molecular evolution technique itself: The types of point mutations observed less often, may more frequently be deleterious in cre and were consequently removed from the pools. With more mutants to be sequenced, this question could be addressed further.

Only one point mutation, a transition event from adenine to guanine at position 785 in the cre coding sequence is common for all 5 mutants with remarkably increased loxK2 activity. This mutation leads to a replacement of a glutamate residue at position 262 in the J helix of wt Cre by a glycine (indicated in column five of Table 8). This glutamate is believed to contact the loxP sequence at positions 11 or 12 with its acidic side chain (Quo et al., Nature, 389;40–46 (1997)). Another point mutation, resulting in a conservative threonine to serine exchange at position 316 was identified in three mutants. Five point mutations were found independently in two of the six mutants, among which two types of silent mutations. Finally, eleven point mutations occurred only once (indicated in column four). Therefore, the critical mutation for loxK2 activity appears to be E262G. Some of the additional mutations could be responsible for the observed ten fold difference in loxK2 recombination frequency among the five E262G carrying mutants.

Site-Directed Mutagenesis to Verify Results

Site-Directed Mutagenesis Procedures

To determine whether the E262G mutation alone is responsible for the increase of loxK2 activity of the Cre mutants by at least a factor of $10^3$, two different experiments were made:

First, the described directed evolution procedure was repeated in three different sets on wt cre, by adding three 5' phosphorylated mutant oligonucleotides prior to reassembly: Incorporation of the first oligonucleotide (BSB465) into cre should lead to the E262G mutation, incorporation of the second one (BSB467) to a E262A mutation, and the equimolar mixture of random oligonucleotides (represented by BSB469) to $20^3$ (=8000) possible as combinations at positions 261 to 263 of Cre. According to Stemmer, W. P. C., Proc. Natl. Acad. Sci. USA, 91 10747–10751 (1994), these oligonucleotides should be incorporated during reassembly and cause the desired mutations at a frequency of about 8%. After insertion of the resulting cre pools into pBAD33 and 2.5 h of expression, 0.8% of white $Kan^R$ colonies were found with BSB465. Therefore, the frequency of the $Kan^R$ phenotype due to loxK2 recombination is ten times lower than the expected frequency for the E262G mutation to occur. This indicates that the E262G mutation increases the specificity for loxK2 from 0.002% of wt Cre (see above) to approximately 10% of recombination during the standard expression experiment (2.5 h of cre expression prior to selection). By using the second oligonucleotide (BSB467) only 0.09% of the total white colonies showed $Kan^R$. Thus, E262A still favors lox K2 recombination but by almost a factor ten less efficiently than the E262G mutation. With the random oligonucleotide mixture (BSB469), the frequency of loxK2 recombination shrunk to 0.02%. Compared to a control experiment with no oligonucleotides added, resulting in 0.003% $Kan^R$ (consistent with the results obtained below), still some of the possible 8000 as combinations at positions 261 to 263 of Cre are expected to favor loxK2 recombination. Since the frequency of blue colonies on non-selection plates was about 30%, a clear indication for additional mutations, it cannot be completely excluded that some of the occurred $Kan^R$ mutants of this experiment have been carrying some additional beneficial mutations. Nevertheless, this experiment indicated that the E262G mutation is probably the basis for significant increase in loxK2 activity.

For better defined mutations, a second experiment was done: The same oligonucleotides, now in sets for both DNA strands, were used with the Stratagene QuckChange™ Site-Directed Mutagenesis Kit as described in Materials and Methods. After transformation of the loxK2 selection strain BS1494, the percentage of white $Kan^R$ colonies in the three different experiments could be determined as 6.2% for E262G, 0.8% for E262A and 0.6% for the 8000 different ten (10) days combinations as positions 261 to 263. Due to the QuickChange™ procedure, which eliminates parental DNA, one could expect that the desired mutations occurred in at least 50% of all clones of the three different pools. This assumption indicates that the E262G mutation alone results in approximately 12% or less recombination frequency on loxK2 (6% out of 50% or more carrying the mutation) and the E262A exchange in 1.6% or less (under standard conditions). This calculation is not valid for the third set of oligonucleotides, because no defined mutation is introduced but rather a mixture of 8000 different ones. Blue colonies were not found during this experiment, confirming that the frequency of additional mutations altering Cre activity on loxP was very low.

The results of both experiments indicate consistently, that the E262G mutation alone is sufficient to increase loxK2 recognition by approximately a factor of $10^3$ compared to wt Cre. The ten times higher frequency observed with three of the six analyzed mutants after three rounds of the mutagenesis procedure can only be explained with additional beneficial mutations. The E262A mutation increases the frequency of loxK2 recombination also, but approximately by a factor of ten less effectively than E262G.

Sequencing and Elimination of Possible Additional Mutations

Two white $Kan^R$ colonies of each pool derived from the site-directed mutagenesis procedure were selected and the entire cre gene was sequenced. Both E262G and E262A candidates showed the desired sequence with no additional mutations. The random candidates surprised: One of them did not reveal any point mutation, representing an artifact which managed to survive the selection, whereas the other one showed nucleotide alterations from position 783 to 786. The wt sequence ($781$CTG GAA$_{786}$) was found to be changed to ($_{783}$ CTT TGG$_{786}$), resulting in one silent mutation, conserving L261, and a E262W exchange. To exclude possible mutations in pBAD33 due to the PCR involved site-directed mutagenesis procedure, the three defined cre mutants (E262G, E262A, and E262W) were excised by Hind ill and Xbo I and reinserted into the MCA of fresh pBAD33.

Functional Testing

The three defined Cre mutants for the amino acid position 262 were subjected to a functional test for loxK2, loxK1 and loxP recombination activity, as mentioned before. The results are summarized in Table 9. First, the results described previously for the E262G and E262A mutations were confirmed: As indicated in column three, the loxK2 recombination frequency increased 103 fold with the E262G mutant compared to the wt enzyme, whereas the E262A mutant shows only an increase of 200 fold. Surprisingly, the E262W mutant also achieved a similar activity on loxK2 as seen with the E262G mutant. The test for loxP recombination frequency with cell line BS1541 (column four) showed that the ability for loxP recognition is at best slightly impaired by the three different mutations (as already seen with the analyzed mxoxox mutants). Again, blue colonies could only be found with this cell line, indicating that loxP is preferred over loxK2 (as described before). As expected, none of the three mutants performed significantly better on loxK1 than wt Cre (column five). To conclude, this final experiment provides the necessary evidence that the E262G mutation presents the basis for the observed decrease in specificity of Cre. However, additional mutations seem to be helpful to increase the newly obtained activity further. In addition, glycine at position 262 is not the only possible residue to permit a remarkable increase in loxK2 activity.

DISCUSSION $K2^+/P^+$ Cre Mutants

The chosen random mutagenesis procedure linked to the described selection in *E. coli* allowed the identification of Cre mutants, characterized by a wider substrate recognition. The evolved enzymes showed wt-like activity on loxP sites and in addition had almost the same activity on altered $lox^2$ sites, referred to as loxK2. By contrast, the wt enzyme showed only marginal activity on $loxK2^2$ substrates.

lox Sites loxP and loxK2 differ at several locations as illustrated in FIG. 1: First, the three outermost by of the inverted repeats are altered, facilitating the construction of the various plasmids used for selection. Second, the entire non-canonical 8 bp spacer is completely exchanged, and third, two transversion events (thymine to adenine) are introduced at positions 11 and 12 of the lox site. Only the two transversion events are considered important for inhibiting wt Cre from recognizing the site. Other investigations have shown before, that the two alterations of loxP mentioned first are without inhibiting effect on wt Cre (B. Sauer, unpublished results). The design of loxK2 was based in part on so-called cryptic lox sites, that were identified previously in the yeast genome (Sauer, B., *J. Mol. Biol.*, 233:911–928 (1992)). Another consideration was the choice of a good starting sequence for the described mutagenesis procedure. Starting with sites that contained several and/or widespread alterations of loxP was avoided, because the greater the number of alterations in the substrate, the more the enzyme would have to be altered. Consequently, to most effectively use the mutagenesis procedure, the two sites presented in FIG. I, loxK1 and loxK2, were designed to have only two critical alterations. In initial experiments, wt Cre was found to recombine $loxK2^2$ substrate pBS584 slightly better than $loxK1^2$ pBS583. This difference may depend on the fact that in loxK2 the two alternations are located next to each other, while in loxK1 they are separated by 3 bp (positions 14 and 10). Thus, loxK1 could interfere with wt Cre binding at two distinct DNA-protein interaction sites as compared to loxK2, where only one location of incompatibility is available. For this reason, loxK2 was chosen for the initial set of experiments, described in this work.

Cre Mutants after Three Rounds of Directed Evolution

Three iterations of the in vitro evolution procedure were necessary to identify 36 candidates, expressing Cre mutants that could process loxK2 (based on the applied selection procedure in *E. coli*). Tests showed that five out of six selected ones had $10^3$ and $10^4$ fold increased activity on loxK2 when compared to wt Cre. On loxP and loxK1, however, there was almost no difference between wt and the mutant enzymes. The mutants therefore had developed an increased tolerance from transversions at positions 11 and 12 (loxK2) of the lox sequence, but not for other positions like 10 and 14 (loxK1). To indicate this phenotype they were referred to as $K2^+/P^+$.

The E262G Mutation

Sequence analysis identified that the five mutants with remarkably enhanced loxK2 activity ($10^3$ to $10^4$ fold compared to wt Cre) had in common only one point mutation, leading to the as change E262G. Site-directed mutagenesis experiments confirmed, that the E262G mutation is sufficient to increase loxK2 activity by a factor of $10^3$ compared to wt Cre.

Based on the recently described crystal structure (Guo et al., *Nature*, 389:40–46 (1997)) glutamate at position 262, located in the J helix of the enzyme, may be a DNA contacting residue and permit the formation of a hydrogen bond between the carboxyl group of its side chain and an amino group of one of the two adenines at positions 11' or 12' in the loxP sequence (FIG. 1). However, changing these two bases to thymines in the loxK2 sequence should lead to an electrostatic repulsion between their oxygens and the acidic side chain of glutamate. This could explain the observation that wt Cre is unable to catalyze a recombination between two loxK2 sites. Exchanging glutamate for a glycine, that does not have a side chain, should remove the electrostatic repulsion and thereby permit loxK2 binding. On the other hand, this alteration could affect loxP binding because an electropositive DNA-protein interaction may be lost. Results from the mentioned experiments support this proposition: The E262G mutation along lead to an increase in loxK2 recombination from 0.002% to about 2% and to a slight decrease in loxP recombination from 94% to about 80%. The 50 times lower frequency of loxK2 compared to loxP recombination may depend on the second thymine or more likely on the complementary adenine (position 11 in loxK2) that could contribute to sterical repulsion between the J helix and the loxK2 site. To prove this hypothesis, the role of arginine at position 258, located one helix turn away from the glutamate, should be further investigated by site-directed mutagenesis. As proposed by Guo et al., *Nature*, 389:40–46 (1997), R258 is a DNA contacting residue that forms hydrogen bonds with the guanine at position 10' of loxP and may also interact with the bp at position 11. There is yet no confirmatory experimental evidence for this proposal.

Results from three initially isolated mutants (mxoxox 1 to 3) indicated about 50% of recombination frequency on loxK2. This is about ten fold higher than that obtained with the E262G mutation alone. It is therefore likely that some of the additional point mutations identified in these three mutants account for this increase in activity. Table 8 lists all point mutations that were found. If silent and conservative mutations are considered not to influence specificity, only a limited number of candidates to account for the phenotype remains. Among these, S254G and Q255R of mxoxox 2 and 3, because of their location close to the amino-terminus of the J helix, could be expected to influence DNA contacts with positions 11 or 12 of the lox site. The other mutations are scattered in the N- and C-terminal domain of Cre. All, except R101Q of mxoxox 5, affect aa that are not located within the proximity of DNA contacting areas. Some appear independently in two mutants, e.g. D29A or D189N, that could influence protein folding or the interactions among the four Cre enzymes necessary for recombination. Such alterations could influence for example the orientation of the J helix and thereby reduce remaining interference between the loxK2 site and the enzyme. Alternatively, some mutations, also silent ones, could influence protein expression, leading to a faster accumulation of enzymes and consequently to higher recombination frequency. This possibility should however also influence loxP recombination. In fact, after 2.5 h of cre expression, the mutants mxoxox 1 and 2 showed a slightly higher frequency of loxP recombination compared to wt cre (98% vs. 94%). This difference, on the other hand, may be attributed to the variations that occur normally within experiments. To address this question further, shorter cre expression times on loxP would be required.

When the coordinates of the crystal structure (Guo et al., *Nature*, 389:40–46 (1997)) are available (protein data bank, Brookhaven National Laboratory), it will be possible to confirm many of the tenets discussed.

Finally, the increase in loxK2 tolerance between the E262G mutation alone and the isolated mutants carrying additional point mutations justifies the use of the DNA shuffling procedure linked to selection: Not only has it permitted the elimination of deleterious mutations from the sequence pool, but it helped to accumulate various more or less beneficial aa alterations as well.

The E262A and E262W Mutations

The mentioned site-directed mutagenesis procedure was used to generate two more defined Cre mutants, E262A and E262W. Compared to the E262G mutati8on, E262A permitted loxK2 recombination ten fold less effectively. The E262W mutation however resulted in similar activity on loxK2.

The aliphatic side chain (a methyl group) of A262 could be the reason for slight sterical interference. This would explain the observed reduced frequency of loxK2 activity with E262A. loxP recognition, however, could not be found to be affected compared to E262G. The lowered loxK2 activity explains why no E262A mutation was identified in the small pool of six analyzed mutants: With a ten fold decrease in activity, one would expect to encounter the corresponding mutation ten times less often during selections as well.

In contrast to the small side chain of alanine, the large aromatic side chain of W262, was expected to inhibit recombination between any lox sites due to sterical interference. Surprisingly, this seems not to be true. A possible explanation for the observed activity on loxP and loxK2 could be that the aromatic and planar structure of the tryptophan side chain, fits better into the J helix—lox interface than does a methyl group. Different influences of A262 and W262 on folding of the J helix could also contribute to the observed phenotypes. The reason why the E262W mutation was not identified among the six analyzed mutants is the genetic code. Whereas for the E262G and E262A mutations only one bp in the glutamate encoding G<u>AA</u> codon needs to be mutated to G<u>GA</u> or GC<u>A</u>, for E262W the whole codon must be exchanged to TGG. This is unlikely to occur during the applied random mutagenesis procedure with a mutation frequency of 0.5%. Other amino acid changes due to two or three mutations of the glutamate encoding codon therefore cannot be considered to have occurred during the random mutagenesis procedure.

When the coordinates of the crystal structure are public, it will be interesting to confirm and further investigate the discussed hypothesis.

| ABBREVIATIONS | |
|---|---|
| 5-BI-ara a.k.a Z-ara | 5-bromo-3-indoyl-α-L-arabinofuranoside |
| aa | amino acid |
| AP(AP$^R$, Ap$^S$) | ampicillin |
| bp | base pairs |
| Cm(Cm$^R$, Cm$^S$) | chloramphenicol (resistant, sensitive) |
| cre - Cre | cyclization recombination (gene - Protein) |
| Da | Dalton |
| DMSO | dimethylsulfoxide |
| ds | double stranded |
| GF | gel filtration |
| K1$^+$ or K2$^+$ | Cre mutant capable for loxK1 or loxK2 recombination |
| Kan (Kan$^R$, Kan$^S$) | kanamycin (resistant, sensitive) |
| lox | locus of crossover |
| MCS | multiple cloning site |
| mRNA | messenger RNA |
| neo - Neo | neophosphotransferase (gene - Protein) |
| P$^-$ or P$^+$ | Cre mutant defective or capable for loxP recombination |
| PCR | Polymerase Chain Reaction |
| SD | Shine-Dalgarno sequence |
| ss | single stranded |
| TK | thymidine kinase |
| wt | wildtype |
| X-gal | 5-bromo-4-chloro-3-indolyl-β-D-galactopyranoside |

Example 3

Analysis of Variant Cre Recombinases

This example describes analysis the activity of several specific variant Cre recombinases.

Vectors pBS606, 614, 626, 627, 628 and 650: pBAD33 with wt, E262G E262G/D29A, E262G/D189N, E262G/T316S, and R3M3 cre insertion used for expression of the corresponding Cre proteins in DH5α for in vivo testing.

pBS632 to pBS641: pUC19 based plasmids for in vivo tests of different Cre mutants on a variety of different lox sites and combination of lox sites, all bearing the FAS1 spacer (Sauer B., *Nucleic Acids Res.*, 24:4608–4613 (1996)). Recombination between two lox sites leads to excision of a neo cassette to give kanamycin sensitive *E. coli*. The same plasmids were also used for in vitro recombination experiments.

pRH200: wt Cre expression plasmid (a generous gift from Ron Hoess, DuPont, Wilmington, Del.) used to overexpress wt Cre in BL21(DE3) (Novagen, Madison, Wis.) strain.

pBS654 to pBS658: wt cre of pRH200 was replaced with different cre mutants (E262G, E262G/D29A, E262G/D189N, E262G/T316S, and R3M3) using Age 1 and Mlµ 1 restriction sites.

*E. coli* Strains

ES583: The *E. coli* strain BS583, DH5 Δlac (λD69 loxP$^2$[lacZ LEU2]), was chosen as the bacterial background for the selection procedure using plasmid pBS584. Due to the loxP$^2$[lacZ] containing λ prophage, Cre activity on loxP can be evaluated simply by using X-gal plates.

BS1494: The *E. coli* strain for selection was established by introducing the selection plasmid pBS584 into BS583. Thus, BS1494 allows a kanamycin-selection for loxK2 and in parallel a blue/white-screen for loxP recombination with 5-bromo-4chloro-3-indolyl-β-D-galactopyranoside (X-gal). Note that the spacer region of the loxK2 site (FAS1) is different from the original one of loxP. Thus, recombination events between loxP of the λ prophage and loxK2 of the selection plasmid pBS584 catalyzed by potent Cre mutants are excluded in BS1494.

BS1576 to BS1581: For the in vivo recombination experiments wt and mutant Cre expressing strains were generated by introducing plasmids pBS606, 614, 626, 627, 628, and 650 into DH5α.

Transformation of *E. coli*

For plasmid transformations of *E. coli* strains, electroporation was preferred over chemical protocols. Electrocompetent cells were made and used for electroporation as described by Smith et al., *Focus*, 12:38–40 (1990). The appropriate cell porator and cuvettes were from Life Technologies (Bethesda, Md.).

Site-Directed Mutagenesis

The QuickChange™ Site-Directed Mutagenesis Kit (Stratagene Cloning Systems, La Jolla, Calif.) (1997) was used to generate defined single and double mutations in the cre gene.

Overexpression and Purification of Candidate Mutants

Wild-type and five different mutant Cre proteins were overexpressed using plasmids pRH200, and pBS654 to pBS658 in conjunction with Novagen B121 (DE3) cells. After induction for 2.5 cells were harvested, sonicated, and Cre partially purified after DNase I digest with a single step Whatman® P11 resin (Whatman Inc., Fairfield, N.J.) as described before by Wierzbicki et al., *J. Mol. Biol.*, 195:785–794 (1987). The obtained Cre preps were about 80% pure and protein concentrations ranged between 100 and 200 ng/µl.

Mutant Analysis

In Vivo: Plasmids pBS632 to pBS641 were transformed into Cre-expressing *E. coli* strains BS1576 (wt), BS1577 (E262G), BS1578 (E262G/D29A), BS1579 (E262G/D189N), BS1580 (E262G//T316S), and BS1581 (R3M3). After 1 hour of induction of cre expression with 0.2% L-(+)-arabinose, $10^{-5}$ dilutions were plated on non-selection medium containing 0.2% D-glucose. After overnight incubation at 37° C., colonies were transformed to kanamycin-selection plates for the described negative selection for neo excision.

In Vitro: Purified Cre mutants were used for both in vitro recombination and gel retardation experiments as described before by Sauer B., *Nucleic Acids Res.*, 24:4608–4613 (1996) and Wierzbicki et al., *J. Mol. Biol.*, 195:785–794 (1987), respectively. For the recombination reactions plasmids pBS632 to pBS641 served as substrates, whereas for the DNA binding reactions γ[$^{33}$P]-dATP (Amersham Pharmacia Biotech, Piscataway, N.J.) end-labeled 35 bp oligonucleotides were used, each encoding a lox-halfsite and one half of the FAS1 spacer.

Evaluation of Six K2$^+$/P$^+$ cre Mutants

Figure 13:
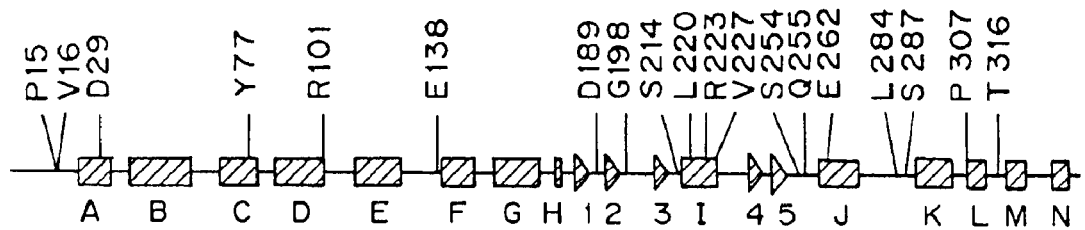
FIG. 13 is a diagram showing the identified amino-acid changes in the six selected Cre mutants are listed according to their position in the protein's secondary structure (silent mutations in parenthesis). Only one amino acid change, E262G, is common to all mutants with remarkably increased loxK2 activity (R3M1, 2, 3, 5, and 6), suggesting that this mutation is essential for the observed phenotype.

Six of the 36 identified single Kan$^R$ colonies of the third round were chosen for further analysis and referred to as R3M1 to 6 (Round 3 Mutants 1 to 6). Retesting them in the indicator strain revealed that all but one (R3M4) show significant loxK2 recombination and all are unbiased in their activity on loxP (Table 14). Sequencing analysis revealed one amino acid change common to all five mutants having increased loxK2 activity: a glutamate to glycine exchange at position 262 (E262G) in the J helix of the Cre protein (FIG. 13). A second point mutation, a conservative threonine to serine exchange at position 316 (T316S), was identified in three of the mutants with enhanced loxK2 activity. Two non-conservative mutations (D29A and D189N) were found in two of the five mutants. In addition, ten mutations occurred only once. Therefore, the critical mutation for loxK2 activity appears to be E262G.

Site-Directed Mutagenesis

To address the question of the influence of the different point mutations further, the QuickChange™ Site-Directed Mutagenesis Kit (Stratagene) was applied to generate the following Cre mutants, each confirmed by sequencing: E262G, E262G/D29A, E262G/D189N, and E262G/T316S.

In Vivo Characterization

To elucidate the contribution of specific amino acid changes in conferring altered recombinational specificity to Cre, recombination assays with different lox sites were carried out with the following Cre enzymes: the wt enzyme, one of the originally sequenced third round mutants (R3M3), and the generated single and double mutants. All lox sites used for the in vivo tests were designed to have the same 8 bp spacer region (FAS1) so that recombinational specificity was completely dependent on Cre's recognition of the symmetrical inverted repeats of the lox sites. Note that wt Cre-dependent recombination between loxP sites bearing the FAS1 spacer does not differ from recombination between original loxP sites (Sauer B., *Nucleic Acids Res.*, 24:4608–4613 (1996)).

Figure 14A:
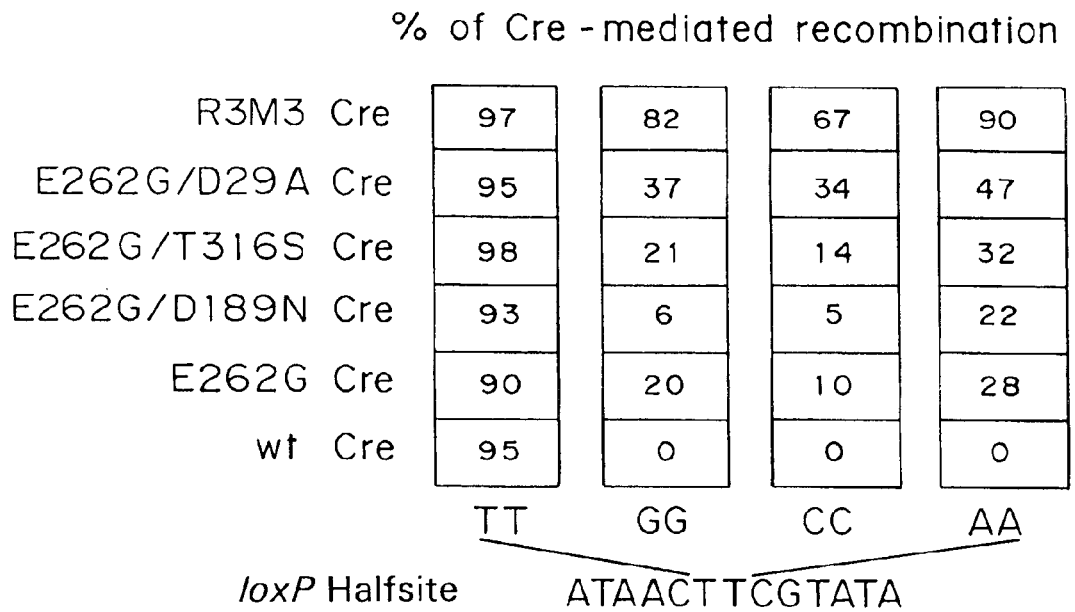
FIG. 14A is a table comparing recombination frequencies in vivo obtained with a variety of lox sites altered at positions 11 and 12 (SEQ ID NO: 41).

FIG. 14A presents the recombination frequencies of various mutant lox$^2$ substrates and combination of sites (loxP with loxK2 and as control with loxK1) from the marker excision assay. Mutant lox sites with symmetric nucleotide substitutions at positions 11 and 12 of the loxP sequence were tested with the wt enzyme and the five variant Cre mutants, including the multiple mutant R3M3(A). All enzymes showed a maximum in recombination (close to 100%) with thymines at these positions, i.e. with loxP$^2$. Adenines, i.e. loxK2$^2$, lowered the recombination frequencies drastically for the wt enzyme, whereas the single and double mutants performed approximately 50% and 70% less effectively. R3M3, however, showed nearly LoxP-like activity on the loxK2$^2$ substrate, as seen before with the selection strain (Table 14). Altering the two thymines to guanines resulted in similar recombination frequencies as seen with adenines at these positions. Cytosines, on the other hand, did not result in similar recombination frequencies as seen with thymines, but were surprisingly the least efficiently recognized substitutions of positions 11 and 12. To conclude, it appears that the E262G mutation is necessary and sufficient to significantly increase recombination frequencies on lox sequences which are symmetrically altered at positions 11 and 12. Of the additional mutations tested, D29A seems to be slightly beneficial, whereas D189N and T316S appear indifferent or even slightly deleterious for recombination on the variant sites. Thus, additional mutations of R3M3 (FIG. 13) must be responsible for its further increased performance on the mutant substrates in vivo.

Figure 14B:
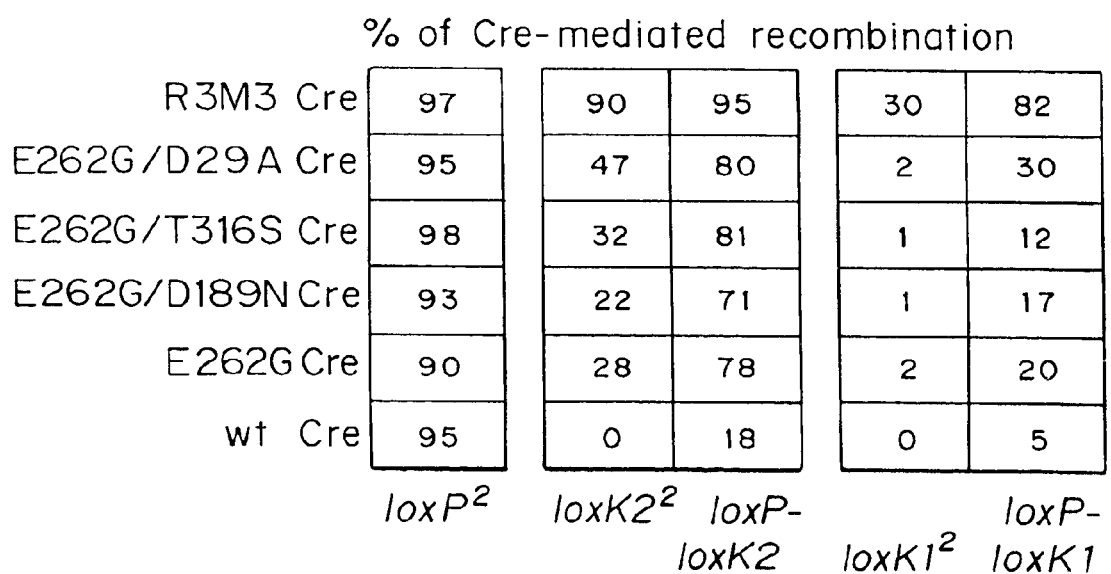
FIG. 14B is a table comparing recombination frequencies in vivo obtained with identical and mixed lox sites. Wild type Cre and five different mutant enzymes were tested for their performance on different/lox$^2$ substrates, as indicated. Given are the obtained percentages of recombination in vivo based on the described negative selection.
Figure 16:
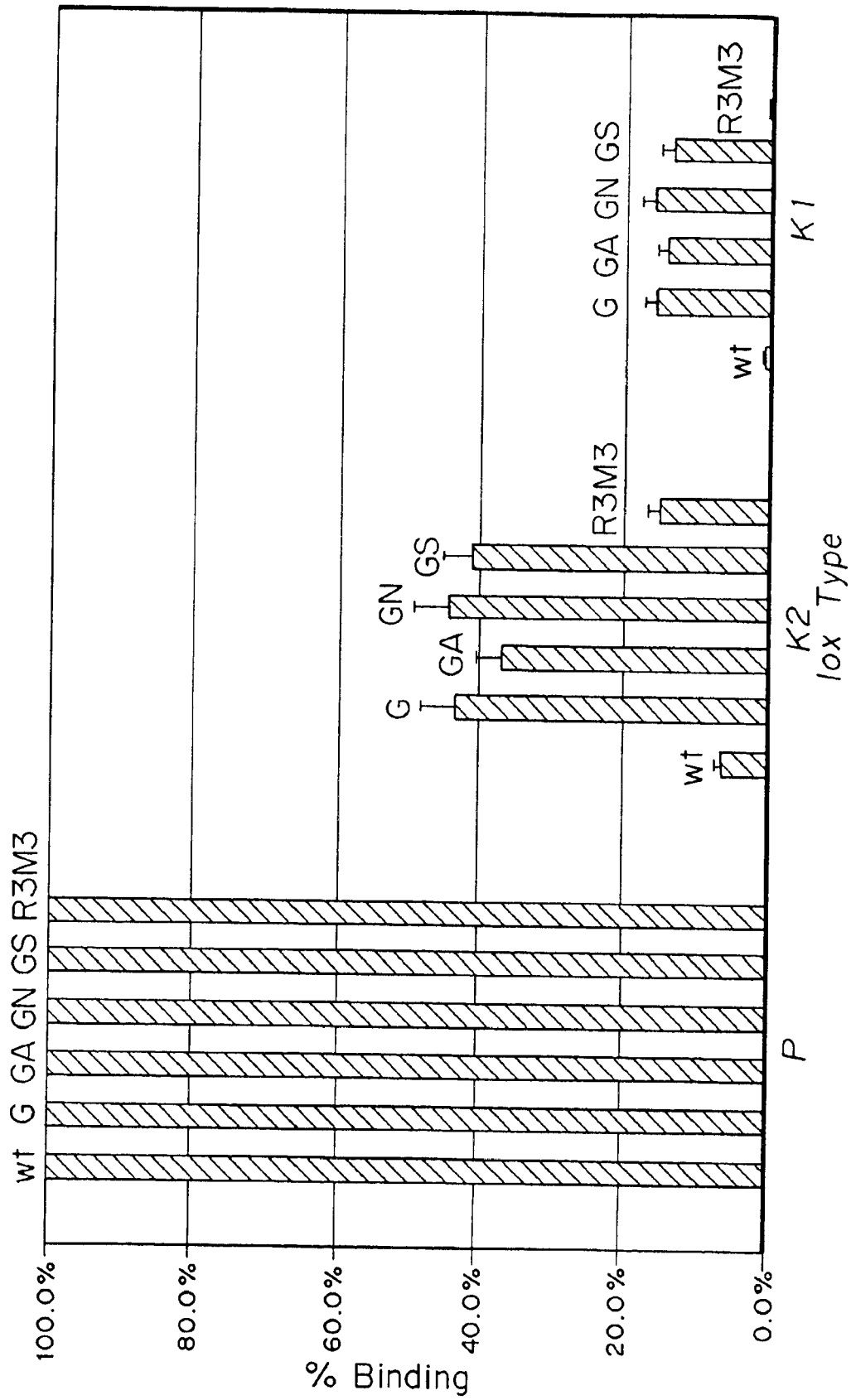
FIG. 16 is a graph of percent of various Cre recombinases (wt, G, GA, GN, GS, R3M3) bound to various lox sites (loxP, loxK2, loxK1).

FIG. 14B shows the observed recombination frequencies on mixed substrates (e.g. loxP with loxK2). For both loxK2 and the control substrate, loxK1, recombination with loxP by wt enzyme was substantially less than for loxP$^2$ recombination. This recombination frequency was increased dramatically with all of the mutant Cre protein. These results hint that not only a cooperatively in binding of two Cre molecules to one lox site exists but moreover also cooperatively between Cre molecules binding to different sites which then are synapsed and recombined. This finding is especially useful for genomic targeting: It suggests that a targeting vector carrying a loxP site will be effectively recombined with the endogenous lox-like site by the Cre mutants as long as the spacers are compatible.

Noteworthy also is R3M3-Cre's increased ability to recombine loxK1 by itself, whereas all the mutants, like wt, did not. Again, some additional mutations found in R3M3 (FIG. 13) seem to be responsible not only for increased recombination frequencies on loxK2 but also on loxK1 compared to Cre bearing the E262G mutation alone or in conjunction with the D29A mutation.

In Vitro Characterization

In Vitro Recombination Assays. For the in vitro recombination experiments the same substrates as in vivo—that is, pBS632 to pBS641—were used. An in vitro recombination experiment using wt, E262G, and R3M3 Cre preps on loxP$^2$, loxK2$^2$, and loxK1$^2$ substrate showed that, as seen in vivo before, wt Cre is capable to recombine loxP$^2$ substrates only. No recombination products are visible when loxK2$^2$ or loxK1$^2$ substrates were used. By introducing the E262G mutation into Cre, however, recombination of loxK2$^2$ substrates becomes possible at elevated frequencies, and even for loxK1$^2$ substrate recombination products become weakly visible in vitro. E262G-Cre activity on the loxK1 control site in vitro but not in vivo probably derives from differences in ionic strength and/or enzyme concentration between the assays. Finally, with R3M3 Cre the ability for both loxK2$^2$ and loxK1$^2$ recombination is further increased, as expected from the in vivo assays. As mentioned in the in vivo results before, guanines at positions 11 and 12 of the lox sequence were recognized at similar frequencies as seen with adenines (i.e. loxK2), whereas cytosines were clearly less tolerated by all Cre mutants. Slight differences between in vivo and in vitro recombination frequencies are probably due to differences in ionic strength, temperature, DNA condensation, enzyme concentration, etc. In general, the pattern of the in vitro recombination frequencies of the different Cre enzymes on the different lox sites mirrors the one seen in vivo.

Gelshift Experiments. Gelshift experiments were applied to address the question of in vitro DNA-affinities of the different Cre mutants. As expected from the previous results, all three Cre enzymes bind with similar efficiency to loxP, whereas to loxK2, only E262G and R3M3 show binding affinity. Surprisingly, R3M3 binding appears less efficient on the loxK2 half-site than binding of E262G, and on the loxK1 half-site only E262G does bind weakly whereas R3M3 does not.

DISCUSSION lox sites loxP and loxK2 differ at several locations as illustrated in FIG. 1: First, the three outermost bp of the inverted repeats are altered (positions 15, 16, 17, 15', 16' and 17'). Second, the entire non-canonical 8 bp spacer is completely exchanged (positions 4 to 4'), and third, two transversion events (thymine to adenine) are introduced at positions 11 and 12 (and mirrored at 11' and 12')of the lox site, mimicking potential recombination targets in eukaryotes. Only the two mutations at positions 11 and 12 are considered important for inhibiting wt Cre from recognizing the site. Thus, they were the only alterations in the loxi sites used for the in vivo and in vitro characterization experiments. Other investigations have shown that the two alterations of loxP mentioned first are without inhibiting effect on wt Cre (Sauer, B., *Mol. Cell. Biol.,* 7:2087–2096 (1987) and Sauer B., *Nucleic Acids Res.,* 24:4608–4613 (1996)). Noteworthy is however that the altered 8 bp spacer region (FAS1 spacer) does not allow loxP-loxK2 recombination, since the regions where the single-strand cleavages and exchanges take place are not compatible. To allow simultaneous monitoring of Cre-mediated recombination both at the wt loxP$^2$ and at a mutant lox$^2$ substrate (loxK2$^{2)}$, incompatible spacer elements were used to prevent recombination between the two types of lox sites by a candidate Cre mutant with altered specificity. Such recombination might easily compromise ready detection of desired Cre specificity mutants. Incompatible spacers (original loxP and FAS1) formed the basis for the simultaneous selection for loxK2 recombination and screen for loxP recombination with *E. coli* strain BS1494 which led to the disclosed variant Cre recombinases.

LoxK1, the other lox sequence used in this study, bears two critical bp exchanges per arm as well, however at different positions: 10 and 14. It was used as a control lox site, addressing the question whether the generated Cre mutants with novel specificity for loxK2 can also tolerate adjacent alterations within the lox sequence.

Cre Mutants after Three Rounds of Directed Evolution

Three iterations of the in vitro evolution procedure were used to identify 36 candidates which express Cre mutants that could process loxK2 (based on the selection), as well as loxP (based on the simultaneous screen). wt Cre, on the other hand, only shows marginal activity on loxK2 when expressed at very high levels.

Characterization

Sequence analysis revealed that five mutants with significant loxK2 activity had in common only one point mutation, leading to the amino acid change E262G. However, several other point mutations occurred independently twice or thrice, among which D29A, D189N, and T316S. To investigate the influence of the mentioned mutations on the observed phenotype, specific single and double mutants were generated by site-directed mutagenesis. In vivo and in vitro assays were then carried out with wt-Cre and five different mutants (R3M3, E262G, E262G/D29A, E262G/ D189N, E262G/T316S) to compare their performance on a variety of different alterations of the loxK2 site.

The in vivo and in vitro recombination assays showed a similar pattern in recombination frequencies for the different enzymes on the different sites tested. In general, recombination frequencies on mutant substrates were distinctively the highest with R3M3. The double mutant E262G/D29A was about half as effective as R3M3, whereas the other double mutants and the single mutant E262G showed slightly further decreased recombination frequencies on the altered sites. The wt enzyme did not recombine any of the mutant substrates presented here, neither in vivo nor in vitro. With previous results showing that single D29A, D189N, and T316S mutants of Cre perform like the wt enzyme on loxK2 and loxK1 in vivo and the fact that the E262G point-mutation was the only one found independently in all the originally isolated Cre mutants with loxK2 specificity, it is clear that E262G is a critical mutation that allows Cre to recognize loxK2. However, in combination with E262G, D29A permits still higher recombination frequencies on lox sites altered at positions 11 and 12. Since R3M3 shows even further increased recombination frequencies on the altered sites compared to E262G/D29A, other of the point mutations identified in this Cre mutant (see FIGS. 14A and 14B) must account for this increase in activity. Because of its location close to the amino-terminus of the J helix, the Q255R mutation of R3M3 could be expected to influence DNA contacts. Other mutations may influence protein folding or protein-protein interactions which could result in a higher flexibility within the Cre-lox interface and thus allowing a better tolerance of alterations of the lox sequence. This hypothesis is also supported by the observation that R3M3 recognizes the loxK1 site at frequencies similar to E262G recognizing loxK2. The double and single Cre mutants, on the other hand, did not show activity on loxK1. In addition, the gel-shift experiments showed that R3M3-Cre's binding affinity for loxK2 and loxK1 half-sites is less than E262G-Cre's and the three double mutant's. Taking these results together, other mutations of R3M3 must further influence Cre-lox interactions to allow enhanced recombination of loxK2. On the one hand, this results in less efficient binding to lox half-sites, on the other hand, when complete lox sites are available, the cooperatively phenomenon between Cre enzymes binding to the same and different lox sits may compensate for this loss in binding activity. Then the postulated increased flexibility between DNA and protein seems to become advantageous for recognizing and recombining altered for sites, as seen with the in vivo and in vitro recombination assays.

Alternatively, some mutations, also silent ones, could influence protein expression, leading to a faster accumulation of enzymes and consequently to higher recombination frequency. An *E. coli* codon usage table suggested, however, that none of the identical mutations should improve Cre expression in *E. coli* remarkably.

Modeling

With the published crystal structure of four Cre molecules bound to two synapsed loxA sites after the first single strand cleavage (Guo et al., *Nature,* 389:40–46 (1997)) the identified point mutations were analyzed for being involved in DNA and/or protein interactions. All of them, including the E262 position in the J-helix or Cre were found to be not involved in either interactions in this state of the reaction. This observation indicates that the mutations which were found to account for the described novel substrate recognition in vivo and in vitro lead to this new phenotype in a less direct and obvious manner. As mentioned earlier, they may influence protein folding, resulting in a higher flexibility within the Cre-lox interface. This hypothesis is especially well supported with the described differences between binding to lox halfsites and recombination. Alternatively, they may still be involved in protein-protein (D29A) or protein-DNA (E262G) contacts before or after the formation of the clamp-like strand-exchange state.

In Vivo and In Vitro Recombination

Some additional variations of the loxK2 site were tested also. The list in Table 17 shows all the sequences of lox sites which were tested and assigns them a name, as well as their plasmid (pBS) number. In FIG. 15 the obtained in vivo recombination frequencies on all the variants of loxK2 are indicated. The additional results indicate that alterations at position 12 of the lox halfsite are of more importance for Cre-based recombination than ones at position 11.

The in vitro recombination frequencies of all six Cre enzymes tested on the lox sites listed above are given in table 15. The frequencies were calculated after quantitation of the brightness of fluorescence of the Ethidium-Bromide-stained DNA fragments on agarose-gels. Differences in temperature, ionic strength, medium composition, and enzyme concentration probably account for the observed differences between in vivo and in vitro recombination results. Most strikingly, loxP is no longer recognized with the highest frequencies in vitro. However, when the ionic strength in the in vitro assay was increased results began to resemble the ones seen in vivo. Thus, efficiency of recombination with variant lox sites by each of the Cre mutant and the wt enzyme can be further controlled in vitro by adjusting ionic strength and other in vitro conditions.

Qualitatively, however, the in vivo and in vitro recombination frequencies mirror each other. These novel Cre mutants thus possess a specificity for substrates (loxK2 and its derivatives) which are not recognized by the wt enzyme.

Gelshift Assays

DNA binding (gelshift) experiments were also done with the generated Cre double-mutants (E262G with D29A, D189N, or T316S) to analyzing binding of the variant Cre recombinases to various recombination sites. In table 16 the observed mean percentages of binding to loxP, loxK2, and loxK1 halfsites with the five different Cre mutants and the wt enzyme are given. As shown, all mutants—in contrast to the wt enzyme—do bind to loxK2 with similar frequencies, except R3M3 which shows surprisingly low retardation. As discussed above, this phenomenon may be explained with an increased tolerance, i.e., flexibility, of R3M3 for altered lox sites. On halfsites which precludes the cooperativity between Cre molecules in binding R3M3 cannot bind as tight as wt or the single and double mutants. With the loxK1 halfsite this 'binding versus recombination' difference is even more strikingly. Whereas wt and the R3M3 mutant cannot bind to the halfsite, all the other mutants can. Yet, recombination of loxK1 substrates was seen with R3M3 Cre, only. These results show clearly that simple DNA affinity does not correlate in a one-to-one fashion with recombination. Thus, inappropriate DNA binding by recombinases likely can lead to a block in recombination.

Conclusions

The in vivo data show that:
1. The E262G mutation confers a generally elevated level of recombination at a number of variant lox sites, those having any of a large number of alterations at positions 11 and 12 (and mirroring 11' and 12' alterations).
2. The D189N mutation in conjunction with the E262G mutation appears to fine tune the broadened specificity of the E262G mutation by reducing recombination at the loxK2 variants 'GG', 'TC' and 'CC' without decreasing recombination at loxK2 and the 'GT' variant. This mutation is thus useful to limit the broadened specificity of E262G.
3. The T316S mutation when in conjunction with E262G provides a slight boost in recombination frequency with the loxK2 variants 'GT' and 'CC', and has no deleterious effect on recombination at the other variant loxK2 sites.
4. The D29A mutation together with E262G boosts recombination at loxK2 and the variants 'CC' and 'GG'. D29A does not reduce recombination at the other variant lox sites or at loxP.
5. Some of the additional mutations of R3M3 must account for the further increased recombination frequency on any of the tested mutant lox sites, including loxK1 but do not compromise loxP recognition.

The disclosed variant recombinases have a number of useful features and applications. By recognizing an altered, user-defined target site, they were designed to allow both genetic targeting events in prokaryotes and eukaryotes like wt Cre but on different sites and in vitro recombination strategies. With a wider variety of possible target sequences being now accessible, multiple and defined genomic alterations will now become feasible. This opens more possibilities in designing genomic manipulations in all DNA-based organisms by site-specific recombination.

With the various genome projects under way today, there will be more and more applications for site-specific recombination to study the impact of genes or genetic control elements by genomic engineering. In addition, genome manipulations are also more frequently used to express recombinant proteins within the organism of choice.

Table 13. Presented are the results of the first four rounds of the described mutagenesis procedure for loxK2 specificity. Column one indicates the round of the mutagenesis procedure (round 0 indicates that no mutagenesis event has taken place yet, wt enzyme, only) and column two the allotted time for cre expression in induction medium. Column three presents the observed frequencies of $Kan^R$, indicating loxK2 recombination by a mutant candidate. Of note, all $Kan^R$ colonies found during this experiment were white, indicating effective loxP recombination. In column four the actual number of $Kan^R$ colonies found in each round of 1000 to $10^4$ plated is given, and the last column presents the frequency of white colonies on non-selection plates which is decreasing with every round.

Table 14. Presented are the frequencies of $Kan^R$ of six chosen candidate mutants from round three of the mutagenesis procedure (R3M1 to 6) when retesting them in the indicator strain. Also, they were tested for their performance on loxP sites in identical fashion. The obtained $Kan^R$ frequencies indicate the percentages of recombination within the allotted induction time of 2.5 hours.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

TABLE 2

List of Strains Used for Selection and Screen

| BS # | Description | Substrates | Selection and Screen |
|---|---|---|---|
| 1493 | BS583 [pBS583] | loxK1$^2$/loxP$^2$ | neo selection and lacZ screen, respectively |
| 1494 | BS583 [pBS584] | loxK2$^2$/loxP$^2$ | neo selection and lacZ screen, respectively |
| 1541 | BS583 [pBS613] | loxP$^2$/loxP$^2$ | neo selection and lacZ screen, respectively |
| 1523 | NS2300 [pBS601] | loxK1$^2$/loxP$^2$ | abfA.st screen and neo selection, respectively |
| 1524 | NS2300 [pBS602] | loxK2$^2$/loxP$^2$ | abfA.st screen and neo selection, respectively |

List of the E. coli strains used for the described selection and screening procedures for the desired Cre mutants. BS1493 and BS1494 served as selection strains for K1$^+$ or K2$^+$ Cre mutants, respectively. BS1541 was used as a control strain to determine loxP activity. BS1523 and BS1524 were used to select for P mutants. Construction and application of the different selection procedures are explained in detail in the text.

TABLE 3

Sequencing Primers for cre (SEQ ID NO:14–21)

| Primer BSB # | Sequence 5'–3' | Position (5', 3') in cre |
|---|---|---|
| 454 | TTT GGG CTA GCG AAT TCG AG | −55, −36 |
| 455 | TTT GGG CCA GCT AAA CAT GC | 273, 292 |
| 456 | CGG TGG GAG AAT GTT AAT CC | 567, 586 |
| 457 | GGA CAC AGT GCC CGT GTC | 862, 879 |
| 458 | TCT GCG TTC TGA TTT AAT CTG | 1117, 1097 |
| 459 | CCA GGC CAG GTA TCT CTG | 858, 841 |
| 460 | GTA CGT GAG ATA TCT TTA ACC C | 563, 542 |
| 461 | TTG CTG GAT AGT TTT TAC TGC C | 270, 249 |

Presented are the eight sequencing primers used for sequencing of the entire cre gene in both directions and their positions within the cre coding sequence. Primers BSB 454 to BSB457 allow sequencing of the coding strand, whereas the four remaining primers have been designed for the non-coding strand. In order to achieve a complete sequence information in both directions, about 350 bases have to be read out of each sequencing reaction. The positions given for each primer refer to its 5' and 3' end, with position 1 referring to the adenine of the ATG start codon of cre.

TABLE 4

Primers Used in the QuickChange ™ Site-Directed Mutagenesis Kit (Stratagene) (SEQ ID NO:22–27)

| Primer BSB # | Sequence 5'–3' | Position (5', 3' in cre) |
|---|---|---|
| 465 | GCTATCAACTCGCGCCCTGGGAGGGATTTTTGAAGCAACTCATCG | 765, 809 |
| 466 | GAGTTGCTTCAAAAATCCCTCCCAGGGCGCGAGTTGATAGCTGGC | 805, 761 |
| 467 | GCTATCAACTCGCGCCCTGGCAGGGATTTTTGAAGCAACTCATCG | 765, 809 |
| 468 | GAGTTGCTTCAAAAATCCCTGCCAGGGCGCGAGTTGATAGCTGGC | 805, 761 |
| 469 | GCTATCAACTCGCGCCNNNNNNNNNATTTTTGAAGCAACTCATCG | 765, 809 |
| 470 | GAGTTGCTTCAAAAATNNNNNNNNNGGCGCGAGTTGATAGCTGGC | 805, 761 |

Illustrated are the mutant oligonucleotides used in the QuickChange™ Site-Directed Mutagenesis Kit (Stratagene) to introduce single point mutations (mismatches with the wt sequence are highlighted by bold letters). With BSB465/466 a E262G mutation, and with BSB467/468 a E262A mutation is introduced in Cre. The last set of primers (BSB469/470), as indicated by the bold N, represent an equimolar mixture of all possible bases at the assigned positions. This mixture results in all possible aa combinations at positions 261 to 263 of Cre. As mentioned before, the indicated positions refer to 5' and 3' end of the oligonucleotides in the cre coding sequence.

TABLE 5

Comparison of Mutagenic and Non-Mutagenic PCR on wt cre

| Induction of cre Expression | Non-Mutagenic PCR | | Mutagenic PCR | |
|---|---|---|---|---|
| | Blue | White | Blue | White |
| SOC, 2.5 h | >99.6% | <0.4% | >99.5% | <0.5% |
| SOB + ara, 2.5 h | 19.7% | 81.3% | 60.8% | 39.2% |

The experiments presented here served two purposes: (i) to compare the influence of glucose (SOC medium) and arabinose on cre expression with pBAD33, (ii) to compare the frequencies of deleterious point mutations occurring during non-mutagenic and error-prone PCR. The first column indicates the medium used for repression (SOC), or induction of cre expression (SOB+ara). The second column compares the observed frequencies of blue and white colonies after a non-mutagenic PCR, the third column after a mutagenic PCR. Blue colonies indicate, that the loxP$^2$ flanked lacZ gene of BS583 is not excised by Cre, white ones its Cre-mediated excision. Note that the number of blue colonies resulting from empty pBAD33 vector (approximately 1% in all experiments) was subtracted before calculating the presented values. This blue background was determined with a control ligation lacking cre insertion. With glucose in the medium, only blue colonies are found, indicating that cre is not expressed. With arabinose induction, however, the frequencies of disabled Cre mutants (blue) can be determined, increasing three times under mutagenic conditions.

TABLE 6

The First Four Rounds on loxK2[2]

| Round | Status | Induction | % White (Non-Selection) | % Kan[R] (White) | Nb. Kan[R] (White) | Nb. Pooled for the Next Round |
|---|---|---|---|---|---|---|
| 1 | ox | 4 h | 83.9% | 0.01% | 1 | none |
|   | mx | 4 h | 42.4% | 0.16% | 6 | 6 |
| 2 | mxox | 2.5 h | 88.3% | 0.02% | 1 | none |
|   |  | 4 h | 82.5% | 0.56% | 47 | 47 |
|   | mxmx | 2.5 h | 13% | <0.01% | 0 | none |
|   |  | 4 h | 24% | 0.3% | 5 | none |
| 3 | mxoxox | 2.5 h | 80.7% | 0.2% | 36 | 30 |
|   |  | 4 h | 85% | 25% | 10[4] | none |
|   | mxoxmx | 2.5 h | 25.7% | 0.02% | 1 | none |
|   |  | 4 h | 21.8% | 5% | 250 | none |
| 4 | mxoxoxox | 2.5 h | 75% | 4.6% | 102 | none |
|   | mxoxoxmx | 2.5 h | <7.7% | 0.3% | 3 | none |

Presented are the results of the first four rounds of the described mutagenesis procedure for loxK2 specificity. The following symbols for the status of the cre pools have been used: "o" indicates a non-mutagenic, "m" a mutagenic PCR, and "x" stands for the shuffling step by DNase I digest and reassembly. Column one indicates the round of the mutagenesis procedure, column two its status as mentioned above, and column three the time permitted for cre expression in induction medium. In column four, the calculated percentages of white colonies on non-selection plates is indicated, decreasing with every round, especially when the pools were subjected to mutagenic PCR's twice. Column five presents the observed frequencies of Kan[R], indicating loxK2 recombination by a mutant candidate. Of note, that all Kan[R] colonies found during this experiment were white, indicating effective loxP recombination. The two last columns give the actual numbers of Kan[R] colonies found in each round (1/5 dilution) and mark the ones used as starting material for the next round.

TABLE 7

Functional Evaluation of Six Selected mxoxox K2+ Mutants and wt Cre

| Cre Candidate | Induction Time | % Kan[R] with BS1494 (loxK2[2]) | BS1541 (loxP[2]) | BS1493 (loxK1[2]) |
|---|---|---|---|---|
| wt | 2.5 h | 0.002% | 93.9% | 0.001% |
|  | 4 h | n.d. | n.d. | 0.002% |
| mxoxox 1 | 2.5 h | 66.4% | 98.2% | 0.004% |
|  | 4 h | n.d. | n.d. | 0.005% |
| mxoxox 2 | 2.5 h | 53.6% | 98% | 0.007% |
|  | 4 h | n.d. | n.d. | 0.005% |
| mxoxox 3 | 2.5 h | 66.5% | 80.5% | 0.007% |
|  | 4 h | n.d. | n.d. | 0.01% |
| mxoxox 4 | 2.5 h | 0.05% | 80.3% | 0.008% |
|  | 4 h | n.d. | n.d. | 0.006% |
| mxoxox 5 | 2.5 h | 15.2% | 81.2% | 0.006% |
|  | 4 h | n.d. | n.d. | 0.009% |
| mxoxox 6 | 2.5 h | 3.1% | 83.7% | 0.003% |
|  | 4 h | n.d. | n.d. | 0.01% |

The results of functional testing of the six chosen K2+/P+ Cre candidates compared to wt Cre are listed. All enzymes were checked on loxK2, loxP and loxK1 recombination in the selection strains BS1494, BS1493 and the control strain BS1541. In the first column the Cre candidate is indicated, in the second the allowed time for cre expression. The three following columns show the calculated percentages of Kan[R] when subjecting the different Cre mutants and wt Cre to the three selection strains. The frequency of the observed Kan[R] phenotype is considered as an indicator for the frequency of lox recombination: On loxK2, all mutants, except mxoxox 4, show remarkably increased Kan[R] frequencies compared to wt Cre. On loxP, all (including mxoxox 4), show very similar results as wt Cre, indicating, that loxP recombination is at best slightly affected. On loxK1 neither mutant nor wt Cre show more than background activity, even after four hours of cre expression. The obtained mutants are therefore characterized by a broader substrate recognition compared to the wt enzyme.

TABLE 8

Sequence Analysis of the Six mxoxox K2+/P+ Mutants

| Cre Candidate | Position | wt | → | mut | aa Change | Nb. of Isolates | Position in Cre |
|---|---|---|---|---|---|---|---|
| mxoxox 1 | 45 | CCG | | CCT | (P15P) | 2 | (N-terminal) |
|  | 86 | GAC | | GCC | D29A | 2 | A |
|  | 565 | GAC | | AAC | D189N | 2 | loop 1–2 |
|  | 642 | AGC | | AGT | (S214S) | 1 | (N-term. of I) |
|  | 679 | GTC | | ATC | V227I | 1 | I |
|  | 785 | GAA | | GGA | E262G* | 5 | J |
| mxoxox 2 | 45 | CCG | | CCT | (P15P) | 2 | (N-terminal) |
|  | 413 | GAA | | GGA | E138G | 1 | N-term. of F |
|  | 760 | AGC | | GGC | S254G | 1 | loop 5–J |
|  | 785 | GAA | | GGA | E262G* | 5 | J |
|  | 861 | TCT | | TCC | (S287S*) | 2 | N-term. of K |
|  | 946 | ACC | | TCC | T316S | 3 | loop L–M |
| mxoxox 3 | 46 | GTC | | ATC | V16I | 1 | N-terminal |
|  | 565 | GAC | | AAC | D189N | 2 | loop 1–2 |
|  | 592 | GGC | | AGC | G198S | 1 | C-term. of 2 |
|  | 668 | CGA | | CAA | R223Q | 1 | I |
|  | 764 | CAG | | CGG | Q255R | 1 | loop 5–J |
|  | 785 | GAA | | GGA | E262G* | 5 | J |
|  | 861 | TCT | | TCC | (S287S*) | 2 | N-term. of K |
|  | 920 | CCG | | CTG | P307L | 1 | L |
| mxoxox 4 | 230 | TAT | | TGT | Y77C | 1 | C |
|  | 412 | GAA | | AAA | E138K | 1 | N-term. of F |
|  | 851 | CTG | | CAG | L284Q | 2 | loop J–K |
| mxoxox 5 | 86 | GAC | | GCC | D29A | 2 | A |
|  | 302 | CGG | | CAG | R101Q* | 1 | D |
|  | 659 | CTG | | CAG | L220Q | 1 | I |
|  | 785 | GAA | | GGA | E262G* | 5 | J |
|  | 946 | ACC | | TCC | T316S | 3 | loop L–M |
| mxoxox 6 | 785 | GAA | | GGA | E262G* | 5 | J |
|  | 851 | CTG | | CAG | L284Q | 2 | loop J–K |
|  | 946 | ACC | | TCC | T316S | 3 | loop L–M |

The point mutations identified by sequence analysis in the six selected K2+/P+ mutants are listed. Column one identifies the mutants, column two the observed point mutations and their position in the cre coding sequence. Column three indicates the resulting aa changes and their positions in the Cre enzyme (silent mutations in parenthesis). DNA contacting residues, according to the crystal structure (Guo, et al., 1997), are marked by an asterisk. Column four indicates how often the different point mutations were independently found in the pool of the six mutants, and column five shows where the aa changes are located in the secondary structure of the protein. Of the altogether 31 point mutations listed, five are silent. Only one aa change, E262G, is common to all mutants with remarkably increased loxK2 activity (mxoxox 1, 2, 3, 5, and 6), suggesting that this mutation is the essential one for the observed phenotype. Nine point mutations occurred twice or three times in the pool, whereas eleven were found in one mutant only. For further information, see text and appendices A, B, and C.

TABLE 9

Functional Evaluation of Three Defined Cre Mutants for Position 262 and wt Cre

| Cre Mutant | Induction Time | % Kan$^R$ with | | |
|---|---|---|---|---|
| | | BS1494 (loxK2$^2$) | BS1541 (loxP$^2$) | BS1493 (loxK1$^2$) |
| wt | 2.5 h | 0.002% | 93.9% | 0.001% |
| E262G | 2.5 h | 2.2% | 84.2% | 0.004% |
| E262A | 2.5 h | 0.4% | 82.3% | 0.006% |
| E262W | 2.5 h | 2.9% | 81.7% | 0.003% |

The results of functional testing of three defined Cre mutants for position 262 compared to wt Cre are listed. All enzymes were checked on loxK2, loxP and loxK1 recombination in the selection strains BS1494, BS1493 and the control strain BS1541. In the first column the Cre candidate is indicated, in the second the allowed time for cre expression. The three following columns show the calculated percentages of Kan$^R$ when subjecting the different Cre mutants and wt Cre to the three selection strains. The frequency of the observed Kan$^R$ phenotype is considered as an indicator for the frequency of lox$^2$ recombination: On loxK2, E262G and E262W show approximately an $10^3$ fold increased Kan$^R$ frequency compared to wt Cre, whereas E262A results in a 200 fold increase. On loxP, all show very similar results as wt Cre, indicating, that loxP recombination is at best slightly affected. On loxK1 neither mutant nor wt Cre show more than background activity. This indicates, that E262G and E262W alone are sufficient to remarkably increase Cre's activity on loxK2, that these mutations do not increase loxK1 recognition, and that loxP activity may be slightly affected.

TABLE 10

In Vitro Evolution of the Cre recombinase

```
wtCre     TTTGGGCTAG CGAATTCGAG CTCGGTACCC GGGGATCCTC TAGACTGAGT
mxoxox1   TTTGGGCTAG CGAATTCGAG CTCGGTACCC GGGGATCCTC TAGACTGAGT
mxoxox2   TTTGGGCTAG CGAATTCGAG CTCGGTACCC GGGGATCCTC TAGACTGAGT
mxoxox3   TTTGGGCTAG CGAATTCGAG CTCGGTACCC GGGGATCCTC TAGACTGAGT
mxoxox4   TTTGGGCTAG CGAATTCGAG CTCGGTACCC GGGGATCCTC TAGACTGAGT
mxoxox5   TTTGGGCTAG CGAATTCGAG CTCGGTACCC GGGGATCCTC TAGACTGAGT
mxoxox6   TTTGGGCTAG CGAATTCGAG CTCGGTACCC GGGGATCCTC TAGACTGAGT
-55 wtCre     GTGAAATGTC CAATTTACTG ACCGTACACC AAAATTTGCC TGCATTACCG
mxoxox1   GTGAAATGTC CAATTTACTG ACCGTACACC AAAATTTGCC TGCATTACCT
mxoxox2   GTGAAATGTC CAATTTACTG ACCGTACACC AAAATTTGCC TGCATTACCT
mxoxox3   GTGAAATGTC CAATTTACTG ACCGTACACC AAAATTTGCC TGCATTACCG
mxoxox4   GTGAAATGTC CAATTTACTG ACCGTACACC AAAATTTGCC TGCATTACCG
mxoxox5   GTGAAATGTC CAATTTACTG ACCGTACACC AAAATTTGCC TGCATTACCG
mxoxox6   GTGAAATGTC CAATTTACTG ACCGTACACC AAAATTTGCC TGCATTACCG
-5        |1 wtCre     GTCGATGCAA CGAGTGATGA GGTTCGCAAG AACCTGATGG ACATGTTCAG
mxoxox1   GTCGATGCAA CGAGTGATGA GGTTCGCAAG AACCTGATGG CCATGTTCAG
mxoxox2   GTCGATGCAA CGAGTGATGA GGTTCGCAAG AACCTGATGG ACATGTTCAG
mxoxox3   ATCGATGCAA CGAGTGATGA GGTTCGCAAG AACCTGATGG ACATGTTCAG
mxoxox4   GTCGATGCAA CGAGTGATGA GGTTCGCAAG AACCTGATGG ACATGTTCAG
mxoxox5   GTCGATGCAA CGAGTGATGA GGTTCGCAAG AACCTGATGG CCATGTTCAG
mxoxox6   GTCGATGCAA CGAGTGATGA GGTTCGCAAG AACCTGATGG ACATGTTCAG
46
```

TABLE 10-continued

In Vitro Evolution of the Cre recombinase

```
wtCre    GGATCGCCAG GCGTTTTCTG AGCATACCTG GAAAATGCTT CTGTCCGTTT
mxoxox1  GGATCGCCAG GCGTTTTCTG AGCATACCTG GAAAATGCTT CTGTCCGTTT
mxoxox2  GGATCGCCAG GCGTTTTCTG AGCATACCTG GAAAATGCTT CTGTCCGTTT
mxoxox3  GGATCGCCAG GCGTTTTCTG AGCATACCTG GAAAATGCTT CTGTCCGTTT
mxoxox4  GGATCGCCAG GCGTTTTCTG AGCATACCTG GAAAATGCTT CTGTCCGTTT
mxoxox5  GGATCGCCAG GCGTTTTCTG AGCATACCTG GAAAATGCTT CTGTCCGTTT
mxoxox6  GGATCGCCAG GCGTTTTCTG AGCATACCTG GAAAATGCTT CTGTCCGTTT
96 wtCre    GCCGGTCGTG GGCGGCATGG TGCAAGTTGA ATAACCGGAA ATGGTTTCCC
mxoxox1  GCCGGTCGTG GGCGGCATGG TGCAAGTTGA ATAACCGGAA ATGGTTTCCC
mxoxox2  GCCGGTCGTG GGCGGCATGG TGCAAGTTGA ATAACCGGAA ATGGTTTCCC
mxoxox3  GCCGGTCGTG GGCGGCATGG TGCAAGTTGA ATAACCGGAA ATGGTTTCCC
mxoxox4  GCCGGTCGTG GGCGGCATGG TGCAAGTTGA ATAACCGGAA ATGGTTTCCC
mxoxox5  GCCGGTCGTG GGCGGCATGG TGCAAGTTGA ATAACCGGAA ATGGTTTCCC
mxoxox6  GCCGGTCGTG GGCGGCATGG TGCAAGTTGA ATAACCGGAA ATGGTTTCCC
146 wtCre    GCAGAACCTG AAGATGTTCG CGATTATCTT CTATATCTTC AGGCGCGCGG
mxoxox1  GCAGAACCTG AAGATGTTCG CGATTATCTT CTATATCTTC AGGCGCGCGG
mxoxox2  GCAGAACCTG AAGATGTTCG CGATTATCTT CTATATCTTC AGGCGCGCGG
mxoxox3  GCAGAACCTG AAGATGTTCG CGATTATCTT CTATATCTTC AGGCGCGCGG
mxoxox4  GCAGAACCTG AAGATGTTCG CGATTATCTT CTATGTCTTC AGGCGCGCGG
mxoxox5  GCAGAACCTG AAGATGTTCG CGATTATCTT CTATATCTTC AGGCGCGCGG
mxoxox6  GCAGAACCTG AAGATGTTCG CGATTATCTT CTATATCTTC AGGCGCGCGG
196 wtCre    TCTGGCAGTA AAAACTATCC AGCAACATTT GGGCCAGCTA AACATGCTTC
mxoxox1  TCTGGCAGTA AAAACTATCC AGCAACATTT GGGCCAGCTA AACATGCTTC
mxoxox2  TCTGGCAGTA AAAACTATCC AGCAACATTT GGGCCAGCTA AACATGCTTC
mxoxox3  TCTGGCAGTA AAAACTATCC AGCAACATTT GGGCCAGCTA AACATGCTTC
mxoxox4  TCTGGCAGTA AAAACTATCC AGCAACATTT GGGCCAGCTA AACATGCTTC
mxoxox5  TCTGGCAGTA AAAACTATCC AGCAACATTT GGGCCAGCTA AACATGCTTC
mxoxox6  TCTGGCAGTA AAAACTATCC AGCAACATTT GGGCCAGCTA AACATGCTTC
246 wtCre    ATCGTCGGTC CGGGCTGCCA CGACCAAGTG ACAGCAATGC TGTTTCACTG
mxoxox1  ATCGTCGGTC CGGGCTGCCA CGACCAAGTG ACAGCAATGC TGTTTCACTG
mxoxox2  ATCGTCGGTC CGGGCTGCCA CGACCAAGTG ACAGCAATGC TGTTTCACTG
mxoxox3  ATCGTCGGTC CGGGCTGCCA CGACCAAGTG ACAGCAATGC TGTTTCACTG
mxoxox4  ATCGTCGGTC CGGGCTGCCA CGACCAAGTG ACAGCAATGC TGTTTCACTG
mxoxox5  ATCGTCAGTC CGGGCTGCCA CGACCAAGTG ACAGCAATGC TGTTTCACTG
mxoxox6  ATCGTCGGTC CGGGCTGCCA CGACCAAGTG ACAGCAATGC TGTTTCACTG
296 wtCre    GTTATGCGGC GGATCCGAAA AGAAAACGTT GATGCCGGTG AACGTGCAAA
mxoxox1  GTTATGCGGC GGATCCGAAA AGAAAACGTT GATGCCGGTG AACGTGCAAA
mxoxox2  GTTATGCGGC GGATCCGAAA AGAAAACGTT GATGCCGGTG AACGTGCAAA
mxoxox3  GTTATGCGGC GGATCCGAAA AGAAAACGTT GATGCCGGTG AACGTGCAAA
mxoxox4  GTTATGCGGC GGATCCGAAA AGAAAACGTT GATGCCGGTG AACGTGCAAA
mxoxox5  GTTATGCGGC GGATCCGAAA AGAAAACGTT GATGCCGGTG AACGTGCAAA
mxoxox6  GTTATGCGGC GGATCCGAAA AGAAAACGTT GATGCCGGTG AACGTGCAAA
346 wtCre    ACAGGCTCTA GCGTTCGAAC GCACTGATTT CGACCAGGTT CGTTCACTCA
mxoxox1  ACAGGCTCTA GCGTTCGAAC GCACTGATTT CGACCAGGTT CGTTCACTCA
mxoxox2  ACAGGCTCTA GCGTTCGAAC GCACTGATTT CGACCAGGTT CGTTCACTCA
mxoxox3  ACAGGCTCTA GCGTTCGAAC GCACTGATTT CGACCAGGTT CGTTCACTCA
mxoxox4  ACAGGCTCTA GCGTTCAAAC GCACTGATTT CGACCAGGTT CGTTCACTCA
mxoxox5  ACAGGCTCTA GCGTTCGAAC GCACTGATTT CGACCAGGTT CGTTCACTCA
mxoxox6  ACAGGCTCTA GCGTTCGAAC GCACTGATTT CGACCAGGTT CGTTCACTCA
396 wtCre    TGGAAAATAG CGATCGCTGC CAGGATATAC GTAATCTGGC ATTTCTGGGG
mxoxox1  TGGAAAATAG CGATCGCTGC CAGGATATAC GTAATCTGGC ATTTCTGGGG
mxoxox2  TGGAAAATAG CGATCGCTGC CAGGATATAC GTAATCTGGC ATTTCTGGGG
mxoxox3  TGGAAAATAG CGATCGCTGC CAGGATATAC GTAATCTGGC ATTTCTGGGG
mxoxox4  TGGAAAATAG CGATCGCTGC CAGGATATAC GTAATCTGGC ATTTCTGGGG
mxoxox5  TGGAAAATAG CGATCGCTGC CAGGATATAC GTAATCTGGC ATTTCTGGGG
mxoxox6  TGGAAAATAG CGATCGCTGC CAGGATATAC GTAATCTGGC ATTTCTGGGG
446 wtCre    ATTGCTTATA ACACCCTGTT ACGTATAGCC GAAATTGCCA GGATCAGGGT
mxoxox1  ATTGCTTATA ACACCCTGTT ACGTATAGCC GAAATTGCCA GGATCAGGGT
mxoxox2  ATTGCTTATA ACACCCTGTT ACGTATAGCC GAAATTGCCA GGATCAGGGT
mxoxox3  ATTGCTTATA ACACCCTGTT ACGTATAGCC GAAATTGCCA GGATCAGGGT
mxoxox4  ATTGCTTATA ACACCCTGTT ACGTATAGCC GAAATTGCCA GGATCAGGGT
mxoxox5  ATTGCTTATA ACACCCTGTT ACGTATAGCC GAAATTGCCA GGATCAGGGT
mxoxox6  ATTGCTTATA ACACCCTGTT ACGTATAGCC GAAATTGCCA GGATCAGGGT
496
```

TABLE 10-continued

In Vitro Evolution of the Cre recombinase

```
wtCre    TAAAGATATC TCACGTACTG ACGGTGGGAG AATGTTAATC CATATTGGCA
mxoxox1  TAAAGATATC TCACGTACTA ACGGTGGGAG AATGTTAATC CATATTGGCA
mxoxox2  TAAAGATATC TCACGTACTG ACGGTGGGAG AATGTTAATC CATATTGGCA
mxoxox3  TAAAGATATC TCACGTACTA ACGGTGGGAG AATGTTAATC CATATTAGCA
mxoxox4  TAAAGATATC TCACGTACTG ACGGTGGGAG AATGTTAATC CATATTGGCA
mxoxox5  TAAAGATATC TCACGTACTG ACGGTGGGAG AATGTTAATC CATATTGGCA
mxoxox6  TAAAGATATC TCACGTACTG ACGGTGGGAG AATGTTAATC CATATTGGCA
546 wtCre    GAACGAAAAC GCTGGTTAGC ACCGCAGGTG TAGAGAAGGC ACTTAGCCTG
mxoxox1  GAACGAAAAC GCTGGTTAGC ACCGCAGGTG TAGAGAAGGC ACTTAGTCTG
mxoxox2  GAACGAAAAC GCTGGTTAGC ACCGCAGGTG TAGAGAAGGC ACTTAGCCTG
mxoxox3  GAACGAAAAC GCTGGTTAGC ACCGCAGGTG TAGAGAAGGC ACTTAGCCTG
mxoxox4  GAACGAAAAC GCTGGTTAGC ACCGCAGGTG TAGAGAAGGC ACTTAGCCTG
mxoxox5  GAACGAAAAC GCTGGTTAGC ACCGCAGGTG TAGAGAAGGC ACTTAGCCTG
mxoxox6  GAACGAAAAC GCTGGTTAGC ACCGCAGGTG TAGAGAAGGC ACTTAGCCTG
596 wtCre    GGGGTAACTA AACTGGTCGA GCGATGGATT TCCGTCTCTG GTGTAGCTGA
mxoxox1  GGGGTAACTA AACTGGTCGA GCGATGGATT TCCGTCTCTG GTGTAGCTGA
mxoxox2  GGGGTAACTA AACTGGTCGA GCGATGGATT TCCGTCTCTG GTGTAGCTGA
mxoxox3  GGGGTAACTA AACTGGTCGA GCGATGGATT TCCGTCTCTG GTGTAGCTGA
mxoxox4  GGGGTAACTA AACTGGTCGA GCGATGGATT TCCGTCTCTG GTGTAGCTGA
mxoxox5  GGGGTAACTA AACAGGTCGA GCGATGGATT TCCGTCTCTG GTGTAGCTGA
mxoxox6  GGGGTAACTA AACTGGTCGA GCGATGGATT TCCGTCTCTG GTGTAGCTGA
646 wtCre    TGATCCGAAT AACTACCTGT TTTGCCGGGT CAGAAAAAAT GGTGTTGCCG
mxoxox1  TGATCCGAAT AACTACCTGT TTTGCCGGGT CAGAAAAAAT GGTGTTGCCG
mxoxox2  TGATCCGAAT AACTACCTGT TTTGCCGGGT CAGAAAAAAT GGTGTTGCCG
mxoxox3  TGATCCGAAT AACTACCTGT TTTGCCGGGT CAGAAAAAAT GGTGTTGCCG
mxoxox4  TGATCCGAAT AACTACCTGT TTTGCCGGGT CAGAAAAAAT GGTGTTGCCG
mxoxox5  TGATCCGAAT AACTACCTGT TTTGCCGGGT CAGAAAAAAT GGTGTTGCCG
mxoxox6  TGATCCGAAT AACTACCTGT TTTGCCGGGT CAGAAAAAAT GGTGTTGCCG
696 wtCre    CGCCATCTGC CACCAGCCAG CTATCAACTC GCGCCCCTGGA AGGGATTTTT
mxoxox1  CGCCATCTGC CACCAGCCAG CTATCAACTC GCGCCCCTGGG AGGGATTTTT
mxoxox2  CGCCATCTGC CACCAGCCAG CTATCAACTC GCGCCCCTGGG AGGGATTTTT
mxoxox3  CGCCATCTGC CACCAGCCGG CTATCAACTC GCGCCCCTGGG AGGGATTTTT
mxoxox4  CGCCATCTGC CACCAGCCAG CTATCAACTC GCGCCCCTGGA AGGGATTTTT
mxoxox5  CGCCATCTGC CACCAGCCAG CTATCAACTC GCGCCCCTGGG AGGGATTTTT
mxoxox6  CGCCATCTGC CACCAGCCAG CTATCAACTC GCGCCCCTGGG AGGGATTTTT
746                                              785 wtCre    GAAGCAACTC ATCGATTGAT TTACGGCGCT AAGGATGACT CTGGTCAGAG
mxoxox1  GAAGCAACTC ATCGATTGAT TTACGGCGCT AAGGATGACT CTGGTCAGAG
mxoxox2  GAAGCAACTC ATCGATTGAT TTACGGCGCT AAGGATGACT CTGGTCAGAG
mxoxox3  GAAGCAACTC ATCGATTGAT TTACGGCGCT AAGGATGACT CTGGTCAGAG
mxoxox4  GAAGCAACTC ATCGATTGAT TTACGGCGCT AAGGATGACT CTGGTCAGAG
mxoxox5  GAAGCAACTC ATCGATTGAT TTACGGCGCT AAGGATGACT CTGGTCAGAG
mxoxox6  GAAGCAACTC ATCGATTGAT TTACGGCGCT AAGGATGACT CTGGTCAGAG
796 wtCre    ATACCTGGCC TGGTCTGGAC ACAGTGCCCG TGTCGGAGCC GCGCGAGATA
mxoxox1  ATACCTGGCC TGGTCTGGAC ACAGTGCCCG TGTCGGAGCC GCGCGAGATA
mxoxox2  ATACCTGGCC TGGTCCGGAC ACAGTGCCCG TGTCGGAGCC GCGCGAGATA
mxoxox3  ATACCTGGCC TGGTCCGGAC ACAGTGCCCG TGTCGGAGCC GCGCGAGATA
mxoxox4  ATACCAGGCC TGGTCTGGAC ACAGTGCCCG TGTCGGAGCC GCGCGAGATA
mxoxox5  ATACCTGGCC TGGTCTGGAC ACAGTGCCCG TGTCGGAGCC GCGCGAGATA
mxoxox6  ATACCAGGCC TGGTCTGGAC ACAGTGCCCG TGTCGGAGCC GCGCGAGATA
846 wtCre    TGGCCCGCGC TGGAGTTTCA ATACCGGAGA TCATGCAAGC TGGTGGCTGG
mxoxox1  TGGCCCGCGC TGGAGTTTCA ATACCGGAGA TCATGCAAGC TGGTGGCTGG
mxoxox2  TGGCCCGCGC TGGAGTTTCA ATACCGGAGA TCATGCAAGC TGGTGGCTGG
mxoxox3  TGGCCCGCGC TGGAGTTTCA ATACTGGAGA TCATGCAAGC TGGTGGCTGG
mxoxox4  TGGCCCGCGC TGGAGTTTCA ATACCGGAGA TCATGCAAGC TGGTGGCTGG
mxoxox5  TGGCCCGCGC TGGAGTTTCA ATACCGGAGA TCATGCAAGC TGGTGGCTGG
mxoxox6  TGGCCCGCGC TGGAGTTTCA ATACCGGAGA TCATGCAAGC TGGTGGCTGG
896 wtCre    ACCAATGTAA ATATTGTCAT GAACTATATC CGTAACCTGG ATAGTGAAAC
mxoxox1  ACCAATGTAA ATATTGTCAT GAACTATATC CGTAACCTGG ATAGTGAAAC
mxoxox2  TCCAATGTAA ATATTGTCAT GAACTATATC CGTAACCTGG ATAGTGAAAC
mxoxox3  ACCAATGTAA ATATTGTCAT GAACTATATC CGTAACCTGG ATAGTGAAAC
mxoxox4  ACCAATGTAA ATATTGTCAT GAACTATATC CGTAACCTGG ATAGTGAAAC
mxoxox5  TCCAATGTAA ATATTGTCAT GAACTATATC CGTAACCTGG ATAGTGAAAC
mxoxox6  TCCAATGTAA ATATTGTCAT GAACTATATC CGTAACCTGG ATAGTGAAAC
946
```

TABLE 10-continued

In Vitro Evolution of the Cre recombinase

```
wtCre    AGGGGCAATG GTGCGCCTGC TGGAAGATGG CGATTAGCCA TTAACGCGTA
mxoxox1  AGGGGCAATG GTGCGCCTGC TGGAAGATGG CGATTAGCCA TTAACGCGTA
mxoxox2  AGGGGCAATG GTGCGCCTGC TGGAAGATGG CGATTAGCCA TTAACGCGTA
mxoxox3  AGGGGCAATG GTGCGCCTGC TGGAAGATGG CGATTAGCCA TTAACGCGTA
mxoxox4  AGGGGCAATG GTGCGCCTGC TGGAAGATGG CGATTAGCCA TTAACGCGTA
mxoxox5  AGGGGCAATG GTGCGCCTGC TGGAAGATGG CGATTAGCCA TTAACGCGTA
mxoxox6  AGGGGCAATG GTGCGCCTGC TGGAAGATGG CGATTAGCCA TTAACGCGTA
996                              1032 wtCre    AATGATAAGC TTGGCTGTTT TGGCGGATGA GAGAAGATTT TCAGCCTGAT
mxoxox1  AATGATAAGC TTGGCTGTTT TGGCGGATGA GAGAAGATTT TCAGCCTGAT
mxoxox2  AATGATAAGC TTGGCTGTTT TGGCGGATGA GAGAAGATTT TCAGCCTGAT
mxoxox3  AATGATAAGC TTGGCTGTTT TGGCGGATGA GAGAAGATTT TCAGCCTGAT  (SEQ ID NO:28)
mxoxox4  AATGATAAGC TTGGCTGTTT TGGCGGATGA GAGAAGATTT TCAGCCTGAT  (SEQ ID NO:29)
mxoxox5  AATGATAAGC TTGGCTGTTT TGGCGGATGA GAGAAGATTT TCAGCCTGAT  (SEQ ID NO:30)
mxoxox6  AATGATAAGC TTGGCTGTTT TGGCGGATGA GAGAAGATTT TCAGCCTGAT  (SEQ ID NO:31)
1046 wtCre    ACAGATTAAA TCAGAACGCA GA                                (SEQ ID NO:32)
mxoxox1  ACAGATTAAA TCAGAACGCA GA                                (SEQ ID NO:33)
mxoxox2  ACAGATTAAA TCAGAACGCA GA                                (SEQ ID NO:34)
mxoxox3  ACAGATTAAA TCAGAACGCA GA
mxoxox4  ACAGATTAAA TCAGAACGCA GA
mxoxox5  ACAGATTAAA TCAGAACGCA GA
mxoxox6  ACAGATTAAA TCAGAACGCA GA
1096
```

ATG – Start Codon
TAG – Stop Codon
T – Point Mutation

TABLE 11

In Vitro Evolution of the Cre recombinase

```
wtCre    MSNLLTVHQN LPALPVDATS DEVRKNLMDM FRDRQAFSEH IWKMLLSVCR
mxoxox1  MSNLLTVHQN LPALPVDATS DEVRKNLMAM FRDRQAFSEH IWKMLLSVCR
mxoxox2  MSNLLTVHQN LPALPVDATS DEVRKNLMDM FRDRQAFSEH IWKMLLSVCR
mxoxox3  MSNLLTVHQN LPALPIDATS DEVRKNLMDM FRDRQAFSEH IWKMLLSVCR
mxoxox4  MSNLLTVHQN LPALPVDATS DEVRKNLMDM FRDRQAFSEH IWKMLLSVCR
mxoxox5  MSNLLTVHQN LPALPVDATS DEVRKNLMAM FRDRQAFSEH IWKMLLSVCR
mxoxox6  MSNLLTVHQN LPALPVDATS DEVRKNLMDM FRDRQAFSEH IWKMLLSVCR
1
                            A                    B wtCre    SWAAWCKLNN RKWFPAEPED VRDYLLYLQA RGLAVKTIQQ HLGQLNMLHR
mxoxox1  SWAAWCKLNN RKWFPAEPED VRDYLLYLQA RGLAVKTIQQ HLGQLNMLHR
mxoxox2  SWAAWCKLNN RKWFPAEPED VRDYLLYLQA RGLAVKTIQQ HLGQLNMLHR
mxoxox3  SWAAWCKLNN RKWFPAEPED VRDYLLYLQA RGLAVKTIQQ HLGQLNMLHR
mxoxox4  SWAAWCKLNN RKWFPAEPED VRDYLLYLQA RGLAVKTIQQ HLGQLNMLHR
mxoxox5  SWAAWCKLNN RKWFPAEPED VRDYLLYLQA RGLAVKTIQQ HLGQLNMLHR
mxoxox6  SWAAWCKLNN RKWFPAEPED VRDYLLYLQA RGLAVKTIQQ HLGQLNMLHR
51
                        C                    D wtCre    RSGLPRPSDS NAVSLVMRRI RKENVDAGER AKQALAFERT DFDQVRSLME
mxoxox1  RSGLPRPSDS NAVSLVMRRI RKENVDAGER AKQALAFERT DFDQVRSLME
mxoxox2  RSGLPRPSDS NAVSLVMRRI RKENVDAGER AKQALAFERT DFDQVRSLME
mxoxox3  RSGLPRPSDS NAVSLVMRRI RKENVDAGER AKQALAFERT DFDQVRSLME
mxoxox4  RSGLPRPSDS NAVSLVMRRI RKENVDAGER AKQALAFKRT DFDQVRSLME
mxoxox5  QSGLPRPSDS NAVSLVMRRI RKENVDAGER AKQALAFERT DFDQVRSLME
mxoxox6  RSGLPRPSDS NAVSLVMRRI RKENVDAGER AKQALAFERT DFDQVRSLME
101
                    E                        F wtCre    NSDRCQDIRN LAFGIAYNT LLFIAEIARI RVKDISRTDG GRMLIHIGRT
mxoxox1  NSDRCQDIRN LAFGIAYNT LLFIAEIARI RVKDISRTNG GRMLIHIGRT
mxoxox2  NSDRCQDIRN LAFGIAYNT LLFIAEIARI RVKDISRTDG GRMLIHIGRT
mxoxox3  NSDRCQDIRN LAFGIAYNT LLFIAEIARI RVKDISRTNG GRMLIHISRT
mxoxox4  NSDRCQDIRN LAFGIAYNT LLFIAEIARI RVKDISRTDG GRMLIHIGRT
mxoxox5  NSDRCQDIRN LAFGIAYNT LLFIAEIARI RVKDISRTDG GRMLIHIGRT
mxoxox6  NSDRCQDIRN LAFGIAYNT LLFIAEIARI RVKDISRTDG GRMLIHIGRT
151
              G            H        1         2
```

TABLE 11-continued

In Vitro Evolution of the Cre recombinase

```
wtCre    KTLVSTAGVE KALSLGVTKL VERWISVSGV ADDPNNYLFC RVRKNGVAAP
mxoxox1  KTLVSTAGVE KALSLGVTKL VERWISISGV ADDPNNYLFC RVRKNGVAAP
mxoxox2  KTLVSTAGVE KALSLGVTKL VERWISVSGV ADDPNNYLFC RVRKNGVAAP
mxoxox3  KTLVSTAGVE KALSLGVTKL VERWISVSGV ADDPNNYLFC RVRKNGVAAP
mxoxox4  KTLVSTAGVE KALSLGVTKL VERWISVSGV ADDPNNYLFC RVRKNGVAAP
mxoxox5  KTLVSTAGVE KALSLGVTKQ VERWISVSGV ADDPNNYLFC RVRKNGVAAP
mxoxox6  KTLVSTAGVE KALSLGVTKL VERWISVSGV ADDPNNYLFC RVRKNGVAAP
201
                 3         I                       4    5 wtCre    SATSQLSTRA LEGIFEATHR LIYGAKDDSG QRYLAWSGHS ARVGAARDMA
mxoxox1  SATSQLSTRA LGGIFEATHR LIYGAKDDSG QRYLAWSGHS ARVGAARDMA
mxoxox2  SATGQLSTRA LGGIFEATHR LIYGAKDDSG QRYLAWSGHS ARVGAARDMA
mxoxox3  SATSRLSTRA LGGIFEATHR LIYGAKDDSG QRYLAWSGHS ARVGAARDMA
mxoxox4  SATSQLSTRA LEGIFEATHR LIYGAKDDSG QRYQAWSGHS ARVGAARDMA
mxoxox5  SATSQLSTRA LGGIFEATHR LIYGAKDDSG QRYLAWSGHS ARVGAARDMA
mxoxox6  SATSQLSTRA LGGIFEATHR LIYGAKDDSG QRYQAWSGHS ARVGAARDMA
251
                 J                                K wtCre    RAGVSIPEIM QAGGWTNVNI VMNYIRNLDS ETGAMVRLLE DGD-    (SEQ ID NO:1)
mxoxox1  RAGVSIPEIM QAGGWTNVNI VMNYIRNLDS ETGAMVRLLE DGD-    (SEQ ID NO:35)
mxoxox2  RAGVSIPEIM QAGGWSNVNI VMNYIRNLDS ETGAMVRLLE DGD-    (SEQ ID NO:36)
mxoxox3  RAGVSIPEIM QAGGWTNVNI VMNYIRNLDS ETGAMVRLLE DGD-    (SEQ ID NO:37)
mxoxox4  RAGVSIPEIM QAGGWTNVNI VMNYIRNLDS ETGAMVRLLE DGD-    (SEQ ID NO:38)
mxoxox5  RAGVSIPEIM QAGGWSNVNI VMNYIRNLDS ETGAMVRLLE DGD-    (SEQ ID NO:39)
mxoxox6  RAGVSIPEIM QAGGWSNVNI VMNYIRNLDS ETGAMVRLLE DGD-    (SEQ ID NO:40)
301
           L          M          N
```

G – mutated residue
T – catalytic residue
F – DNA contacting residue
■ – α-helix
➤ – β sheet

TABLE 12

| Transition | Frequency | Transversion | Frequency |
|---|---|---|---|
| A-G | 29% (9) | A-C | 6.5% (2) |
| G-A | 26% (8) | C-A | <3% (0) |
| C-T | 6.5% (2) | A-T | 9.7% (3) |
| T-C | 6.5% (2) | T-A | 9.7% (3) |
|  |  | C-G | <3% (0) |
|  |  | G-C | <3% (0) |
|  |  | G-T | 6.5% (2) |
|  |  | T-G | <3% (0) |

31 point mutations could be identified in the six analyzed mutants. The mutagenic frequency can therefore be calculated as 0.5%. No frame-shift mutations, or more than one point mutation per codon of the cre sequence were found. The table classifies these mutations into the different types of transition and transversion events. Given are the frequencies and in parenthesis the actual numbers which were found. Interestingly, the A to G and vice versa transisiton occurred much more often than all other possible events. On the other hand, half of the possible transversions were not identified at all.

TABLE 13

| Round | Induction | % $Kan^R$ | Nb. $Kan^R$ | % White |
|---|---|---|---|---|
| 0 | 4 h | <0.01% | — | 100% |
| 1 | 4 h | 0.16% | 6 | 84% |
| 2 | 4 h | 0.56% | 47 | 82% |
| 3 | 2.5 h | 0.2% | 36 | 80% |
| 4 | 2.5 h | 4.6% | 102 | 75% |

TABLE 14

| | % $Kan^R$ | |
|---|---|---|
| Mutant | $loxK2^2$ | $loxP^2$ |
| wt | <0.01% | 94% |
| R3M1 | 66% | 98% |
| R3M2 | 54% | 98% |
| R3M3 | 65% | 91% |
| R3M4 | 0.02% | 93% |
| R3M5 | 15% | 91% |
| R3M6 | 3% | 94% |

TABLE 15

In Vitro Recombination Results
% of recombination is calculated from the obtained fluorescence intensity of substrate and product on an agarose gel.

% of lox-lox recombination in vitro

| Cre | loxP | ATAACTTCGTATA (SEQ ID NO:41) | | | | | | loxK2 | loxK1 | loxP-K2 | loxP-K1 |
|---|---|---|---|---|---|---|---|---|---|---|---|
| | TT | TG | GT | GG | TC | CC | AA | | | | |
| R3M3 | 25.4 | 32.1 | 36.8 | 29.7 | 8.5 | 23.9 | 36.7 | 29.9 | 31.2 | 28.9 | |
| E262G/D29A | 25.4 | 30.4 | 21.4 | 48.4 | 16.6 | 20.4 | 52.4 | 17.7 | 31.0 | 29.7 | |
| E262G/T316S | 36.4 | 37.6 | 38.6 | 47.3 | 19.6 | 23.2 | 51.1 | 32.3 | 43.2 | 29.1 | |
| E262G/D189N | 35.3 | 33.8 | 34.0 | 59.9 | 16.4 | 24.0 | 65.1 | 31.2 | 46.5 | 35.3 | |
| E262G | 30.9 | 32.1 | 27.5 | 49.2 | — | 15.2 | 46.9 | 24.3 | 35.9 | 28.4 | |
| wt | 28.7 | 0 | 45.8 | 0 | 0 | 0 | 0 | 0 | 15.9 | 4.3 | |

TABLE 16

DNA Binding to lox halfsites (Gelshift)
% of gelretardation is calculated from the obtained intensity of the shifted band (Cre bound to lox halfsite) and free lox halfsites (labeled oligonucleotides). The values given here were all obtained with 0.2 pmol of lox halfsites. Without enzyme added, no retardation of either halfsite could be observed. The obtained data was normalized for better comparability to 100% retardation on loxP halfsite for each enzyme tested.

% of lox halfsites retarded on the gel due to Cre binding

| | loxP | loxK2 | loxK1 |
|---|---|---|---|
| R3M3 | 100 | 14.8 ± 5.2 | 0.3 ± 0.2 |
| E262G/D29A | 100 | 36.6 ± 6.4 | 14.1 ± 2.7 |
| E262G/T316S | 100 | 40.7 ± 19.3 | 13.6 ± 1.7 |
| E262G/D189N | 100 | 44.2 ± 8.1 | 16.1 ± 2.9 |
| E262G | 100 | 34 ± 7.2 | 15.8 ± 6.4 |
| wt | 100 | 6 ± 1.3 | 0.8 ± 1.1 |
| | ATAACTTCGTATA (SEQ ID NO:41) | ATAACAACGTATA (SEQ ID NO:42) | ATACCTTTGTATA (SEQ ID NO:43) |

TABLE 17

```
Name          pBS#    Sequence: Halfsite - FAS1 Spacer - Inverted Halfsite

Positions in lox:  17      12      5 4 1/1' 4' 5'    11'     17'
loxP          632     ATAACTTCGTATA TACC/TTTC TATAGCAAGTTAT (SEQ ID NO:44)
loxK2         633     ATAACAACGTATA TACC/TTTC TATAGCTTGTTAT (SEQ ID NO:45)
loxK1         634     ATACCTTTGTATA TACC/TTTC TATAGAAAGGTAT (SEQ ID NO:46)
loxK2 'GG'    638     ATAACGGCGTATA TACC/TTTC TATAGCCCGTTAT (SEQ ID NO:47)
loxK2 'CC'    639     ATAACCCCGTATA TACC/TTTC TATAGCGGGTTAT (SEQ ID NO:48)
loxK2 'TC'    635     ATAACTCCGTATA TACC/TTTC TATAGCGAGTTAT (SEQ ID NO:49)
loxK2 'GT'    636     ATAACGTCGTATA TACC/TTTC TATAGCACGTTAT (SEQ ID NO:50)
loxK2 'TG'    637     ATAACTGCGTATA TACC/TTTC TATAGCCAGTTAT (SEQ ID NO:51)
```

We claim:

1. A method of identifying variant recombinases that mediate recombination at variant recombination sites, the method comprising, (a) bringing into contact a mutant recombinase, a first nucleic acid sequence comprising a first reporter gene and first and second recombination sites, wherein the first and second recombination sites are variant recombination sites, and a second nucleic acid sequence comprising a second reporter gene and third and fourth recombination sites, wherein the third and fourth recombination sites can be recombined by a non-mutant recombinase, (b) determining if recombination occurs between the first and second recombination sites, and determining if recombination occurs between the third and fourth recombination sites, wherein recombination between the first and second recombination sites indicates that the mutant recombinase is a variant recombinase that mediates recombination at variant recombination sites, wherein recombination between the third and fourth recombination sites indicates that the mutant recombinase retains the ability to mediate recombination at non-variant recombination sites.

2. The method of claim 1 wherein recombination frequency between the first and second recombination sites mediated by a non-mutant recombinase is significantly reduced.

3. The method of claim 1 wherein the first and second nucleic acid constructs are on the same nucleic acid construct.

4. The method of claim 1 wherein the recombination sites comprise recognition sequences and compatibility sequences, wherein the recognition sequences of the first and second recombination sites differ from the recognition sequences of the third and fourth recombination sties, wherein the compatibility sequences of the first and second recombination sites are sufficiently similar to allow recombination between the first and second recombination sites, and wherein the compatibility sequences of the third and fourth recombination sites are sufficiently similar to allow recombination between the third and fourth recombination sites, and wherein the compatibility sequences of the first and second recombination sites differ from the compatibility sequences of the third and fourth recombination sites such that neither the first nor the second recombination site can be recombined with either the third or the fourth recombination site.

5. The method of claim 1 or 4 wherein the first and second recombination sites have identical sequences, and wherein the third and fourth recombination sites have identical sequences.

6. The method of claim 1 wherein the first nucleic acid sequence is a first nucleic acid construct and the second nucleic acid sequence is on a second nucleic acid construct.

7. The method of claim 6 wherein the first nucleic acid construct is an extrachromosomal vector and the second nucleic acid construct is in the genome of a host cell.

8. The method of claim 1 wherein recombination between the first and second recombination sites alters the expression of the first reporter gene, wherein recombination between the first and second recombination sites is determined by determining if expression of the first reporter gene is altered, and wherein recombination between the third and fourth recombination sites alters the expression of the second reporter gene, wherein recombination between the third and fourth recombination sites is determined by determining if expression of the second reporter gene is altered.

9. The method of claim 8 wherein recombination between the first and second recombination sites allows the first reporter gene to be expressed.

10. The method of claim 9 wherein the first nucleic acid sequence further comprises a spacer sequence flanked by the first and second recombination sites, wherein the spacer sequence interrupts the first reporter gene such that the first reporter gene is not expressed, wherein recombination of the first and second recombination sites excises the spacer sequence which allows the first reporter gene to be expressed.

11. The method of claim 9 wherein a portion of the first reporter gene is inverted, wherein the inverted portion of the first reporter gene is flanked by the first and second recombination sites, wherein recombination of the first and second recombination sites inverts the inverted portion of the first reporter gene which allows the first reporter gene to be expressed.

12. The method of claim 8 wherein recombination between the first and second recombination sites prevents expression of the first reporter gene.

13. The method of claim 12 wherein the first reporter gene is flanked by the first and second recombination sites, wherein recombination of the first and second recombination sites excises the first reporter gene which prevents expression of the first reporter gene.

14. The method of claim 12 wherein a portion of the first reporter gene is flanked by the first and second recombination sites, wherein recombination of the first and second recombination sites inverts the flanked portion of the first reporter gene which prevents expression of the first reporter gene.

15. The method of claim 8 wherein recombination between the third and fourth recombination sites prevents expression of the second reporter gene to be expressed.

16. The method of claim 15 wherein the second reporter gene is flanked by the third and fourth recombination sites, wherein recombination of the third and fourth recombination sites excises the second reporter gene which prevents expression of the second reporter gene.

17. The method of claim 15 wherein a portion of the second reporter gene is flanked by the third and fourth recombination sites, wherein recombination of the third and fourth recombination sites inverts the flanked portion of the second reporter gene which prevents expression of the second reporter gene.

18. The method of claim 8 wherein recombination between the third and fourth recombination sites allows the second reporter gene to be expressed.

19. The method of claim 18 wherein a portion of the second reporter gene is inverted, wherein the inverted portion of the second reporter gene is flanked by the third and fourth recombination sites, wherein recombination of the third and fourth recombination sites inverts the inverted portion of the second reporter gene which allows the second reporter gene to be expressed.

20. The method of claim 18 wherein the second nucleic acid sequence further comprises a spacer sequence flanked by the third and fourth recombination sites, wherein the spacer sequence interrupts the second reporter gene such that the second reporter gene is not expressed, wherein recombination of the third and fourth recombination sites excises the spacer sequence which allows the second reporter gene to be expressed.

21. The method of claim 20 wherein the spacer sequence interrupts the second reporter gene such that the second reporter gene is not transcribed.

22. The method of claim 20 wherein the second reporter gene encodes a protein, wherein the spacer sequence interrupts the second reporter gene such that the protein encoded by the second reporter gene is not translated.

23. The method of claim 20 wherein the spacer sequence interrupts the second reporter gene such that the second reporter gene produces an inactive expression product.

* * * * *